(12) United States Patent
Allen et al.

(10) Patent No.: US 8,785,628 B2
(45) Date of Patent: Jul. 22, 2014

(54) TRIAZINE DERIVATIVES AS KINASE INHIBITORS

(75) Inventors: Daniel Rees Allen, Saffron Walden (GB); Roland Bürli, Saffron Walden (GB); Alan Findlay Haughan, Saffron Walden (GB); Jonathan David MacDonald, Saffron Walden (GB); Mizio Matteucci, Saffron Walden (GB); David John Nash, Saffron Walden (GB); Andrew Pate Owens, Saffron Walden (GB); Gilles Raphy, Saffron Walden (GB); Elizabeth Anne Saville-Stones, Saffron Walden (GB); Andrew Sharpe, Saffron Walden (GB)

(73) Assignee: UCB Pharma, S.A. (BE)

( * ) Notice: Subject to any disclaimer, the term of this patent is extended or adjusted under 35 U.S.C. 154(b) by 301 days.

(21) Appl. No.: 13/254,964

(22) PCT Filed: Mar. 2, 2010

(86) PCT No.: PCT/GB2010/000361
§ 371 (c)(1),
(2), (4) Date: Nov. 14, 2011

(87) PCT Pub. No.: WO2010/100405
PCT Pub. Date: Sep. 10, 2010

(65) Prior Publication Data
US 2012/0053167 A1  Mar. 1, 2012

(30) Foreign Application Priority Data

Mar. 6, 2009 (GB) .................................. 0903949.6
Sep. 7, 2009 (GB) .................................. 0915586.2

(51) Int. Cl.
*C07D 401/14* (2006.01)
*C07D 403/14* (2006.01)
*A61K 31/53* (2006.01)
*A61K 31/495* (2006.01)
*A61K 31/4709* (2006.01)
*A61K 31/4545* (2006.01)
*A61P 19/02* (2006.01)

(52) U.S. Cl.
USPC ........... 544/180; 544/189; 544/194; 540/544; 540/553; 514/241; 514/227.8; 514/231.5; 514/218

(58) Field of Classification Search
USPC .................. 544/189, 194, 180; 540/544, 553; 514/241, 227.8, 231.5, 218
See application file for complete search history.

(56) References Cited

U.S. PATENT DOCUMENTS

2007/0015758 A1  1/2007  Baruah et al.

FOREIGN PATENT DOCUMENTS

WO  09/081105 A2  7/2009

OTHER PUBLICATIONS

Rodon, J. et al. Nat. Rev. Clin. Oncol. 10, 143-153, 2013.*
Cecil Textbook of Medicine, edited by Bennet, J.C., and Plum F., 20th edition, vol. 1, 1004-101 O, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*

* cited by examiner

*Primary Examiner* — Venkataraman Balasubramanian
(74) *Attorney, Agent, or Firm* — McDonnell Boehnen Hulbert & Berghoff LLP

(57) ABSTRACT

A series of substituted [1,3,5]triazin-2-yl derivatives, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions.

12 Claims, No Drawings

TRIAZINE DERIVATIVES AS KINASE INHIBITORS

This application is a US national phase of International Application No. PCT/GB2010/000361 filed on Mar. 2, 2010, the disclosure of which is incorporated herein by reference in its entirety.

The present invention relates to a class of substituted triazine derivatives, and to their use in therapy. More particularly, the compounds in accordance with the present invention are substituted [1,3,5]triazin-2-yl derivatives. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2008/118454, WO 2008/118455 and WO 2008/118468 describe various series of quinoline and quinoxaline derivatives that are structurally related to each other and are stated to be useful to inhibit the biological activity of human PI3Kδ and to be of use in treating PI3K-mediated conditions or disorders.

Copending international patent application PCT/GB2008/004171, published on 2 Jul. 2009 as WO 2009/081105, copending international patent application PCT/GB2009/002504 (claiming priority from United Kingdom patent application 0819593.5) and copending international patent application PCT/GB2010/000243 (claiming priority from United Kingdom patent applications 0902450.6 and 0914533.5) describe separate classes of fused bicyclic heteroaryl derivatives as selective inhibitors of PI3K enzymes that are of benefit in the treatment of adverse inflammatory, autoimmune, cardiovascular, neurodegenerative, metabolic, oncological, nociceptive and ophthalmic conditions.

None of the prior art available to date, however, discloses or suggests the precise structural class of substituted triazine derivatives as provided by the present invention.

The compounds of the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3β and/or PI3Kγ and/or PI3Kδ isoform relative to other human kinases.

The present invention provides a compound of formula (I) or an N-oxide thereof, or a pharmaceutically acceptable salt or solvate thereof:

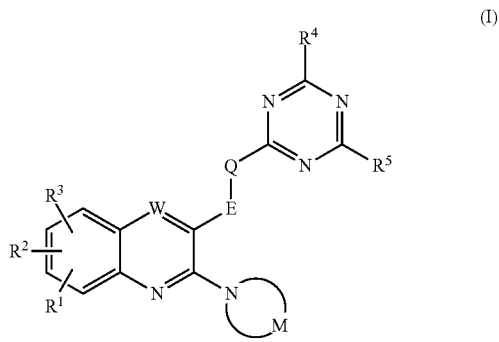

(I)

wherein

E represents an optionally substituted straight or branched $C_{1-3}$ alkylene chain;

Q represents oxygen, sulfur, N—$R^6$ or a covalent bond;

M represents the residue of an optionally substituted saturated five-, six- or seven-membered monocyclic ring containing one nitrogen atom and 0, 1, 2 or 3 additional heteroatoms independently selected from N, O and S, but containing no more than one O or S atom;

W represents C—$R^7$ or N;

$R^1$, $R^2$ and $R^3$ independently represent hydrogen, halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^4$ and $R^5$ independently represent $C_{1-6}$ alkyl, aryl, aryl($C_{1-6}$)alkyl, heteroaryl or heteroaryl($C_{1-6}$)alkyl, any of which groups may be optionally substituted by one or more substituents; or hydrogen, halogen, trifluoromethyl, —$OR^a$, —$SR^a$, —$SOR^a$, —$SO_2R^a$, —$NR^bR^c$, —$NR^cCOR^d$, —$NR^aCO_2R^d$, —$NR^cSO_2R^e$, —$COR^d$, —$CO_2R^d$, —$CONR^bR^c$ or —$SO_2NR^bR^c$;

$R^6$ represents hydrogen or $C_{1-6}$ alkyl;

$R^7$ represents hydrogen, halogen, $C_{1-6}$ alkyl or $C_{1-6}$ alkoxy;

$R^a$ represents $C_{1-6}$ alkyl, difluoromethyl or trifluoromethyl;

$R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

$R^c$ represents hydrogen, $C_{1-6}$ alkyl or $C_{3-7}$ cycloalkyl;

$R^d$ represents hydrogen or $C_{1-6}$ alkyl; and $R^e$ represents $C_{1-6}$ alkyl.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-3}$ alkylene chain" refers to a divalent straight or branched alkylene chain containing 1 to 3 carbon atoms. Typical examples include methylene, ethylene, methylmethylene, ethylmethylene and dimethylmethylene.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydro-quinoxalinyl, homopiperazinyl, morpholinyl, benzoxazinyl, homomorpholinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-c]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, benzimidazolyl, imidazo[1,2-c]pyridinyl, imidazo[4,5-b]pyridinyl, purinyl, infidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)←→enol ($CH=CHOH$) tautomers or amide ($NHC=O$)←→hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, W represents C—$R^7$. In another embodiment, W represents N.

Specific sub-classes of compounds in accordance with the present invention are represented by the compounds of formula (IA) and (IB):

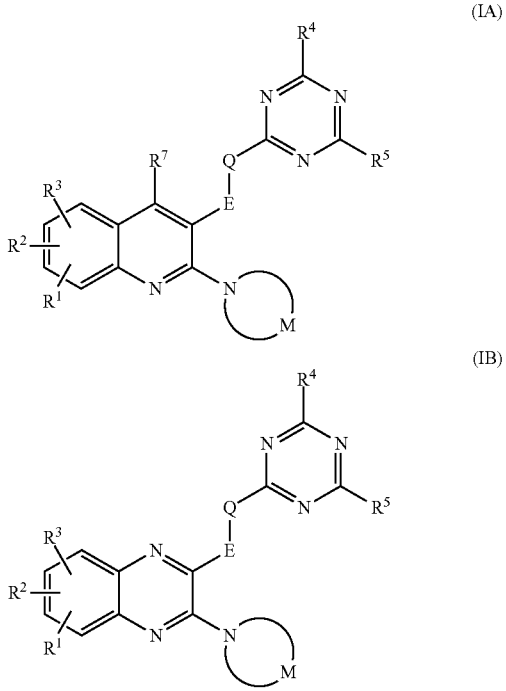

wherein E, Q, M, $R^1$, $R^2$, $R^3$, $R^4$, $R^5$ and $R^7$ are as defined above.

Typical values of E include methylene (—$CH_2$—), (methyl)methylene, ethylene (—$CH_2CH_2$—), (ethyl)methylene, (dimethyl)methylene, (methyl)ethylene and (dimethyl)ethylene, any of which chains may be optionally substituted by one or more substituents. Suitably, such chains are unsubstituted, monosubstituted or disubstituted. Preferably, such chains are unsubstituted or monosubstituted. In one embodiment, such chains are unsubstituted. In another embodiment, such chains are monosubstituted.

Examples of suitable substituents on the alkylene chain represented by E include trifluoromethyl, aryl, oxo, hydroxy, $C_{1-6}$ alkoxy, $C_{2-6}$ alkoxycarbonyl($C_{1-6}$)alkoxy, aminocarbonyl($C_{1-6}$)alkoxy, trifluoromethoxy, aminocarbonyl, $C_{1-6}$ alkylaminocarbonyl and di($C_{1-6}$)alkylaminocarbonyl.

Examples of particular substituents on the alkylene chain represented by E include trifluoromethyl, phenyl, oxo, hydroxy, ethoxy, ethoxycarbonylmethoxy, aminocarbonylmethoxy, trifluoromethoxy, aminocarbonyl, methylaminocarbonyl and dimethylamino-carbonyl.

Suitable values of E include methylene (—$CH_2$—) and (methyl)methylene.

A particular value of E is (methyl)methylene, i.e. —CH($CH_3$)—.

Another value of E is methylene, i.e. —$CH_2$—.

Suitable values of Q include oxygen and N—$R^6$.

In one embodiment, Q represents oxygen. In another embodiment, Q represents sulfur. In a further embodiment, Q represents N—$R^6$. In a still further embodiment, Q represents a covalent bond.

In one embodiment, M represents the residue of an optionally substituted saturated five-membered monocyclic ring. In another embodiment, M represents the residue of an optionally substituted saturated six-membered monocyclic ring. In a further embodiment, M represents the residue of an optionally substituted saturated seven-membered monocyclic ring.

In one embodiment, the monocyclic ring of which M is the residue contains one nitrogen atom and no additional heteroatoms (i.e. it is an optionally substituted pyrrolidin-1-yl, piperidin-1-yl or hexahydroazepin-1-yl ring). In another embodiment, the monocyclic ring of which M is the residue contains one nitrogen atom and one additional heteroatom selected from N, O and S. In a further embodiment, the monocyclic ring of which M is the residue contains one nitrogen atom and two additional heteroatoms selected from N, O and S, of which not more than one is O or S. In a still further embodiment, the monocyclic ring of which M is the residue contains one nitrogen atom and three additional heteroatoms selected from N, O and S, of which not more than one is O or S.

Selected values of the monocyclic ring of which M is the residue include pyrrolidin-1-yl, imidazolidin-1-yl, piperidin-1-yl, morpholin-4-yl, [1,4]oxazepan-4-yl, thiomorpholin-4-yl, piperazin-1-yl and [1,4]diazepan-1-yl, any of which rings may be optionally substituted by one or more substituents.

Suitable values of the monocyclic ring of which M is the residue include pyrrolidin-1-yl, imidazolidin-1-yl, piperidin-1-yl, morpholin-4-yl, thiomorpholin-4-yl, piperazin-1-yl and [1,4]diazepan-1-yl, any of which rings may be optionally substituted by one or more substituents.

Typical values of the monocyclic ring of which M is the residue include pyrrolidin-1-yl, morpholin-4-yl and piperazin-1-yl, any of which rings may be optionally substituted by one or more substituents.

In one embodiment, the monocyclic ring of which M is the residue is unsubstituted. In another embodiment, the monocyclic ring of which M is the residue is substituted by one or more substituents. In one subset of that embodiment, the monocyclic ring of which M is the residue is monosubstituted. In another subset of that embodiment, the monocyclic ring of which M is the residue is disubstituted.

Typical examples of suitable substituents on the monocyclic ring of which M is the residue include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, amino, $C_{1-6}$ alkylamino, di($C_{1-6}$)alkylamino, phenylamino, pyridinylamino, $C_{2-6}$ alkylcarbonylamino, $C_{2-6}$ alkoxycarbonylamino and aminocarbonyl. Additional examples include ($C_{3-7}$)cycloalkylcarbonyl, $C_{2-6}$ alkoxycarbonyl($C_{1-6}$)alkyl, $C_{1-6}$ alkylsulphonylamino, $C_{1-6}$ alkylaminocarbonyl, di($C_{1-6}$)alkylaminocarbonyl, di($C_{1-6}$)alkyl-aminocarbonyl($C_{1-6}$)alkyl and ($C_{3-7}$)heterocycloalkylcarbonyl($C_{1-6}$)alkyl. Further examples include trifluoroethyl, hydroxy($C_{2-6}$)alkylcarbonyl, carboxy($C_{1-6}$)alkyl and ($C_{2-6}$)alkylcarbonylamino($C_{1-6}$)alkyl.

Selected examples of suitable substituents on the monocyclic ring of which M is the residue include halogen, $C_{1-6}$ alkyl, $C_{1-6}$ alkoxy($C_{1-6}$)alkyl, $C_{1-6}$ alkylsulphonyl, hydroxy, hydroxy($C_{1-6}$)alkyl, trifluoroethyl, oxo, $C_{2-6}$ alkylcarbonyl, hydroxy($C_{2-6}$)alkyl-carbonyl, ($C_{3-7}$)cycloalkylcarbonyl, carboxy($C_{1-6}$)alkyl, $C_{2-6}$ alkoxycarbonyl, $C_{2-6}$ alkoxycarbonyl ($C_{1-6}$)alkyl, $C_{2-6}$ alkylcarbonylamino, ($C_{2-6}$)alkylcarbonylamino($C_{1-6}$)alkyl, $C_{1-6}$ alkylsulphonylamino, aminocarbonyl, di($C_{1-6}$)alkylaminocarbonyl, di($C_{1-6}$)alkyl-aminocarbonyl($C_{1-6}$)alkyl and ($C_{3-7}$)heterocycloalkylcarbonyl($C_{1-6}$)alkyl.

Illustrative examples of suitable substituents on the monocyclic ring of which M is the residue include $C_{1-6}$ alkyl, $C_{1-6}$ alkylsulphonyl, hydroxy, oxo, $C_{2-6}$ alkylcarbonyl, ($C_{3-7}$)cycloalkylcarbonyl, $C_{2-6}$ alkoxycarbonyl($C_{1-6}$)alkyl, $C_{2-6}$ alkylcarbonylamino, $C_{1-6}$ alkylsulphonylamino, di($C_{1-6}$)alkylaminocarbonyl($C_{1-6}$)alkyl and ($C_{3-7}$)heterocycloalkylcarbonyl($C_{1-6}$)alkyl.

Typical examples of specific substituents on the monocyclic ring of which M is the residue include fluoro, chloro, bromo, methyl, ethyl, isopropyl, methoxy, isopropoxy, difluoromethoxy, trifluoromethoxy, methoxymethyl, methylthio, ethylthio, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, amino, methylamino, ethylamino, dimethylamino, phenylamino, pyridinylamino, acetylamino, tert-butoxycarbonylamino and aminocarbonyl. Additional examples include cyclopropylcarbonyl, methoxycarbonylmethyl, ethoxycarbonylmethyl, methylsulphonylamino, methylaminocarbonyl, dimethylaminocarbonyl, dimethylamino-carbonylmethyl and morpholinylcarbonylmethyl. Further examples include trifluoroethyl, tert-butylcarbonyl, hydroxyacetyl, carboxymethyl and acetylaminomethyl.

Selected examples of specific substituents on the monocyclic ring of which M is the residue include fluoro, methyl, isopropyl, methoxymethyl, methylsulphonyl, hydroxy, hydroxyethyl, trifluoroethyl, oxo, acetyl, tert-butylcarbonyl, hydroxyacetyl, cyclopropylcarbonyl, carboxymethyl, methoxycarbonyl, ethoxycarbonylmethyl, acetylamino, acetylaminomethyl, methylsulphonylamino, aminocarbonyl, dimethyl-aminocarbonyl, dimethylaminocarbonylmethyl and morpholinylcarbonylmethyl.

Illustrative examples of specific substituents on the monocyclic ring of which M is the residue include methyl, methylsulphonyl, hydroxy, oxo, acetyl, cyclopropylcarbonyl, ethoxycarbonylmethyl, acetylamino, methylsulphonylamino, dimethylaminocarbonyl-methyl and morpholinylcarbonylmethyl.

A particular substituent on the monocyclic ring of which M is the residue is oxo.

Selected values of the monocyclic ring of which M is the residue include pyrrolidin-1-yl, fluoropyrrolidin-1-yl, difluoropyrrolidin-1-yl, (methoxymethyl)-pyrrolidin-1-yl, hydroxypyrrolidin-1-yl, (acetylamino)pyrrolidin-1-yl, (acetylamino-methyl)pyrrolidin-1-yl, oxoimidazolidin-1-yl, (acetylamino)piperidin-1-yl, (methylsulphonylamino)piperidin-1-yl, (aminocarbonyl)piperidin-1-yl, morpholin-4-yl, methylmorpholin-4-yl, [1,4]oxazepan-4-yl, thiomorpholin-4-yl, dioxothiomorpholin-4-yl, piperazin-1-yl, isopropylpiperazin-1-yl, dimethylpiperazin-1-yl, (methylsulphonyl)-piperazin-1-yl, (hydroxyethyl)piperazin-1-yl, (trifluoroethyl)piperazin-1-yl, oxopiperazin-1-yl, (methyl) (oxo)piperazin-1-yl, acetylpiperazin-1-yl, (tert-butylcarbonyl)piperazin-1-yl, (hydroxyacetyl)piperazin-1-yl, (cyclopropylcarbonyl) piperazin-1-yl, (carboxymethyl)-piperazin-1-yl, (methoxycarbonyl)piperazin-1-yl, (ethoxycarbonylmethyl)piperazin-1-yl, (dimethylaminocarbonyl)piperazin-1-yl, (dimethylaminocarbonylmethyl)piperazin-1-yl, (morpholinylcarbonylmethyl)piperazin-1-yl, oxo-[1,4]diazepan-1-yl and acetyl-[1,4]diazepan-1-yl.

Specific values of the monocyclic ring of which M is the residue include pyrrolidin-1-yl, 3-fluoropyrrolidin-1-yl, 3,3-difluoropyrrolidin-1-yl, 2-(methoxymethyl)-pyrrolidin-1-yl, 3-hydroxypyrrolidin-1-yl, 3-(acetylamino)pyrrolidin-1-yl, 3-(acetyl-aminomethyl)pyrrolidin-1-yl, 2-oxoimidazolidin-1-yl, 4-(acetylamino)piperidin-1-yl, 4-(methylsulphonylamino)piperidin-1-yl, 4-(aminocarbonyl)piperidin-1-yl, morpholin-4-yl, 3-methylmorpholin-4-yl, [1,4]oxazepan-4-yl, thiomorpholin-4-yl, 1,1-dioxo-thiomorpholin-4-yl, piperazin-1-yl, 4-(isopropyl)piperazin-1-yl, 3,5-dimethylpiperazin-1-yl, 4-(methylsulphonyl)piperazin-1-yl, 4-(2-hydroxyethyl)piperazin-1-yl, 4-(2,2,2-trifluoro ethyl) piperazin-1-yl, 3-oxopiperazin-1-yl, 4-methyl-3-oxopiperazin-1-yl, 4-acetylpiperazin-1-yl, 4-(tert-butylcarbonyl)piperazin-1-yl, 4-(2-hydroxy-1-oxoethyl)-piperazin-1-yl, 4-(cyclopropylcarbonyl)piperazin-1-yl, 4-(carboxymethyl)piperazin-1-yl, 4-(methoxycarbonyl)piperazin-1-yl, 4-(ethoxycarbonylmethyl)piperazin-1-yl, 4-(dimethylaminocarbonyl)piperazin-1-yl, 4-(dimethylaminocarbonylmethyl)piperazin-1-yl, 4-(morpholin-4-ylcarbonylmethyl)piperazin-1-yl, 5-oxo-[1,4]diazepan-1-yl and 4-acetyl-[1,4]diazepan-1-yl.

Typical values of the monocyclic ring of which M is the residue include pyrrolidin-1-yl, 3-hydroxypyrrolidin-1-yl, 3-(acetylamino)pyrrolidin-1-yl, 2-oxo-imidazolidin-1-yl, 4-(acetylamino)piperidin-1-yl, 4-(methylsulphonylamino) piperidin-1-yl, morpholin-4-yl, 3-methylmorpholin-4-yl, thiomorpholin-4-yl, 1,1-dioxo-thiomorpholin-4-yl, piperazin-1-yl, 4-(methylsulphonyl)piperazin-1-yl, 3-oxopiperazin-1-yl, 4-methyl-3-oxopiperazin-1-yl, 4-acetylpiperazin-1-yl, 4-(cyclopropylcarbonyl)-piperazin-1-yl, 4-(ethoxycarbonylmethyl)piperazin-1-yl, 4-(dimethylaminocarbonyl-methyl)piperazin-1-yl, 4-(morpholin-4-ylcarbonylmethyl)piperazin-1-yl and 5-oxo-[1,4]diazepan-1-yl.

Particular values of the monocyclic ring of which M is the residue include pyrrolidin-1-yl, morpholin-4-yl and 3-oxopiperazin-1-yl.

A favoured value of the monocyclic ring of which M is the residue is 3-oxo-piperazin-1-yl.

Typical values of $R^1$, $R^2$ and/or $R^3$ include hydrogen, halogen, $C_{1-6}$ alkyl, aryl($C_{1-6}$)alkyl and $C_{1-6}$ alkoxy.

Suitably, $R^1$, $R^2$ and $R^3$ independently represent hydrogen, fluoro, chloro, bromo, cyano, nitro, methyl, ethyl, trifluoromethyl, benzyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl or dimethylaminosulfonyl.

Typically, $R^1$ represents hydrogen, halogen, $C_{1-6}$ alkyl, aryl ($C_{1-6}$)alkyl or $C_{1-6}$ alkoxy.

Illustrative values of $R^1$ include hydrogen, halogen and $C_{1-6}$ alkyl.

Suitably, $R^1$ represents hydrogen or $C_{1-6}$ alkyl, typically methyl.

In one embodiment, $R^1$ represents hydrogen. In another embodiment, $R^1$ represents halogen, especially fluoro, chloro or bromo, particularly fluoro or chloro. In one aspect of that embodiment, $R^1$ represents fluoro. In another aspect of that embodiment, $R^1$ represents chloro. In a further aspect of that embodiment, $R^1$ represents bromo. In a further embodiment, $R^1$ represents $C_{1-6}$ alkyl, particularly methyl or ethyl. In one aspect of that embodiment, $R^1$ represents methyl. In another aspect of that embodiment, $R^1$ represents ethyl. In a still further embodiment, $R^1$ represents aryl($C_{1-6}$)alkyl, especially benzyl. In an additional embodiment, $R^1$ represents $C_{1-6}$ alkoxy, especially methoxy.

Typically, $R^2$ represents hydrogen or halogen.

In one embodiment, $R^2$ represents hydrogen. In another embodiment, $R^2$ represents halogen, particularly fluoro or chloro. In one aspect of that embodiment, $R^2$ represents fluoro. In another aspect of that embodiment, $R^2$ represents chloro.

Typically, $R^3$ represents hydrogen.

In a particular embodiment, $R^2$ and $R^3$ both represent hydrogen.

Typical examples of suitable substituents on $R^4$ and/or $R^5$ include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, amino, $C_{1-6}$ alkylamino, di($C_{1-6}$)alkylamino, phenylamino, pyridinylamino, $C_{2-6}$ alkylcarbonylamino, $C_{2-6}$ alkoxycarbonylamino and aminocarbonyl.

Typical examples of specific substituents on $R^4$ and/or $R^5$ include fluoro, chloro, bromo, methyl, ethyl, isopropyl, methoxy, isopropoxy, difluoromethoxy, trifluoromethoxy, methoxymethyl, methylthio, ethylthio, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, amino, methylamino, ethylamino, dimethylamino, phenylamino, pyridinylamino, acetylamino, tert-butoxycarbonylamino and aminocarbonyl.

Suitable values of $R^4$ include hydrogen, $C_{1-6}$ alkyl and —$NR^bR^c$.

Typical values of $R^4$ include hydrogen and $C_{1-6}$ alkyl.

In one embodiment, $R^4$ represents hydrogen. In another embodiment, $R^4$ represents $C_{1-6}$ alkyl, especially methyl. In a further embodiment, $R^4$ represents —$NR^bR^c$.

Suitable values of $R^5$ include $C_{1-6}$ alkyl and —$NR^bR^c$.

In one embodiment, $R^5$ represents $C_{1-6}$ alkyl, especially methyl. In another embodiment, $R^5$ represents —$NR^bR^c$.

In one embodiment, $R^6$ represents hydrogen. In another embodiment, $R^6$ represents $C_{1-6}$ alkyl, especially methyl.

Suitable values of the group $R^6$ include hydrogen and methyl.

Typically, $R^7$ represents hydrogen or $C_{1-6}$ alkyl.

In one embodiment, $R^7$ represents hydrogen. In another embodiment, $R^7$ represents halogen, particularly fluoro or chloro. In one aspect of that embodiment, $R^7$ represents fluoro. In another aspect of that embodiment, $R^7$ represents chloro. In a further embodiment, $R^7$ represents $C_{1-6}$ alkyl, especially methyl. In an additional embodiment, $R^7$ represents $C_{1-6}$ alkoxy, especially methoxy.

Suitable values of the group $R^7$ include hydrogen, fluoro, chloro, bromo, methyl and methoxy. Suitably, $R^7$ represents hydrogen or methyl. Typically, $R^7$ represents hydrogen.

In one embodiment, $R^a$ represents $C_{1-6}$ alkyl, especially methyl. In another embodiment, $R^a$ represents difluoromethyl. In a further embodiment, $R^a$ represents trifluoromethyl.

Suitably, $R^b$ represents hydrogen; or $C_{1-6}$ alkyl or aryl ($C_{1-6}$)alkyl, either of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Typical examples of suitable substituents on $R^b$ include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, amino, $C_{1-6}$ alkylamino, di($C_{1-6}$)-alkylamino, phenylamino, pyridinylamino, $C_{2-6}$ alkylcarbonylamino, $C_{2-6}$ alkoxycarbonyl-amino and aminocarbonyl.

A particular example of a suitable substituent on $R^b$ is $C_{1-6}$ alkoxy.

Typical examples of specific substituents on $R^b$ include fluoro, chloro, bromo, methyl, ethyl, isopropyl, methoxy, isopropoxy, difluoromethoxy, trifluoromethoxy, methoxymethyl, methylthio, ethylthio, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, amino, methylamino, ethylamino, dimethylamino, phenylamino, pyridinylamino, acetylamino, tert-butoxycarbonylamino and aminocarbonyl.

A particular example of a specific substituent on $R^b$ is methoxy.

In one embodiment, $R^b$ represents hydrogen. In another embodiment, $R^b$ represents $C_{1-6}$ alkyl, especially methyl. In a further embodiment, $R^b$ represents optionally substituted aryl ($C_{1-6}$)alkyl. In one aspect of that embodiment, $R^b$ represents methoxy-benzyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

In one embodiment, $R^d$ represents hydrogen. In another embodiment, $R^d$ represents $C_{1-6}$ alkyl, especially methyl.

Suitably, $R^e$ represents methyl.

One sub-class of compounds according to the invention is represented by the compounds of formula (IIA) and N-oxides thereof, and pharmaceutically acceptable salts and solvates thereof:

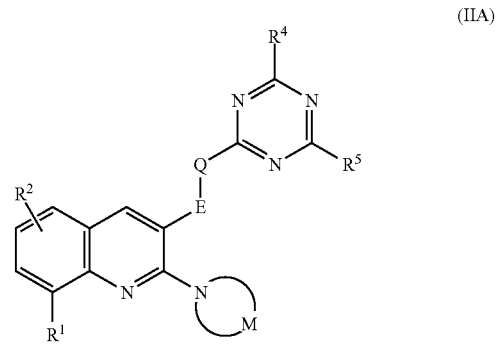

(IIA)

wherein E, Q, M, $R^1$, $R^2$, $R^4$ and $R^5$ are as defined above.

A particular subset of the compounds of formula (IIA) above is represented by the compounds of formula (IIB) and N-oxides thereof, and pharmaceutically acceptable salts and solvates thereof:

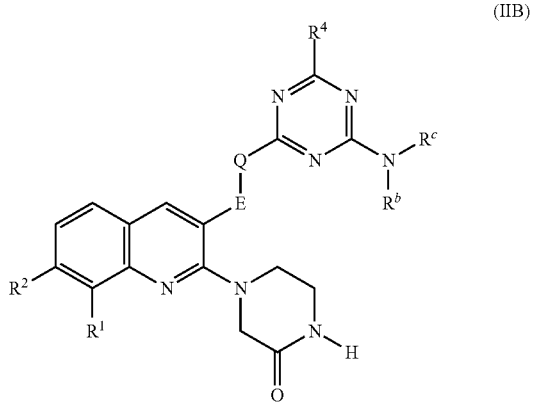

wherein E, Q, $R^1$, $R^2$, $R^4$, $R^b$ and $R^c$ are as defined above.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above wherein Q represents oxygen, sulphur or N—$R^6$ may be prepared by a process which comprises reacting a compound of formula (III) with a compound of formula (IV):

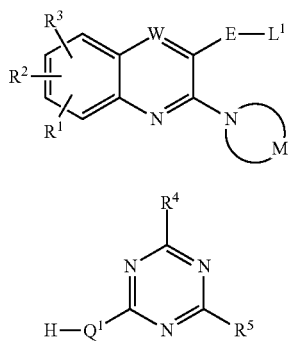

(III)

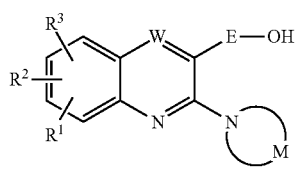

(V)

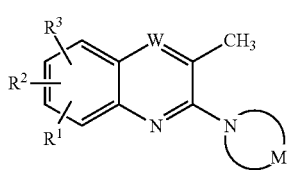

(VI)

wherein L¹ represents a suitable leaving group, Q¹ represents oxygen, sulphur or N—R⁶, and E, W, R¹, R², R³, R⁴, R⁵ and R⁶ are as defined above.

The leaving group L¹ is typically a halogen atom, e.g. bromo or iodo.

The reaction is conveniently effected at ambient or elevated temperature in a suitable solvent, e.g. N,N-dimethylformamide or acetonitrile. The reaction may be performed in the presence of a suitable base, e.g. an inorganic base such as potassium carbonate, cesium carbonate, sodium hydride or aqueous sodium hydroxide.

The intermediates of formula (III) above wherein L¹ is bromo or iodo may be prepared from a compound of formula (V):

wherein E, M, W, R¹, R² and R³ are as defined above; by bromination or iodination.

The bromination reaction is conveniently effected by stirring compound (V) with an appropriate brominating agent, e.g. phosphorus tribromide, in a suitable solvent, e.g. a halogenated hydrocarbon such as dichloromethane.

The iodination reaction is conveniently effected by stirring compound (V) with an appropriate iodinating agent, e.g. elemental iodine, in a suitable solvent, e.g. a halogenated hydrocarbon such as dichloromethane, typically in the presence of triphenylphosphine and imidazole.

Alternatively, the intermediates of formula (III) above wherein E represents methylene and L¹ is bromo may be prepared from a compound of formula (VI):

wherein M, W, R¹, R² and R³ are as defined above; by bromination.

The reaction is conveniently effected at an elevated temperature in a suitable solvent, e.g. a halogenated solvent such as carbon tetrachloride, in the presence of a suitable brominating agent, e.g. N-bromosuccinimide, typically in the presence of a catalyst such as benzoyl peroxide.

In another procedure, the compounds of formula (I) wherein Q represents oxygen may be prepared by a process which comprises reacting a compound of formula (V) as defined above with a compound of formula (VII):

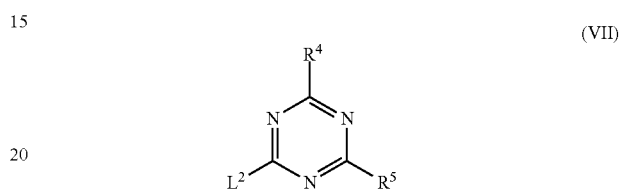

(VII)

wherein R⁴ and R⁵ are as defined above, and L² represents a suitable leaving group.

The leaving group L² is typically a halogen atom, e.g. chloro.

The reaction is conveniently effected by stirring compounds (V) and (VII) at an elevated temperature in a suitable solvent, e.g. N,N-dimethylformamide or 1,4-dioxane, typically under basic conditions, e.g. in the presence of an inorganic base such as sodium hydride.

In another procedure, the compounds of formula (I) wherein Q represents sulfur may be prepared by a process which comprises reacting a compound of formula (VII) as defined above with a compound of formula (VIII):

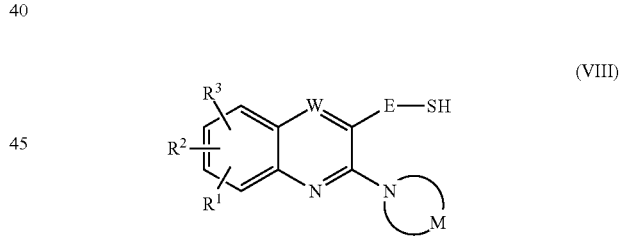

(VIII)

wherein E, M, W, R¹, R² and R³ are as defined above.

The reaction is conveniently effected by stirring compounds (VII) and (VIII) in a suitable solvent, e.g. a lower alkanol such as methanol, typically under basic conditions, e.g. in the presence of an alkali metal alkoxide such as sodium methoxide.

The intermediates of formula (VIII) may typically be prepared by treating a suitable compound of formula (III) above with thiolacetic acid; followed by treatment of the resulting compound with a base, e.g. an alkali metal alkoxide such as sodium methoxide.

In another procedure, the compounds of formula (I) wherein Q represents N—R⁶ may be prepared by a process which comprises reacting a compound of formula (VII) as defined above with a compound of formula (IX):

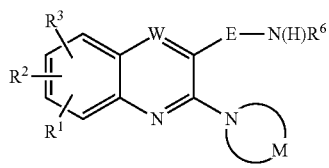

(IX)

wherein E, M, W, $R^1$, $R^2$, $R^3$ and $R^6$ are as defined above.

The reaction is conveniently effected at an elevated temperature in a suitable solvent, e.g. tetrahydrofuran, n-butanol, 1-methyl-2-pyrrolidinone (NMP) or 1,4-dioxane. The reaction may be performed in the presence of a suitable base, e.g. an organic base such as N,N-diisopropylethylamine.

The intermediates of formula (IX) wherein $R^6$ represents hydrogen may be prepared by treating a suitable compound of formula (III) above with potassium phthalimide; followed by treatment of the resulting compound with hydrazine. Alternatively, they may be prepared by treating a suitable compound of formula (III) above with sodium azide; followed by treatment of the resulting compound with triphenylphosphine.

In an additional procedure, the compounds of formula (I) wherein E represents methylene and Q represents N—$R^6$ may be prepared by a process which comprises reacting a compound of formula (X) with a compound of formula (XI):

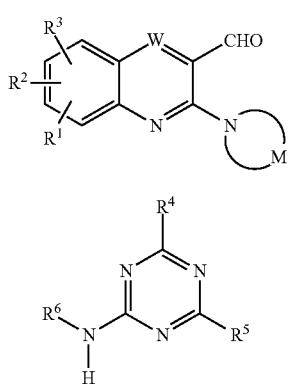

(X)

(XI)

wherein M, W, $R^1$, $R^2$, $R^3$, $R^4$, $R^5$ and $R^6$ are as defined above; under reducing conditions.

The reaction is conveniently effected by stirring compounds (X) and (XI) at an elevated temperature in a suitable solvent, e.g. a cyclic ether such as tetrahydrofuran, in the presence of a reducing agent. A suitable reducing agent comprises a mixture of di-n-butyltin dichloride and phenylsilane.

The intermediates of formula (IX) wherein E represents methylene and $R^6$ represents $C_{1-6}$ alkyl, e.g. methyl, may be prepared by treating a suitable compound of formula (X) above with a $C_{1-6}$ alkylamine, e.g. methylamine, in the presence of titanium(IV) n-propoxide and a base, e.g. an organic base such as N,N-diisopropylamine; followed by treatment of the resulting compound with a reducing agent, e.g. sodium triacetoxyborohydride.

The intermediates of formula (V) wherein E represents methylene may be prepared from the corresponding compound of formula (X) by treatment with a reducing agent, e.g. sodium borohydride.

The intermediates of formula (V), (VIII) and (IX) may be prepared by reacting a compound of formula (XII) with a compound of formula (XIII):

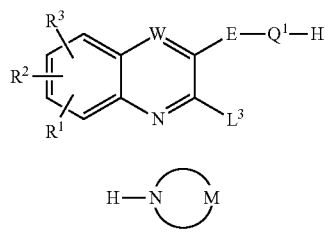

(XII)

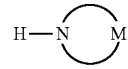

(XIII)

wherein E, $Q^1$, M, W, $R^1$, $R^2$ and $R^3$ are as defined above, and $L^3$ represents a suitable leaving group.

The leaving group $L^3$ is typically a halogen atom, e.g. chloro.

The reaction is conveniently effected at an elevated temperature in a suitable solvent, e.g. tetrahydrofuran, n-butanol or 1-methyl-2-pyrrolidinone (NMP). The reaction may be performed in the presence of a suitable base, e.g. an organic base such as N,N-diisopropylethylamine.

Where they are not commercially available, the starting materials of formula (IV), (VI), (VII), (X), (XI), (XII) and (XIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of illustration, a compound of formula (I) wherein $R^4$ and/or $R^5$ is a halogen atom, e.g. chloro, may be converted into the corresponding compound wherein $R^4$ and/or $R^5$ is amino (—$NH_2$) by treatment with ammonia. Similarly, a compound of formula (I) wherein $R^4$ and/or $R^5$ is a halogen atom, e.g. chloro, may be converted into the corresponding compound wherein $R^4$ and/or $R^5$ is $C_{1-6}$ alkylamino (e.g. methylamino or tert-butylamino), di($C_{1-6}$)alkylamino (e.g. dimethylamino) or arylamino (e.g. phenylamino) by treatment with the appropriate $C_{1-6}$ alkylamine (e.g. methylamine or tert-butylamine), di($C_{1-6}$)alkylamine (e.g. dimethylamine) or arylamine (e.g. aniline) respectively.

A compound of formula (I) wherein the monocyclic ring of which M is the residue is substituted by an ester-containing group (e.g. a ($C_{2-6}$)alkoxycarbonyl($C_{1-6}$)alkyl group such as ethoxycarbonylmethyl) may be converted into the corresponding compound wherein the monocyclic ring of which M is the residue is substituted by a carboxylic acid-containing group (e.g. a carboxy($C_{1-6}$)alkyl group such as carboxymethyl) by treatment with a basic reagent, e.g. an aqueous solution of an alkali metal hydroxide such as sodium hydroxide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 μM or better.

EXAMPLES

| Abbreviations | |
|---|---|
| DCM: | dichloromethane |
| DIPEA: | N,N-diisopropylethylamine |
| MeOH: | methanol |
| THF: | tetrahydrofuran |
| Me: | methyl |
| DMF: | N,N-dimethylformamide |
| EtOH: | ethanol |
| r.t.: | room temperature |
| $SiO_2$: | silica |
| br: | broad |
| Xantphos: | 4,5-bis(diphenylphosphino)-9,9-dimethylxanthene |
| HPLC: | High Performance Liquid Chromatography |
| LCMS: | Liquid Chromatography Mass Spectrometry |
| ES+ | Electrospray Positive Ionisation |
| ES−: | Electrospray Negative Ionisation |
| $Et_2O$: | diethyl ether |
| EtOAc: | ethyl acetate |
| NMP: | 1-methyl-2-pynolidinone |
| TFA: | trifluoroacetic acid |
| MeCN: | acetonitrile |
| DMSO: | dimethylsulfoxide |
| TEA: | triethylamine |
| RT: | retention time |
| h: | hour |
| M: | mass |

Analytical Conditions

All NMRs were obtained at 400 MHz.

Compounds were named with the aid of Beilstein Autonom or the Cambridgesoft Chemistry Cartridge (v. 9.0.0.182) software.

All reactions involving air- or moisture-sensitive reagents were performed under a nitrogen atmosphere using dried solvents and glassware. Degassing was performed by bubbling nitrogen through the reaction mixture.

| Analytical Condition | Method | Description | |
|---|---|---|---|
| 10 cm_ESCI_AmmBicarb_MeCN | 1 | Solvents: | Acetonitrile (far UV grade) |
| 10 cm_ESCI_Bicarb_MeCN | | | Water (high purity via PureLab |
| 10 cm_ESI_Bicarb | | | Option unit) with 10 mM |
| 10 cm_ESI_Bicarb_MeCN | | | ammonium hydrogencarbonate |
| 10 cm_APCI_Formic | | Column: | Waters Xterra MS 5 μm C18, 100 × 4.6 mm (Plus guard cartridge) |
| | | Flow Rate: | 2 mL/min |
| | | Gradient: | A: Water/Bicarb |
| | | | B: MeCN |
| | | Time | A % | B % |
| | | 0.00 | 95 | 5 |
| | | 0.50 | 95 | 5 |
| | | 4.00 | 5 | 95 |
| | | 5.50 | 5 | 95 |
| | | 5.60 | 95 | 5 |
| | | 6.50 | 95 | 5 |

| Analytical Condition | Method | Description | | |
|---|---|---|---|---|
| 10 cm_ESI_Formic<br>10 cm_ESI_Formic_MeCN | 2 | Solvents: | Acetonitrile (far UV grade) with<br>0.1% (v/v) formic acid<br>Water (high purity via PureLab<br>Option unit) with 0.1% formic acid | |
| | | Column: | Phenomenex Luna 5 μm C18 (2),<br>100 × 4.6 mm (Plus guard cartridge) | |
| | | Flow Rate: | 2 mL/min | |
| | | Gradient: | A: Water/formic acid<br>B: MeCN/formic acid | |
| | | Time | A % | B % |
| | | 0.00 | 95 | 5 |
| | | 3.50 | 5 | 95 |
| | | 5.50 | 5 | 95 |
| | | 5.60 | 95 | 5 |
| | | 6.50 | 95 | 5 |
| 10 cm_ESI_Formic_MeOH | 3 | Solvents: | Methanol (LC-MS grade) with<br>0.1% (v/v) formic acid<br>Water (high purity via PureLab<br>Option unit) with 0.1% formic acid | |
| | | Column: | Phenomenex Luna 5 μm C18 (2),<br>100 × 4.6 mm (Plus guard cartridge) | |
| | | Flow Rate: | 2 mL/min | |
| | | Gradient: | A: Water/formic acid<br>B: MeOH/formic acid | |
| | | Time | A % | B % |
| | | 0.00 | 95 | 5 |
| | | 3.50 | 5 | 95 |
| | | 7.00 | 5 | 95 |
| | | 7.10 | 95 | 5 |
| | | 8.00 | 95 | 5 |
| 15 cm_Formic_Slow_Sunfire_HPLC<br>15 cm_Formic_Slow<br>15 cm_ESCI_Formic | 4 | Solvents: | Acetonitrile (far UV grade) with<br>0.1% (v/v) formic acid<br>Water (high purity via PureLab<br>Ultra unit) with 0.1% formic acid | |
| | | Column: | Waters Sunfire 5 μm C18, 150 ×<br>4.6 mm | |
| | | Flow Rate: | 1 mL/min | |
| | | Gradient: | A: Water/formic acid<br>B: MeCN/formic acid | |
| | | Time | A % | B % |
| | | 0.00 | 98 | 2 |
| | | 4.00 | 98 | 2 |
| | | 20.0 | 0 | 100 |
| | | 22.0 | 0 | 100 |
| | | 22.5 | 98 | 2 |
| | | 24 | 98 | 2 |
| 15 cm_Formic_Sunfire_HPLC_MeCN | 5 | Solvents: | Acetonitrile (far UV grade) with<br>0.1% (v/v) formic acid<br>Water (high purity via PureLab<br>Ultra unit) with 0.1% formic acid | |
| | | Column: | Waters Sunfire 5 μm C18, 150 ×<br>4.6 mm | |
| | | Flow Rate: | 1 mL/min | |
| | | Gradient: | A: Water/formic acid<br>B: MeCN/formic acid | |
| | | Time | A % | B % |
| | | 0.00 | 95 | 5 |
| | | 1.00 | 95 | 5 |
| | | 30.0 | 0 | 100 |
| | | 40.0 | 0 | 100 |
| | | 40.5 | 95 | 5 |
| | | 45 | 95 | 5 |
| 25 cm_Bicarb_Slow_XBricige_HPLC_MeCN | 6 | Solvents: | Acetonitrile (far UV grade)<br>Water (high purity via PureLab<br>Option unit) with 10 mM<br>ammonium hydrogencarbonate | |
| | | Column: | Waters Xbridge 5 μm C18 (2),<br>250 × 4.6 mm | |

| Analytical Condition | Method | Description | | |
|---|---|---|---|---|
| | | Flow Rate: 1 mL/min | | |
| | | Gradient: | A: Water/formic acid | |
| | | | B: MeCN/formic acid | |
| | | Time | A % | B % |
| | | 0.00 | 95 | 5 |
| | | 2.5 | 95 | 5 |
| | | 22 | 0 | 100 |
| | | 25 | 0 | 100 |
| | | 25.1 | 95 | 5 |
| | | 26.5 | 95 | 5 |
| 25 cm_Bicarb_Xbridge_HPLC | 7 | Solvents: | Acetonitrile (far UV grade) | |
| | | | Water (high purity via PureLab Option unit) with 10 mM ammonium hydrogencarbonate | |
| | | Column: | Waters Xterra 5 µm C18 (2), 250 × 4.6 mm | |
| | | Flow Rate: 1 mL/min | | |
| | | Gradient: | A: Water/formic acid | |
| | | | B: MeCN/formic acid | |
| | | Time | A % | B % |
| | | 0.00 | 95 | 5 |
| | | 1.00 | 95 | 5 |
| | | 30.0 | 0 | 100 |
| | | 40.0 | 0 | 100 |
| | | 40.5 | 95 | 5 |
| | | 45 | 95 | 5 |
| 15 cm_Formic_Ascentis_HPLC_CH3CN | 8 | Solvents: | Acetonitrile (far UV grade) with 0.1% (v/v) formic acid | |
| | | | Water (high purity via PureLab Ultra unit) with 0.1% formic acid | |
| | | Column: | Supelco, Ascentis ® Express C18, 2.7 µm C18, 150 × 4.6 mm | |
| | | Flow Rate: 1 mL/min | | |
| | | Gradient: | A: Water/formic acid | |
| | | | B: MeCN/formic acid | |
| | | Time | A % | B % |
| | | 0.00 | 96 | 4 |
| | | 3.00 | 96 | 4 |
| | | 9.00 | 0 | 100 |
| | | 13.6 | 0 | 100 |
| | | 13.7 | 96 | 4 |
| | | 15.0 | 96 | 4 |
| 15 cm_Bicarb_ETERNITY_HPLC_CH3CN | 9 | Solvents: | 100% Acetonitrile (far UV grade) | |
| | | | Water (high purity via PureLab Ultra unit) with 10 mM ammonium bicarbonate | |
| | | Column: | Hichrom, Kromasil Eternity, 2.5 µm C18, 150 × 4.6 mm | |
| | | Flow Rate: 1 mL/min | | |
| | | Gradient: | A: 10 mM Ammonium bicarbonate in water | |
| | | | B: 100% MeCN | |
| | | Time | A % | B % |
| | | 0.00 | 95.5 | 4.5 |
| | | 3.00 | 95.5 | 4.4 |
| | | 9.00 | 0 | 100 |
| | | 13.6 | 0 | 10 |
| | | 13.7 | 95.5 | 4.5 |
| | | 15 | 95.5 | 4.5 |
| 15 cm_Bicarb_GeminiNX_HPLC_CH3CN | 10 | Solvents: | 100% Acetonitrile (far UV grade) | |
| | | | Water (high purity via PureLab Ultra unit) with 10 mM ammonium bicarbonate | |
| | | Column: | Phenomenex, Gemini NX, 3 µm C18, 150 × 4.6 mm | |
| | | Flow Rate: 1 mL/min | | |
| | | Gradient: | A: 10 mM Ammonium bicarbonate in water | |
| | | | B: 100% MeCN | |
| | | Time | A % | B % |
| | | 0.00 | 95.5 | 4.5 |
| | | 3.00 | 95.5 | 4.4 |

| Analytical Condition | Method | Description | |
|---|---|---|---|
| | | 9.00 | 0 | 100 |
| | | 13.6 | 0 | 100 |
| | | 13.7 | 95.5 | 4.5 |
| | | 15 | 95.5 | 4.5 |

Method 11: Waters Xterra MS 5μ C18, 100×4.6 mm. Mobile phase A: water with 10 mM ammonium hydrogencarbonate. Mobile phase B: MeOH. Gradient program (flow rate 2.0 mL/min):

| Time | A % | B % |
|---|---|---|
| 0.00 | 95 | 5 |
| 3.50 | 5 | 95 |
| 7.00 | 5 | 95 |
| 7.50 | 95 | 5 |
| 8.50 | 95 | 5 |

Method 12: Phenomenex Luna 5μ C18 (2), 100×4.6 mm. Mobile phase A: 99.9% water, 0.1% formic acid. Mobile phase B: 99.9% MeOH, 0.1% formic acid. Gradient program (flow rate 2.0 mL/min):

| Time | A % | B % |
|---|---|---|
| 0.00 | 95 | 5 |
| 3.50 | 5 | 95 |
| 7.00 | 5 | 95 |
| 7.50 | 95 | 5 |
| 8.50 | 95 | 5 |

Intermediate 1

(R)-2-Methylpropane-2-sulfinic acid 1-(2-chloro-8-methylquinolin-3-yl)meth-(E)-ylideneamide To a solution of 2-chloro-8-methylquinoline-3-carboxaldehyde (2.05 g, 10 mmol) in dry THF (20 mL) under nitrogen was added titanium isopropoxide (5.68 g, 20 mmol) and the mixture stirred at r.t. for 10 minutes. (R)-(+)-2-Methyl-2-propanesulfinamide (1.21 g, 10 mmol) was added to the reaction which was stirred at r.t. for 72 h. Water (20 mL) was added and the mixture was extracted with DCM (150 mL). The organic layer was separated, dried (MgSO$_4$), filtered and the solvent removed in vacuo to afford the title compound (2.4 g, 72%) as a pale yellow solid. $\delta_H$ (CDCl$_3$) 9.12 (s, 1H), 8.79 (s, 1H), 7.78 (d, J=8.4 Hz, 1H), 7.67 (d, J=6.8 Hz, 1H), 7.51 (t, J=7.8 Hz, 1H), 2.79 (s, 3H), 1.32 (s, 9H). LCMS (ES+) 309, 311 (M+H)$^+$.

Intermediate 2

(R)-2-Methylpropane-2-sulfinic acid [(S)-1-(2-chloro-8-methylquinolin-3-yl)ethyl]amide To a solution of Intermediate 1 (1.9 g, 6.15 mmol) in dry DCM (40 mL) under nitrogen cooled to −78° C. was added dropwise over 10 minutes a solution of methyl-magnesium bromide (4.1 mL, 12.3 mmol, 3.0M in Et$_2$O). The reaction mixture was allowed to warm to r.t. and stirred for 18 h. Saturated NH$_4$Cl solution (50 mL) was added and the aqueous layer was extracted with DCM (100 mL). The organic layers were combined, dried (MgSO$_4$), filtered and concentrated in vacuo to give a yellow oil. This was crystallised from petrol 40-60 to afford the title compound (900 mg, 45%) as a pale yellow solid. $\delta_H$ (CDCl$_3$) 8.17 (s, 1H), 7.64 (d, J=8.0 Hz, 1H), 7.56 (d, J=7.2 Hz, 1H), 7.45 (t, J=7.6 Hz, 1H), 5.09-5.12 (m, 1H), 3.44 (d, J=4.8 Hz, 1H), 2.77 (s, 3H), 1.71 (d, J=6.8 Hz, 3H), 1.25 (s, 9H). LCMS (ES+) 325, 327 (M+H)$^+$.

Intermediate 3

(S)-1-(2-Chloro-8-methylquinolin-3-yl)ethylamine

To a solution of Intermediate 2 (0.25 g, 0.77 mmol) in MeOH (2 mL) was added conc. HCl (1 mL) and the mixture stirred at r.t. for 2 h. The reaction was poured into DCM (100 mL) and washed with 2M NaOH solution (50 mL). The organic layer was separated, dried (MgSO$_4$), filtered and the solvent removed in vacuo to afford the title compound (0.16 g, 94%) as a white solid. $\delta_H$ (CDCl$_3$) 8.29 (s, 1H), 7.66 (d, J=8.4 Hz, 1H), 7.53 (d, J=6.8 Hz, 1H), 7.41-7.45 (m, 1H), 4.61-4.67 (m, 1H), 2.76 (s, 3H), 1.50 (d, J=4.0 Hz, 3H). LCMS (ES+) 221, 223 (M+H)$^+$.

Intermediate 4

[(S)-1-(2-Chloro-8-methylquinolin-3-yl)ethyl]carbamic acid tert-butyl ester

To a solution of Intermediate 3 (1.83 g, 3.11 mmol) in dry DCM (10 mL) under nitrogen was added DIPEA (2.7 mL, 15.6 mL) followed by a solution of di-tert-butyl dicarbonate in DCM (10 mL) dropwise. The reaction mixture was stirred at r.t. for 3 h, then diluted with DCM (10 mL) and washed with saturated NaHCO$_3$ solution (15 mL) and brine (15 mL). The organic layer was separated, dried (Na$_2$SO$_4$), filtered and the solvent removed in vacuo. Purification by column chromatography (SiO$_2$, 0-30% EtOAc in petrol 40-60) afforded the title compound (897 mg, 34%) as a white solid. $\delta_H$ (CDCl$_3$) 8.07 (s, 1H), 7.64 (d, J=8.0 Hz, 1H), 7.54 (d, J=7.2 Hz, 1H), 7.43 (t, J=7.6 Hz, 1H), 5.12-5.22 (m, 1H), 5.00-5.10 (m, 1H), 2.76 (s, 3H), 1.50-1.57 (m, 3H), 1.30-1.50 (m, 9H). LCMS (ES+) 321, 323 (M+H)$^+$.

Intermediate 5

{(S)-1-[8-Methyl-2-(morpholin-4-yl)quinolin-3-yl]ethyl}carbamic acid tert-butyl ester To a solution of Intermediate 4 (150 mg, 0.47 mmol) in NMP (3 mL) were added morpholine (0.20 mL, 2.33 mmol) and DIPEA (0.42 mL, 2.33 mmol) and the resulting solution was heated at 140° C. for 18 h. The solvent was removed in vacuo and the residue was redissolved in DCM (10 mL) and washed with water (2×2 mL). The organic layer was separated, dried (MgSO$_4$), filtered and the solvent removed in vacuo. Purification by column chromatography (SiO$_2$, 0-3% MeOH in DCM) gave the title compound (97 mg, 55%) as a beige solid. $\delta_H$ (CDCl$_3$) 7.95 (s, 1H), 7.55 (d, J=8.1 Hz, 1H), 7.45 (d, J=7.0 Hz, 1H), 7.29 (t, J=8.2 Hz, 1H), 4.97-5.24 (m, 2H), 3.85-4.00 (m, 4H), 3.38-3.69 (m, 2H), 3.14 (ddd, J 12.8, 6.4, 2.7 Hz, 2H), 2.71 (s, 3H), 1.40-1.49 (m, 12H). LCMS (ES+) 372 (M+H)+, RT 3.92 minutes.

Intermediate 6

{(S)-1-[8-Methyl-2-(pyrrolidin-1-yl)quinolin-3-yl]ethyl}carbamic acid tert-butyl ester To a solution of Intermediate 4 (150 mg, 0.47 mmol) in NMP (3 mL) were added pyrrolidine (0.20 mL, 2.33 mmol) and DIPEA (0.42 mL, 2.33 mmol). The resulting solution was heated at 140° C. for 2 h. The mixture was diluted with EtOAc (50 mL) and Et$_2$O (50 mL) and washed with brine (3×25 mL). The organic layer was separated, dried (MgSO$_4$), filtered and the solvent removed in vacuo. Purification by column chromatography (SiO$_2$, 5-10% Et$_2$O in petrol 40-60) gave the title compound (83 mg, 50%) as a white solid. $\delta_H$ (CDCl$_3$) 7.86 (s, 1H), 7.47 (d, J=8.0 Hz, 1H), 7.39 (d, J=7.0 Hz, 1H), 7.13 (dd, J 8.0, 7.0 Hz, 1H), 5.24-5.33 (m, 1H), 4.85 (s, 1H), 3.71-3.80 (m, 2H), 3.65 (s, 2H), 2.65 (s, 3H), 1.90-2.04 (m, 4H), 1.39-1.48 (m, 12H). LCMS (ES+) 356 (M+H)+.

Intermediate 7

4-[3-((S)-1-Aminoethyl)-8-methylquinolin-2-yl]-piperazin-2-one

To a solution of Intermediate 4 (500 mg, 1.56 mmol) in n-butanol (4 mL) were added piperazin-2-one (500 mg, 5.0 mmol) and DIPEA (0.50 mL, 4.0 mmol). The reaction mixture was heated at 140° C. in a sealed tube for 72 h, then poured into water (20 mL) and extracted with DCM (3×25 mL). The organic layers were combined, dried (MgSO$_4$), filtered and the solvent removed in vacuo. The residue was purified by column chromatography (SiO$_2$, 3% MeOH/DCM) to give an orange oil. This was dissolved in DCM (10 mL) and TFA (1.0 mL) was added. The mixture was stirred at r.t. for 18 h, then washed with water (3×25 mL) and saturated NaHCO$_3$ solution (25 mL). The organic layer was separated, dried (MgSO$_4$) and the solvent removed to give the title compound (330 mg, 73%) as a light brown solid. $\delta_H$ (CDCl$_3$) 7.68 (s, 1H), 7.46 (d, J=7.6 Hz, 1H), 7.41 (d, J=7.6 Hz, 1H), 7.16 (t, J=7.6 Hz, 1H), 6.20 (d, J=7.6 Hz, 1H), 5.10 (q, J=4.8 Hz, 1H), 4.70 (d, J=17.2 Hz, 1H), 3.85-4.08 (m, 3H), 3.08 (t, J=6.4 Hz, 1H), 2.68 (s, 3H), 1.73 (d, J=7.6 Hz, 3H). LCMS (ES+) 285 (M+H)+.

Intermediate 8

(R,E)-N-[(2,8-Dichloroquinolin-3-yl)methylidene]-2-methylpropane-2-sulfinamide

To a solution of 2,8-dichloroquinoline-3-carboxaldehyde (43.0 g, 0.19 mol) in anhydrous THF (500 mL) was added titanium(IV) isopropoxide (114 mL, 0.38 mol) at r.t. After stirring for 15 minutes, (R)-(−)-2-methyl-2-propanesulfinamide (23.0 g, 0.19 mol) was added and stirring was continued for 17 h at r.t. Water (1 L) was added to the reaction mixture and the precipitate obtained was filtered and washed with DCM. The organic layer was dried (Na$_2$SO$_4$) and concentrated in vacuo to give the title compound (61 g, 97%) as a pale yellow solid. $\delta_H$ (CDCl$_3$) 9.11 (1H, s), 8.83 (1H, s), 7.93 (1H, dd, J 7.54, 1.31 Hz), 7.88 (1H, dd, J 8.22, 1.31 Hz), 7.55 (1H, t, J 7.88 Hz), 1.33 (9H, s).

Intermediate 9

(R)-N-[(S)-1-(2,8-Dichloroquinolin-3-yl)ethyl]-2-methylpropane-2-sulfinamide

To a solution of Intermediate 8 (61 g, 0.18 mol) in DCM (1.5 L) was added dropwise methylmagnesium bromide (123.5 mL, 0.37 mol; 3M in Et$_2$O) over 50 minutes at −70° C. under nitrogen. The reaction mixture was allowed to reach r.t. with stirring overnight. The mixture was cooled in ice-salt as saturated aqueous NH$_4$Cl (500 mL) was slowly added with stirring. The aqueous layer was extracted with DCM (2×500 mL). The combined organic layers were dried (MgSO$_4$) and concentrated in vacuo. The residue was triturated with Et$_2$O and the solid filtered, washed with Et$_2$O and dried under reduced pressure to give the title compound (32 g, 50%) as a pale pink solid. $\delta_H$ (CDCl$_3$) 8.26 (1H, s), 7.83 (1H, dd, J 7.52, 1.32 Hz), 7.74 (1H, dd, J 8.19, 1.32 Hz), 7.49 (1H, t, J=7.86 Hz), 5.16-5.07 (1H, m), 3.47 (1H, d, J=4.63 Hz), 1.71 (3H, d, J=6.75 Hz), 1.25 (9H, s).

Intermediate 10

(S)-1-(2,8-Dichloroquinolin-3-yl)ethanamine

To a solution of Intermediate 9 (37.7 g, 0.11 mol) in MeOH (370 mL) was added 4N hydrogen chloride in 1,4-dioxane (58 mL) at r.t. The reaction mixture was stirred for 2 h and concentrated in vacuo. The residue was partitioned between 5N HCl (300 mL) and DCM (300 mL). The organic layer was extracted with 5N HCl (100 mL) and the combined aqueous layers basified with aqueous NaOH and extracted with DCM (3×500 mL) and chloroform (3×500 mL). The organic layer was dried (MgSO$_4$) and concentrated in vacuo to afford the title compound (23.7 g, 90%) as an amber oil. $\delta_H$ (CDCl$_3$) 8.40 (1H, s), 7.80 (1H, dd, J 7.51, 1.33 Hz), 7.75 (1H, dd, J 8.19, 1.33 Hz), 7.46 (1H, t, J 7.86 Hz), 4.67 (1H, q, J=6.52 Hz), 1.50 (3H, d, J=6.53 Hz).

Intermediate 11

(S)-test-Butyl 1-(2,8-dichloroquinolin-3-yl)ethylcarbamate

To a stirred solution of Intermediate 10 (23.7 g, 98 mmol) and DIPEA (51 mL, 0.3 mol) in DCM (1 L) was added di-tert-butyl dicarbonate (25.7 g, 118 mmol). The reaction mixture was allowed to stand at r.t. overnight and concentrated in vacuo. The residue was triturated with 40-60 petroleum ether, filtered, washed with 40-60 petroleum ether and dried under reduced pressure to give the title compound (28.4 g, 85%) as a colourless solid. $\delta_H$ (CDCl$_3$) 8.13 (1H, s), 7.80 (1H, dd, J 7.51, 1.32 Hz), 7.72 (1H, dd, J 8.18, 1.31 Hz), 7.46 (1H, t, J=7.85 Hz), 5.23-5.16 (1H, m), 5.10 (1H, br s), 1.55 (3H, br d, J=7.18 Hz), 1.42 (9H, br s).

Intermediate 12 tert-Butyl (S)-1-{8-chloro-2-[(S)-3-methylmorpholin-4-yl]quinolin-3-yl}ethylcarbamate A mixture of Intermediate 11 (150 mg, 0.44 mmol), (S)-3-methylmorpholine (221 mg, 2.19 mmol) and DIPEA (0.4 mL, 2.19 mmol) in NMP (3 mL) was heated at 140° C. for 72 h. More (S)-3-methylmorpholine (221 mg, 2.19 mmol) was added to the reaction mixture, which was heated at 140° C. for another 72 h. After cooling, water (10 mL) was added and the mixture extracted with Et$_2$O (100 mL). The organic layer was washed with water (3×20 mL), separated, dried (MgSO$_4$), filtered and concentrated in vacuo. The residue was purified by flash chromatography on silica, eluting with 30% EtOAc in 40-60 petroleum ether, to afford the title compound (104 mg, 53%) as a viscous yellow oil. δ$_H$ (CDCl$_3$) 7.99 (1H, s), 7.72 (1H, dd, J 7.4, 1.4 Hz), 7.63 (1H, dd, J 8.05, 1.3 Hz), 7.31 (1H, dd, J 7.8, 7.8 Hz), 5.15-5.01 (1H, m), 4.06-3.99 (1H, m), 3.93-3.85 (3H, m), 3.59 (1H, m), 3.46-3.36 (1H, m), 3.37-3.26 (1H, m), 1.50 (3H, d, J=6.7 Hz), 1.54-1.30 (9H, m), 1.19 (3H, d, J=6.3 Hz).

Intermediate 13

(S)-1-{8-Chloro-2-[(S)-3-methylmorpholin-4-yl]quinolin-3-yl}ethanamine

A solution of Intermediate 12 (100 mg, 0.25 mmol) and HCl (1.5 mL, 6.16 mmol; 4.0M in 1,4-dioxane) in 1,4-dioxane (6 mL) was stirred at r.t. overnight. The solvent was removed in vacuo and the residue purified by triturating in Et$_2$O to afford the title compound (73 mg, 78%) as a pale grey solid. δ$_H$ (CDCl$_3$) 8.97 (2H, s) 8.44 (1H, s), 7.76 (1H, d, J=7.5 Hz), 7.58 (1H, d, J=8.0 Hz), 4.98-4.87 (1H, m), 3.92 (2H, m), 3.85 (2H, m), 3.60 (1H, m), 3.13 (2H, m), 1.77 (3H, s), 1.03 (3H, d, J=5.9 Hz).

Intermediate 14

Benzyl (S)-1-(3-{(S)-1-[(pert-butyloxycarbonyl)amino]ethyl}-8-methylquinolin-2-yl)pyrrolidin-3-ylcarbamate Following the procedure described for Intermediate 12, Intermediate 4 (250 mg, 0.78 mmol), (S)-benzyl pyrrolidin-3-ylcarbamate (1 g, 3.88 mmol), NMP (5.5 mL) and DIPEA (0.69 mL, 3.88 mmol) gave the title compound (290 mg, 74%) as a dark oil. LCMS (ES+) 506 (M+H)$^+$.

Intermediate 15 tert-Butyl-1-{2-[(S)-3-aminopyrrolidin-1-yl]-8-methylquinolin-3-yl}ethylcarbamate Intermediate 14 (380 mg, 0.75 mmol) was dissolved in EtOH (20 mL) and stirred under a 1 bar pressure of hydrogen gas in the presence of 10% Pd/C (40 mg) at r.t. overnight. The mixture was filtered through Celite and the solvent was removed in vacuo to give the title compound (150 mg, 70%) as an oil. LCMS (ES+) 371 (M+H)$^+$.

Intermediate 16 tert-Butyl (S)-1-{2-[(S)-3-acetamidopyrrolidin-1-yl]-8-methylquinolin-3-yl)}ethyl-carbamate Intermediate 15 (150 mg, 0.41 mmol) was dissolved in pyridine (2 mL) in a water/ice bath. Acetyl chloride (0.05 mL, 0.75 mmol) was added and the mixture was stirred for 1 h. This mixture was diluted with DCM (20 mL) and washed with 0.5M HCl (3×10 mL). The organic layer was separated, dried (MgSO$_4$) and the solvents were removed in vacuo. Purification by column chromatography on silica, eluting with 0-100% EtOAc in isohexane, gave the title compound (80 mg, 47%). δ$_H$ (CDCl$_3$) 7.93 (1H, s), 7.52 (1H, d, J=8.0 Hz), 7.44 (1H, d, J=7.0 Hz), 7.28-7.17 (2H, m), 6.65 (1H, s), 4.85 (1H, s), 4.58 (1H, s), 3.93 (1H, m), 3.72-3.61 (3H, m), 2.67 (3H, s), 2.40-2.24 (2H, m), 2.08-1.93 (3H, m), 1.53-1.40 (12H, m).

Intermediate 17

(S)-tert-Butyl 1-[8-methyl-2-(thiomorpholin-4-yl)quinolin-3-yl]ethylcarbamate

Following the procedure described for Intermediate 12, Intermediate 4 (150 mg, 0.47 mmol), thiomorpholine (0.071 mL, 0.71 mmol), NMP (3 mL) and DIPEA (0.41 mL, 2.33 mmol) gave the title compound (160 mg, 88%) as a brown oil. δ$_H$ (CDCl$_3$) 7.93 (1H, s), 7.54 (1H, d, J=8.0 Hz), 7.47-7.41 (1H, m), 7.32-7.23 (1H, m), 5.13-4.95 (2H, m), 3.75-3.65 (2H, m), 3.50-3.40 (2H, m), 2.96-2.89 (2H, m), 2.88-2.79 (2H, m), 2.68 (3H, s), 1.46-1.40 (12H, m). LCMS (ES+) 396 (M+H)$^+$, RT 21.23 minutes (Method 6).

Intermediate 18

(S)-tert-Butyl 1-[8-chloro-2-(1,1-dioxothiomorpholin-4-yl)quinolin-3-yl]ethylcarbamate Following the procedure described for Intermediate 12, Intermediate 11 (300 mg, 0.88 mmol), thiomorpholine 1,1-dioxide (596 mg, 4.40 mmol), NMP (3 mL) and DIPEA (1.53 mL, 8.80 mmol) gave the title compound (192 mg, 50%) as a white glass. δ$_H$ (CDCl$_3$) 8.06 (1H, s), 7.74 (1H, dd, J 7.5, 1.3 Hz), 7.65 (1H, dd, J 8.1, 1.4 Hz), 7.38-7.29 (1H, m), 5.07 (1H, m), 4.97 (1H, m), 4.11-4.00 (4H, m), 3.59 (2H, m), 3.23-3.16 (2H, m), 1.45-1.39 (12H, m).

Intermediate 19

(S)-tert-Butyl 1-{8-chloro-2-[4-(methylsulfonamido)piperidin-1-yl]quinolin-3-yl}ethyl-carbamate Following the procedure described for Intermediate 12, Intermediate 11 (300 mg, 0.88 mmol), N-(piperidin-4-yl)methanesulfonamide (783 mg, 4.40 mmol), NMP (3 mL) and DIPEA (1.53 mL, 8.80 mmol) gave the title compound (0.39 mg, 92%) as a clear glass. δ$_H$ (CDCl$_3$) 7.97 (1H, s) 7.70 (1H, m), 7.61 (1H, m), 7.30 (1H, d, J=7.8 Hz), 5.09 (1H, br s), 4.94 (1H br s), 4.38 (1H, d), 3.84 (1H, d), 3.66-3.55 (2H, m), 3.35-3.27 (1H, m), 3.03 (3H, s), 3.02-2.89 (1H, m), 2.18 (2H, m), 1.98-1.86 (1H, m), 1.80-1.69 (1H, m), 1.45-1.41 (12H, m).

Intermediate 20

(S)-tert-Butyl 1-[2-(4-acetylpiperazin-1-yl)-8-chloroquinolin-3-yl]ethylcarbamate Following the procedure described for Intermediate 12, Intermediate 11 (300 mg, 0.88 mmol), 1-(piperazin-1-yl)ethanone (564 mg, 4.40 mmol), NMP (3 mL) and DIPEA (1.53 mL, 8.80 mmol) gave the title compound (0.25 mg, 65%) as a clear glass. δ$_H$ (CDCl$_3$) 8.01 (1H, s), 7.71 (1H, dd, J 7.5, 1.4 Hz), 7.62 (1H, dd, J 8.0, 1.4 Hz), 7.31 (1H, t, J=7.8 Hz), 5.08 (1H, m), 3.94-3.71 (3H, m), 3.67-3.52 (3H, m), 3.39-3.15 (2H, m), 2.16 (3H, s), 1.76 (1H, d, J=2.5 Hz), 1.48-1.43 (12H, m).

Intermediate 21

(S)-tert-Butyl 1-[8-chloro-2-(3-oxopiperazin-1-yl)quinolin-3-yl]ethylcarbamate

A mixture of Intermediate 11 (0.53 g, 1.56 mmol), 2-oxopiperazine (0.78 g, 7.78 mmol) and DIPEA (1.35 mL, 7.78 mmol) in NMP (10 mL) was heated at 140° C. for 16 h. After cooling, Et$_2$O (250 mL) was added and the mixture washed with water (3×100 mL) and brine (100 mL). The organic layer was separated, dried (MgSO$_4$), concentrated in vacuo and the residue purified by column chromatography on silica, eluting with 0-100% EtOAc in isohexane, to afford the title compound (0.34 g, 53%) as a pale yellow solid. $\delta_H$ (CDCl$_3$) 8.03 (1H, s), 7.72 (1H, dd, J 7.5, 1.3 Hz), 7.63 (1H, dd, J 8.0, 1.3 Hz), 7.32 (1H, t, J=7.8 Hz), 6.32 (1H, br s), 5.15-4.93 (2H, m), 4.36 (1H, d, J=17.7 Hz), 4.13-3.84 (2H, m), 3.77-3.68 (1H, m), 3.45 (2H, m), 1.48-1.42 (12H, m).

Intermediate 22

(E)-N-[(2-Chloro-7-fluoroquinolin-3-yl)methylidene]-(R)-2-methylpropane-2-sulfinamide To a solution of 2-chloro-7-fluoroquinoline-3-carboxaldehyde (6.3 g, 30 mmol) in dry THF (200 mL) under nitrogen was added titanium(IV) isopropoxide (17.0 g, 60 mmol) and the reaction mixture stirred at r.t. for 10 minutes. (R)-(−)-2-Methyl-2-propane-sulfinamide (3.6 g, 30 mmol) was added to the reaction mixture, which was stirred at r.t. for 72 h and partitioned between water (20 mL) and DCM (150 mL). The organic layer was dried (MgSO$_4$), filtered and concentrated in vacuo to give the title compound (7.2 g, 76%) as a pale yellow solid. $\delta_H$ (CDCl$_3$) 9.09 (1H, s), 8.83 (1H, s), 7.96 (1H, dd, J=6.0 Hz), 7.69 (1H, d, J=7.2 Hz), 7.42 (1H, t, J=8.4 Hz), 1.32 (9H, s).

Intermediate 23

(E)-N-[(2-Chloro-7-fluoro-8-methylquinolin-3-yl)methylidene]-(R)-2-methylpropane-2-sulfinamide Following the procedure for Intermediate 22, 2-chloro-7-fluoro-8-methyl-quinoline-3-carbaldehyde (6.6 g, 29.5 mmol), titanium(IV) isopropoxide (17 g; 60 mmol), (R)-(−)-2-methyl-2-propanesulfinamide (3.6 g, 29.5 mmol) and THF (200 mL) gave the title compound (8.3 g, 86%) as a yellow solid. $\delta_H$ (CDCl$_3$) 9.12 (1H, s), 8.73 (1H, s), 7.71 (1H, dd, J=6.0 Hz), 7.40 (1H, t, J=8.2 Hz), 2.69 (3H, s), 1.32 (9H, s).

Intermediate 24

N-[(S)-1-(2-Chloro-7-fluoroquinolin-3-yl)ethyl]-(R)-2-methylpropane-2-sulfinamide To a solution of Intermediate 22 (7.2 g, 23.5 mmol) in dry DCM (40 mL) under nitrogen was added dropwise over 10 minutes at −78° C. a solution of methylmagnesium bromide (16.0 mL, 48 mmol; 3.0M in Et$_2$O). After warming to r.t., the reaction mixture was stirred for 18 h and partitioned between a saturated solution of NH$_4$Cl (50 mL) and DCM (100 mL). The organic layer was dried (MgSO$_4$), filtered and concentrated in vacuo to give a yellow oil which was crystallised from 40-60 petroleum ether to give the title compound (4.0 g, 53%) as a pale yellow solid. $\delta_H$ (CDCl$_3$) 8.23 (1H, s), 7.16 (1H, dd, J=6.0 Hz), 7.65 (1H, d, J=7.2 Hz), 7.46 (1H, t, J=8.4 Hz), 5.16 (1H, q, J=6.8 Hz), 3.45 (1H, br s), 1.71 (3H, d, J=6.8 Hz), 1.26 (9H, s).

Intermediate 25

N-[(S)-1-(2-Chloro-7-fluoro-8-methylquinolin-3-yl)ethyl]-(R)-2-methylpropane-2-sulfinamide Following the procedure described for Intermediate 24, Intermediate 23 (8.3 g, 25.4 mmol), methylmagnesium bromide (16.0 mL, 48 mmol; 3.0M in Et$_2$O), and DCM (100 mL) gave the title compound (4.2 g, 48%) as a yellow solid. $\delta_H$ (CDCl$_3$) 8.17 (1H, s), 7.63 (1H, dd, J=6.0 Hz), 7.32 (1H, t, J=8.8 Hz), 5.16 (1H, q, J=6.8 Hz), 3.45 (1H, d, J=6.8 Hz), 2.66 (3H, s) 1.70 (3H, d, J=6.8 Hz), 1.26 (9H, s).

Intermediate 26

(S)-tert-Butyl 1-(2-chloro-7-fluoroquinolin-3-yl)ethylcarbamate

To a solution of Intermediate 24 (4.0 g, 12.17 mmol) in MeOH (20 mL) was added conc. HCl (1 mL) and the mixture stirred at r.t. for 2 h. The reaction mixture was partitioned between DCM (100 mL) and 2M NaOH solution (50 mL). The organic layer was dried (MgSO$_4$) and filtered. To this filtrate was added DIPEA (3.0 mL, 15.0 mmol) followed by a solution of di-tert-butyl dicarbonate (3.0 g, 13.76 mmol) in DCM (10 mL) dropwise. The reaction mixture was stirred at r.t. for 3 h, then diluted with DCM (10 mL) and washed with saturated NaHCO$_3$ solution (15 mL) and brine (15 mL). The organic layer was dried (MgSO$_4$), concentrated in vacuo and purified by column chomatography on silica, eluting with 0-30% EtOAc in 40-60 petroleum ether, to give the title compound (3.4 g, 86%) as a white solid. $\delta_H$ (CDCl$_3$) 8.23 (1H, s), 7.16 (1H, dd, J=6.0 Hz), 7.65 (1H, d, J 7.2 Hz), 7.46 (1H, t, J=8.4 Hz), 5.18 (1H, br q, J=6.8 Hz), 3.49 (1H, d, J=6.8 Hz), 1.54 (3H, d, J=6.8 Hz), 1.48 (9H, s).

Intermediate 27

(S)-tert-Butyl 1-(2-chloro-7-fluoro-8-methylquinolin-3-yl)ethylcarbamate

Following the procedure described for Intermediate 26, Intermediate 25 (4.2 g, 12.2 mmol), conc. HCl (1 mL), di-tert-butyl dicarbonate (2.7 g, 12.2 mmol) and DIPEA (1.6 g, 12.2 mmol) gave the title compound (4.38 g, 90%) as a yellow solid. $\delta_H$ (CDCl$_3$) 8.07 (1H, s), 7.62 (1H, dd, J=6.0 Hz), 7.30 (1H, t, J=8.8 Hz), 5.17 (1H, m), 5.07 (1H, br s), 2.65 (3H, s) 1.54 (3H, d, J=6.4 Hz), 1.42 (9H, s).

Intermediate 28

(S)-1-[8-Methyl-2-(pyrrolidin-1-yl)quinolin-3-yl]ethanamine

Intermediate 2 (100 mg, 0.31 mmol), pyrrolidine (0.052 mL, 0.62 mmol), DIPEA (0.107 mL, 0.62 mmol) and NMP (2 mL) were combined in a sealed tube and heated under microwave irradiation to 150° C. for 75 minutes. After cooling, conc. HCl (2 mL) was slowly added and the solution was left to stand for 1 h. The reaction mixture was diluted with water and washed several times with DCM. The aqueous layer was then basified to pH 10 with 15% NaOH and extracted several times with DCM. The combined organic layers were dried (MgSO$_4$) and concentrated in vacuo to give the title compound (79.5 mg, 100%) as a pale yellow gum. LCMS (ES+) 256 (M+H)$^+$.

Intermediate 29

(S)-tert-Butyl 1-[7-fluoro-8-methyl-2-(3-oxopiperazin-1-yl)quinolin-3-yl]ethylcarbamate Following the procedure described for Intermediate 12, Intermediate 27 (280 mg, 0.83 mmol), 2-oxopiperazine (86 mg, 1.0 mmol) and DIPEA (0.5 mL, 3.8 mmol) in n-butanol (2.0 mL) gave the title compound (270 mg, 81%) as a purple oil. $\delta_H$ (CDCl$_3$) 7.99 (1H, s), 7.54 (1H, dd, J 8.9, 6.0 Hz), 7.17 (1H, t, J=9.0 Hz), 6.73 (1H, br s), 5.10 (2H, br s), 4.28 (1H, d, J 17.5 Hz), 3.95 (1H, d, J 17.5 Hz), 3.89-3.77 (1H, m), 3.70-3.51 (1H, m), 3.44-3.35 (2H, m), 2.58 (3H, d, J=2.4 Hz), 1.50-1.30 (12H, m).

Intermediate 30

(S)-4-[3-(1-Aminoethyl)-8-chloroquinolin-2-yl]piperazin-2-one

TFA (1 mL) was added to a stirred solution of Intermediate 21 (0.34 g, 0.83 mmol) in DCM (5 mL) and the mixture was allowed to stand at r.t. for 16 h before being concentrated in vacuo. The residue was dissolved in DCM (20 mL) and washed with 0.1M NaOH solution. 15% NaOH was added to the aqueous layer which was extracted with EtOAc (20 mL) and DCM (2×20 mL). The combined organics were dried (MgSO$_4$) and concentrated in vacuo to afford the title compound (0.24 g, 95%) as a pale orange-yellow solid. $\delta_H$ (CDCl$_3$) 8.41 (1H, s), 7.73-7.66 (2H, m), 7.38-7.27 (1H, m), 4.81 (1H, m), 4.02 (1H, d, J=17.5 Hz), 3.88 (1H, d, J=17.5 Hz), 3.59-3.38 (4H, m), 2.93 (3H, br s), 1.69 (3H, d, J=6.7 Hz).

Intermediate 31

(S)-tert-Butyl 1-[8-chloro-2-(pyrrolidin-1-yl)quinolin-3-yl]ethylcarbamate

A mixture of Intermediate 11 (341 mg, 1 mmol), pyrrolidine (0.42 mL, 5 mmol) and DIPEA (0.84 mL, 5 mmol) in NMP (10 mL) was heated at 140° C. for 16 h. The reaction mixture was diluted with Et$_2$O (100 mL), washed with water (5×100 mL) and brine (100 mL), dried over MgSO$_4$ and filtered. The solvent was removed in vacuo and the residue purified by column chromatography on silica, eluting with 0-100% EtOAc in isohexane, to afford the title compound (120 mg, 32%) as a pale yellow solid. $\delta_H$ (CDCl$_3$) 7.87 (1H, s), 7.66-7.60 (1H, m), 7.56-7.49 (1H, m), 7.11 (1H, t, J=7.7 Hz), 5.31 (1H, d, J 12.5 Hz), 4.84 (1H, m), 3.85-3.76 (2H, m), 3.72 (2H, m), 2.09-1.95 (2H, m), 1.94 (2H, d, J=8.4 Hz), 1.52-1.32 (12H, m).

Intermediate 32

(S)-tert-Butyl 1-[8-chloro-2-(morpholin-4-yl)quinolin-3-yl]ethylcarbamate

Following the procedure described for Intermediate 31, Intermediate 11 (341 mg, 1 mmol), morpholine (0.44 mL, 5 mmol) and DIPEA (0.84 mL, 5 mmol) in NMP (10 mL) afforded the title compound (372 mg, 95%) as a pale yellow solid. $\delta_H$ (CDCl$_3$) 7.89 (1H, s), 7.62 (1H, dd, J 7.49, 1.40 Hz), 7.51 (1H, dd, J 7.95, 1.39 Hz), 7.15-7.05 (1H, m), 5.60-5.49 (1H, m), 4.42 (1H, d, J=6.89 Hz), 3.85-3.72 (5H, m), 3.39-3.36 (5H, m), 2.11-1.87 (10H, m).

Intermediate 33 tert-Butyl (S)-1-{8-chloro-2-[(R)-3-hydroxypyrrolidin-1-yl]quinolin-3-yl}ethylcarbamate Following the procedure described for Intermediate 31, Intermediate 11 (341 mg, 1 mmol), (R)-pyrrolidin-3-ol (261 mg, 3 mmol) and DIPEA (0.84 mL, 5 mmol) in NMP (8 mL) afforded the title compound (346 mg, 89%) as an off-white solid. $\delta_H$ (CDCl$_3$) 7.92 (1H, s), 7.64 (1H, dd, J 7.51, 1.39 Hz), 7.55 (1H, dd, J 8.01, 1.39 Hz), 7.20-7.11 (1H, m), 5.30 (1H, br s), 4.89 (1H, s), 4.60 (1H, s), 4.04-3.93 (2H, m), 3.75 (2H, d, J=12.47 Hz), 2.27 (1H, s), 2.19-2.05 (2H, m), 1.42-1.38 (12H, m).

Intermediate 34 tert-Butyl (S)-1-{8-chloro-2-[(S)-3-hydroxypyrrolidin-1-yl]quinolin-3-yl}ethylcarbamate Following the procedure described for Intermediate 31, Intermediate 11 (341 mg, 1 mmol), (S)-pyrrolidin-3-ol (261 mg, 3 mmol) and DIPEA (0.84 mL, 5 mmol) in NMP (8 mL) afforded the title compound (370 mg, 95%) as a pale yellow solid. $\delta_H$ (CDCl$_3$) 7.95 (1H, s), 7.66 (1H, dd, J 7.51, 1.37 Hz), 7.57 (1H, dd, J 8.04, 1.37 Hz), 7.27-7.16 (1H, m), 5.30 (1H, s), 4.89 (1H, s), 4.57 (1H, s), 4.16-4.03 (1H, m), 3.89 (1H, s), 3.75-3.66 (2H, m), 3.62 (1H, m), 2.25-2.14 (1H, m), 2.06-1.96 (1H, m), 1.50-1.42 (12H, m).

Intermediate 35

(S)-tert-Butyl 1-[8-chloro-2-(5-oxo-1,4]diazepan-1-yl)quinolin-3-ethylcarbamate

Following the procedure described for Intermediate 31, Intermediate 11 (341 mg, 1 mmol), [1,4]diazepan-5-one (148 mg, 1.3 mmol) and DIPEA (0.84 mL, 5 mmol) in NMP (8 mL) afforded the title compound (154 mg, 45%) as a pale yellow solid. $\delta_H$ (CDCl$_3$) 8.00 (1H, s), 7.71 (1H, dd, J 7.50, 1.34 Hz), 7.62 (1H, dd, J 8.1, 1.3 Hz), 7.31 (1H, t, J=7.8 Hz), 6.17 (1H, s), 5.09 (1H, s), 4.98 (1H, d, J=7.1 Hz), 3.77-3.47 (6H, m), 3.08-2.97 (1H, m), 2.92-2.81 (1H, m), 1.51-1.43 (12H, m).

Intermediate 36

(S)-tert-Butyl 1-[8-chloro-2-(4-methyl-3-oxopiperazin-1-yl)quinolin-3-yl]ethylcarbamate Following the procedure described for Intermediate 31, Intermediate 11 (341 mg, 1 mmol), 1-methyl-2-oxopiperazine (228 mg, 2 mmol) and DIPEA (0.84 mL, 5 mmol) in NMP (10 mL) afforded the title compound (240 mg, 57%) as a colourless foam. $\delta_H$ (CDCl$_3$) 8.02 (1H, s), 7.71 (1H, dd, J 7.5, 1.4 Hz), 7.62 (1H, dd, J 8.1, 1.4 Hz), 7.35-7.26 (1H, m), 5.10 (1H, s), 4.95 (1H, s), 4.30 (1H, d, J=17.3 Hz), 4.01 (1H, d, J 17.5 Hz), 3.94 (1H, s), 3.77-3.68 (1H, m), 3.43 (2H, m), 3.05 (3H, s), 1.51-1.43 (12H, m).

Intermediate 37

(S)-tert-Butyl 1-[8-chloro-2-(2-oxoimidazolidin-1-yl)quinolin-3-yl]ethylcarbamate To a degassed solution of Intermediate 11 (341 mg, 1 mmol) in 1,4-dioxane (100 mL) was added imidazolidin-2-one (430 mg, 5 mmol), caesium carbonate (488 mg, 1.5 mmol) palladium(II) acetate (11 mg, 0.05 mmol) and Xantphos (58 mg, 0.1 mmol) and the mixture was heated at 100° C. under nitrogen for 5 h. After cooling, the solvent was removed in vacuo and the residue partitioned between chloroform (80 mL) and NaHCO₃ solution (20 mL). The organic layer was separated, dried (MgSO₄), filtered and concentrated in vacuo. Purification by column chromatography on silica, eluting with 0-100% EtOAc in isohexane, afforded the title compound (175 mg, 44%) as a pale yellow foam. $\delta_H$ (CDCl₃) 8.20 (1H, s), 7.78-7.67 (2H, m), 7.37 (1H, t, J=7.8 Hz), 5.16 (1H, m), 5.11 (1H, m), 4.62 (1H, q, J=9.1 Hz), 4.13 (1H, m), 3.75-3.59 (2H, m), 1.74-1.61 (3H, m), 1.47-1.33 (9H, m).

Intermediate 38

(S)-1-[8-Chloro-2-(pyrrolidin-1-yl)quinolin-3-yl]ethanamine

Hydrogen chloride in 1,4-dioxane (4N; 4 mL) was added to Intermediate 31 (0.12 g, 0.32 mmol) and the solution was allowed to stand at r.t. overnight. The mixture was concentrated in vacuo and the residue purified by SCX column chromatography, eluting with MeOH, then 1M NH₃ in MeOH, to afford the title compound (88 mg, 100%) as a pale brown gum. $\delta_H$ (CDCl₃) 8.07 (1H, s), 7.63-7.58 (1H, m), 7.57-7.52 (1H, m), 7.15-7.06 (1H, m), 4.57 (1H, dd, J 12.8, 6.4 Hz), 3.78-3.67 (4H, m), 2.02-1.97 (4H, m), 1.64 (2H, br s), 1.52-1.41 (3H, m).

Intermediate 39

(S)-1-[8-Chloro-2-(morpholin-4-yl)quinolin-3-yl]ethanamine

Following the procedure described for Intermediate 38, Intermediate 32 (370 mg, 0.95 mmol) and 4N HCl in 1,4-dioxane (8 mL) afforded the title compound (228 mg, 83%) as a pale brown gum. $\delta_H$ (CDCl₃) 8.15 (1H, s), 7.69 (1H, dd J 7.5, 1.3 Hz), 7.63 (1H, dd, J 8.1, 1.4 Hz), 7.31-7.25 (1H, m) 4.50 (1H, q, J=6.5 Hz), 3.95-3.88 (4H, m), 3.47-3.34 (4H, m), 1.67 (2H, s), 1.50 (3H, d, J=6.5 Hz).

Intermediate 40

(R)-1-{3-[(S)-1-Aminoethyl]-8-chloroquinolin-2-yl}pyrrolidin-3-ol

To a solution of Intermediate 33 (147 mg, 0.38 mmol) in DCM (5 mL) was added TFA (2 mL) and the mixture was allowed to stand at r.t. overnight. The solvent was removed in vacuo and the residue purified by SCX column chromatography, eluting with MeOH, then 1M NH₃ in MeOH, to afford the title compound (110 mg, 100%) as a pale orange oil. $\delta_H$ (CDCl₃) 8.09 (1H, s), 7.67-7.60 (1H, m), 7.57 (1H, dd, J 8.0, 1.4 Hz), 7.23-7.14 (1H, m), 4.62-4.53 (2H, m), 3.94 (1H, d, J=12.2 Hz), 3.88-3.74 (1H, m), 3.74-3.64 (2H, m), 2.19-1.98 (5H, m), 1.52-1.42 (3H, m).

Intermediate 41

(S)-1-{3-[(S)-1-Aminoethyl]-8-chloroquinolin-2-yl}pyrrolidin-3-ol

Following the procedure described for Intermediate 40, Intermediate 34 (157 mg, 0.40 mmol) and TFA (2 mL) in DCM (5 mL) afforded the title compound (110 mg, 94%) as a pale orange gum. $\delta_H$ (CDCl₃) 8.08 (1H, s), 7.64 (1H, dd, J 7.5, 1.4 Hz), 7.56 (1H, dd, J 8.0, 1.4 Hz), 7.23-7.12 (1H, m), 4.59-4.53 (2H, m), 3.94-3.75 (3H, m), 3.70-3.57 (1H, m), 2.30 (1H, br s), 2.20-1.98 (3H, m), 1.50-1.43 (3H, m).

Intermediate 42

(S)-1-[3-(1-Aminoethyl)-8-chloroquinolin-2-yl]-[1,4]diazepan-5-one

Following the procedure described for Intermediate 40, Intermediate 35 (154 mg, 0.37 mmol) and TFA (2 mL) in DCM (5 mL) afforded the title compound (111 mg, 95%) as a pale orange gum. $\delta_H$ (CDCl₃) 8.19 (1H, s), 7.70 (1H, dd, J 7.5, 1.3 Hz), 7.64 (1H, dd, J 8.0, 1.3 Hz), 7.34-7.23 (1H, m), 6.49 (1H, s), 4.46 (1H, q, J=6.5 Hz), 3.65-3.50 (6H, m), 2.91 (2H, t, J=5.2 Hz), 1.49 (3H, d, J=6.5 Hz).

Intermediate 43

(S)-4-(3-(1-Aminoethyl)-8-chloroquinolin-2-yl)-1-methylpiperazin-2-one

Following the procedure described for Intermediate 40, Intermediate 36 (240 mg, 0.57 mmol) and TFA (2 mL) in DCM (5 mL) afforded the title compound (166 mg, 91%) as a colourless gum. $\delta_H$ (CDCl₃) 8.21 (1H, s), 7.70 (1H, dd, J 7.5, 1.4 Hz), 7.64 (1H, dd, J 8.1, 1.4 Hz), 7.34-7.23 (1H, m), 4.49 (1H, dd, J 12.9, 6.5 Hz), 4.20-3.96 (2H, m), 3.82-3.55 (4H, m), 3.04 (3H, s), 1.49 (3H, d, J=6.5 Hz).

Intermediate 44

(S)-1-[3-(1-Aminoethyl)-8-chloroquinolin-2-yl]imidazolidin-2-one

Following the procedure for Intermediate 40, Intermediate 37 (174 mg, 0.45 mmol) and TFA (2 mL) in DCM (5 mL) afforded the title compound (108 mg, 83%) as a colourless gum. $\delta_H$ (CDCl₃) 8.40 (1H, s), 7.78-7.65 (3H, m), 7.46-7.30 (1H, m), 5.51 (1H, s), 4.76-4.63 (2H, m), 4.05 (1H, m), 3.72-3.60 (3H, m), 1.41 (3H, dd, J 11.4, 6.6 Hz).

Intermediate 45

(S)-N-[1-(2-Chloro-8-methylquinolin-3-yl)ethyl]-2,2,2-trifluoroacetamide

Intermediate 3 (500 mg, 2.26 mmol) and trifluoroacetic anhydride (1 mL, 4.50 mmol) in DCM (5 mL) were stirred overnight. The mixture was diluted with DCM (20 mL) and washed with aqueous NaOH (10 mL; 1M). The organic layer was dried (MgSO₄), filtered and the solvent was removed in vacuo to give the title compound (615 mg, 85%) as an off-white solid. LCMS (ES+) 317 (M+H)+.

Intermediate 46

(S)-N-(1-{2-[4-Cyclopropanecarbonyl)piperazin-1-yl]-8-methylquinolin-3-yl}ethyl)-2,2,2-trifluoroacetamide Intermediate 45 (100 mg, 0.32 mmol), cyclopropyl(piperazin-1-yl)methanone (0.09 mL, 0.63 mmol), NMP (2 mL) and DIPEA (0.10 mL, 0.80 mmol) were combined in a sealed tube and heated to 140° C. for 4 days. After cooling, Et$_2$O (50 mL) was added to the reaction mixture. The organic layer was washed with water (5×50 mL) and brine. The organic layer was dried (MgSO$_4$), filtered and the solvent was removed in vacuo. Purification by column chromatography on silica, eluting with 0-30% EtOAc in isohexane, gave the title compound (82 mg, 60%) as a pale yellow gum. δ$_H$ (CDCl$_3$) 8.01 (1H, s), 7.75-7.65 (1H, m), 7.59 (1H, d, J=8.1 Hz), 7.55-7.48 (1H, m), 7.40-7.31 (1H, m), 5.58-5.47 (1H, m), 4.00-3.86 (3H, m), 3.85-3.72 (1H, s), 3.54-3.30 (2H, m), 3.18 (2H, m), 2.71 (3H, s), 1.84-1.76 (1H, m), 1.64 (3H, d, J=6.8 Hz), 1.09-0.97 (2H, m), 0.84-0.75 (2H, Intermediate 47

(S)-{4-[3-(1-Aminoethyl)-8-methylquinolin-2-yl]piperazin-1-yl}(cyclopropyl)methanone Intermediate 46 (82 mg, 0.19 mmol) was dissolved in MeOH (5 mL). Saturated aqueous K$_2$CO$_3$ solution (5 mL) was added and the mixture was stirred overnight. Solid K$_2$CO$_3$ (500 mg) was added and the mixture stirred for 2 more days. The solvent was removed in vacuo and the residue was dissolved in DCM and washed with water. The organic layer was passed through a phase separating cartridge. The solvent was removed in vacuo to give the title compound (62 mg, 97%) as a yellow foam. δ$_H$ (CDCl$_3$) 8.12 (1H, s), 7.58 (1H, d, J=8.1 Hz), 7.45 (1H, d, J=7.0 Hz), 7.34-7.24 (1H, m), 4.57-4.48 (1H, m), 3.99-3.77 (4H, m), 3.39 (2H, br s), 3.28 (2H, br s), 2.70 (3H, s), 1.86-1.77 (1H, m), 1.75-1.58 (2H, br s), 1.51 (3H, d, J=6.5 Hz), 1.08-0.98 (2H, m), 0.91-0.73 (2H, m).

Intermediate 48

(S)-tert-Butyl 1-{8-chloro-2-[4-(cyclopropanecarbonyl)piperazin-1-yl]quinolin-3-yl}ethylcarbamate Intermediate 11 (150 mg, 0.44 mmol), cyclopropyl(piperazin-1-yl)methanone (0.16 mL, 1.1 mmol), NMP (2 mL) and DIPEA (0.38 mL, 2.2 mmol) were combined in a sealed tube and heated to 140° C. for 36 h. After cooling, Et$_2$O was added to the reaction mixture. The organic layer was washed with water and brine. The organic layer was dried (MgSO$_4$), filtered and the solvent was removed in vacuo. Purification by column chromatography on silica, eluting with 0-5% MeOH in EtOAc, gave the title compound (175 mg, 86%) as a yellow gum. δ$_H$ (CDCl$_3$) 8.00 (1H, s), 7.71 (1H, dd, J 7.5, 1.3 Hz), 7.62 (1H, dd, J 8.1, 1.3 Hz), 7.34-7.28 (1H, m), 5.15 (1H, br s), 4.95 (1H, br s), 3.86 (4H, br s), 3.60 (2H, br s), 3.34 (2H, br s), 1.85-1.77 (1H, m), 1.46 (3H, s), 1.44 (9H, s), 1.05-1.00 (2H, m), 0.80 (2H, dd, J 7.8, 3.5 Hz). LCMS (ES+) 459 (M+H)+.

Intermediate 49

(S)-{4-[3-(1-Aminoethyl)-8-chloroquinolin-2-yl]piperazin-1-yl}(cyclopropyl)methanone Intermediate 48 (175 mg, 0.38 mmol) was dissolved in DCM (4 mL). TFA (3 mL) was added and the resulting solution was stirred for 2 h. The solvents were removed in vacuo. The residue was dissolved in DCM (25 mL) and washed with 1M NaOH (5 mL). The organic layer was passed through a phase separator and the solvent removed in vacuo to give the title compound (130 mg, 95%) as a yellow gum. δ$_H$ (CDCl$_3$) 8.19 (1H, s), 7.70 (1H, dd, J 7.8, 1.3 Hz), 7.64 (1H, dd, J 8.0, 1.3 Hz), 7.34-7.25 (1H, m), 4.54 (1H, q, J=6.5 Hz), 3.94 (2H, br s), 3.84 (2H, br s), 3.50 (2H, br s), 3.34 (2H, br s), 2.13 (2H, br s), 1.85-1.77 (1H, m), 1.52 (3H, d, J=6.5 Hz), 1.05-0.96 (2H, m), 0.87-0.76 (2H, m).

Intermediate 50

(S)-tert-Butyl 1-(2-{4-[2-(dimethylamino)-2-oxoethyl]piperazin-1-yl}-8-methylquinolin-3-yl)ethylcarbamate Following the procedure described for Intermediate 31, Intermediate 4 (150 mg, 0.47 mmol), NMP (1 mL), DIPEA (0.41 mL, 2.34 mmol) and N,N-dimethyl-2-(piperazin-1-yl)acetamide (161 mg, 0.94 mmol), with subsequent purification by preparative HPLC, gave the title compound (133 mg, 62%) as a yellow gum. LCMS (ES+) 456 (M+H)+.

Intermediate 51

(S)-2-{4-[3-(1-Aminoethyl)-8-methylquinolin-2-yl]piperazin-1-yl}-N,N-dimethyl-acetamide Following the procedure described for Intermediate 30, Intermediate 50 (133 mg, 0.29 mmol), TFA (3 mL) and DCM (4 mL) gave the title compound (100 mg, 96%) as a yellow gum. δ$_H$ (CDCl$_3$) 8.08 (1H, s), 7.55 (1H, d, J=8.1 Hz), 7.43 (1H, d, J=7.0 Hz), 7.27 (1H, t, J 7.9 Hz), 4.53 (1H, dd, J 13.1, 6.5 Hz), 3.33 (4H, dd, J 6.8, 3.5 Hz), 3.27 (2H, s), 3.13 (3H, s), 2.96 (3H, s), 2.76 (4H, t, J=5.7 Hz), 2.70 (3H, s), 2.44 (2H, br s), 1.51 (3H, d, J=6.5 Hz).

Intermediate 52

(S)-tert-Butyl 1-(8-methyl-2-{4-[2-(morpholin-4-yl)-2-oxoethyl]piperazin-1-yl}quinolin-3-yl)ethylcarbamate Following the procedure described for Intermediate 31, Intermediate 4 (150 mg, 0.47 mmol), NMP (1 mL), DIPEA (0.41 mL, 2.34 mmol) and 1-(morpholin-4-yl)-2-(piperazin-1-yl)ethanone (200 mg, 0.94 mmol), with subsequent purification by preparative HPLC, gave the title compound (182 mg, 78%) as a yellow gum. δ$_H$ (CDCl$_3$) 8.15 (1H, s), 7.94 (1H, s), 7.54 (1H, d, J=8.1 Hz), 7.45 (1H, d, J=7.0 Hz), 7.33-7.27 (1H, m), 5.12-5.06 (1H, m), 3.75-3.61 (8H, m), 3.39 (2H, s), 2.88-2.83 (8H, m), 2.70 (3H, s), 1.45 (3H, s), 1.43 (9H, s). LCMS (ES+) 498 (M+H)+.

Intermediate 53

(S)-2-{4-[3-(1-Aminoethyl)-8-methylquinolin-2-yl]piperazin-1-yl}-1-(morpholin-4-yl)-ethanone bis hydrochloric acid salt Intermediate 52 (170 mg, 0.34 mmol) was dissolved in MeOH (3 mL). HCl (2M in Et$_2$O; 3 mL) was added and the mixture was stirred overnight. The solvents were removed in vacuo to give the title compound (147 mg, 100%) as a pale yellow solid. $\delta_H$ (DMSO-$d_6$) 10.16 (1H, s), 8.61-8.56 (3H, m), 7.76 (1H, d, J=8.1 Hz), 7.65 (1H, d, J=7.0 Hz), 7.49-7.44 (1H, m), 4.71 (1H, s), 4.50 (2H, s), 3.80-3.39 (16H, m), 2.71 (3H, s), 1.68 (3H, d, J=6.6 Hz).

Intermediate 54

(S)-tert-Butyl 1-{8-chloro-2-[4-(methylsulfonyl) piperazin-1-yl]quinolin-3-yl}ethyl-carbamate Following the procedure described for Intermediate 31, Intermediate 11 (255 mg, 0.75 mmol), NMP (5 mL), DIPEA (0.39 mL, 2.24 mmol) and 1-(methylsulfonyl)-piperazine (363 mg, 2.24 mmol) gave the title compound (229 mg, 65%) as a yellow gum. $\delta_H$ (CDCl$_3$) 8.00 (1H, s), 7.72 (1H, dd, J 7.5, 1.3 Hz), 7.63 (1H, dd, J 8.1, 1.3 Hz), 7.33-7.24 (1H, m), 5.12 (1H, br s), 4.92 (1H, br s), 3.75-3.67 (2H, m), 3.62-3.55 (2H, m), 3.44-3.37 (4H, m), 2.85 (3H, s), 1.47-1.43 (12H, m).

Intermediate 55

(S)-1-{8-Chloro-2-[4-(methylsulfonyl)piperazin-1-yl]quinolin-3-yl}ethanamine

Intermediate 54 (228 mg, 0.49 mmol) was dissolved in DCM (6 mL). TFA (4 mL) was added and the mixture was stirred for 1 h. The solvents were removed in vacuo and the resulting gum was passed through a SCX cartridge, eluting with 0-0.1M MeOH/NH$_3$ in MeOH. The solvent was removed in vacuo to give the title compound (170 mg, 96%) as a colourless gum. $\delta_H$ (CDCl$_3$) 8.18 (1H, s), 7.71 (1H, dd, J 7.5, 1.3 Hz), 7.64 (1H, dd, J 8.1, 1.3 Hz), 7.31 (1H, t, J=7.8 Hz), 4.46 (1H, dd, J 13.0, 6.5 Hz), 3.62-3.52 (4H, m), 3.52-3.45 (4H, m), 2.84 (3H, s), 1.50 (3H, d, J=6.5 Hz).

Intermediate 56

(S)-Ethyl 2-(4-{3-[1-(tert-butoxycarbonylamino) ethyl]-8-chloroquinolin-2-yl}piperazin-1-yl)acetate Following the procedure described for Intermediate 31, Intermediate 11 (150 mg, 0.44 mmol), NMP (2 mL), DIPEA (0.38 mL, 2.2 mmol) and ethyl 2-(piperazin-1-yl)acetate (189 mg, 1.10 mmol) gave the title compound (116 mg, 55%) as a yellow gum. $\delta_H$ (CDCl$_3$) 7.95 (1H, s), 7.68 (1H, dd, J 7.5, 1.3 Hz), 7.59 (1H, dd, J 8.1, 1.4 Hz), 7.27 (1H, t, J=7.84 Hz), 5.11 (1H, br s), 4.96 (1H, br s), 4.22 (2H, dd, J 14.3, 7.1 Hz), 3.67 (2H, d, J=11.3 Hz), 3.39-3.28 (2H, m), 3.32 (2H, s), 2.92-2.85 (2H, m), 2.83-2.74 (2H, m), 1.44 (9H, s), 1.43 (3H, s), 1.30 (3H, t, J=7.1 Hz). LCMS (ES+) 377 (M+H)$^+$.

Intermediate 57

(S)-Ethyl 2-{4-[3-(1-aminoethyl)-8-chloroquinolin-2-yl]piperazin-1-yl}acetate bis hydrochloride salt Following the procedure described for Intermediate 53, Intermediate 56 (232 mg, 0.50 mmol), MeOH (5 mL) and 2N HCl in Et$_2$O (4 mL) gave the title compound (240 mg, 100%) as a yellow gum. $\delta_H$ (MeOD-$d_4$) 8.54 (1H, s), 7.95-7.87 (2H, m), 7.57-7.49 (1H, m), 4.43-4.33 (3H, m), 3.91-3.79 (6H, m), 3.71-3.48 (2H, m), 3.35 (2H, under MeOH), 1.83 (3H, d, J=6.7 Hz), 1.37 (3H, t, J 7.20 Hz).

Intermediate 58

(S)-tert-Butyl 1-(8-chloro-2-{4-[2-(dimethylamino)-2-oxoethyl]piperazin-1-yl}quinolin-3-yl)ethylcarbamate Following the procedure described for Intermediate 31, Intermediate 11 (150 mg, 0.44 mmol), NMP (2 mL), DIPEA (0.38 mL, 2.2 mmol) and N,N-dimethyl-2-(piperazin-1-yl) acetamide (188 mg, 2.50 mmol) gave the title compound (165 mg, 79%) as a yellow gum. $\delta_H$ (CDCl$_3$) 7.96 (1H, s), 7.68 (1H, dd, J 7.5, 1.3 Hz), 7.60 (1H, dd, J 8.1, 1.3 Hz), 7.28 (1H, dd, J 8.1, 7.5 Hz), 5.10 (1H, br s), 4.98 (1H, br s), 3.64 (2H, br s), 3.39-3.18 (2H, m), 3.32 (2H, s), 3.15 (3H, s), 2.97 (3H, s), 2.86-2.77 (2H, m), 2.76-2.68 (2H, m), 1.44 (9H, s), 1.42 (3H, s).

Intermediate 59

(S)-2-{4-[3-(1-Aminoethyl)-8-chloroquinolin-2-yl] piperazin-1-yl}-N,N-dimethyl-acetamide Following the procedure described for Intermediate 55, Intermediate 58 (165 mg, 0.35 mmol), TFA (3 mL) and DCM (4 mL) gave the title compound (126 mg, 95%) as a yellow gum. $\delta_H$ (CDCl$_3$) 8.13 (1H, s), 7.68 (1H, dd, J 7.5, 1.3 Hz), 7.62 (1H, dd, J 8.1, 1.3 Hz), 7.26 (1H, t, J=8.3 Hz), 4.50 (1H, dd, J 12.9, 6.5 Hz), 3.48-3.36 (4H, m), 3.28 (2H, s), 3.14 (3H, s), 2.97 (3H, s), 2.79-2.73 (4H, m), 1.66 (2H, br s), 1.48 (3H, d, J=6.5 Hz).

Intermediate 60

[8-Methyl-2-(pyrrolidin-1-yl)quinolin-3-yl]methanol (2-Chloro-8-methylquinolin-3-yl)methanol (200 mg, 0.97 mmol) and pyrrolidine (2 mL) were stirred in a sealed tube at 100° C. for 4 h. After cooling, the solution was diluted with EtOAc and washed with water and brine. The organic layer was dried (MgSO$_4$), filtered and the solvent was removed in vacuo. Purification by column chromatography on silica, eluting with 20% EtOAc in isohexane, gave the title compound (206 mg, 88%). $\delta_H$ (CDCl$_3$) 7.86 (1H, s), 7.46 (1H, d, J=8.01 Hz), 7.40 (1H, d, J=7.04 Hz), 7.13 (1H, t, J=7.50 Hz), 4.85 (2H, s), 3.72 (4H, t, J=6.36 Hz), 2.65 (3H, s), 2.12 (1H, s), 2.03-1.96 (4H, m).

Intermediate 61

[8-Methyl-2-(morpholin-4-yl)quinolin-3-yl]methanol

Following the procedure described for Intermediate 60, (2-chloro-8-methyl-quinolin-3-yl)methanol (200 mg, 0.97 mmol) and morpholine (2 mL) gave the title compound (200 mg, 80%). $\delta_H$ (CDCl$_3$) 7.99 (1H, s), 7.57 (1H, d, J=8.1 Hz), 7.48 (1H, d, J=7.0 Hz), 7.35-7.26 (1H, m), 4.87 (2H, s), 3.93 (4H, t, J=4.6 Hz), 3.58 (1H, s), 3.35 (4H, t, J=4.6 Hz), 2.72 (3H, s).

Intermediate 62

(2-Chloro-8-methylquinolin-3-yl)methanamine

2-Chloro-8-methylquinoline-3-carboxaldehyde (5 g, 24.6 mmol) in dry THF (75 mL) was treated with titanium(IV) isopropoxide (14.5 mL, 48 mmol). After 5 minutes, (R)-(−)-2-methyl-2-propanesulfinamide (2.95 g, 24 mmol) was added in one portion and the mixture was stirred for 60 h. The mixture was cooled to 0° C. in a water/ice bath and NaBH$_4$ (1.9 g, 48 mmol) was added. The mixture was stirred for 3 h and cooled to 10° C. MeOH (20 mL) was added dropwise, followed by water (5 mL). The resulting slurry was filtered through Celite and washed thoroughly with EtOAc. The organic layer was washed with water and brine, dried (MgSO$_4$) and the solvent removed in vacuo. The residue was dissolved in MeOH (20 mL) and HCl (4M in 1,4-dioxane; 30 mL). The mixture was stirred for 2 h and, after removing the solvent in vacuo, the residue was dissolved in DCM. The organic layer was washed with sat. NaHCO$_3$ solution, water and brine, then dried (MgSO$_4$), filtered and the solvent removed in vacuo. The residue was redissolved in MeOH and passed through an SCX cartridge, eluting with 0-0.1M MeOH/NH$_3$ in MeOH. The solvent was removed in vacuo and the residue purified by column chromatography on silica, eluting with 0-5% MeOH in EtOAc, to afford the title compound (3 g, 60%). $\delta_H$ (DMSO-d$_6$) 8.50 (1H, s), 7.89 (1H, d, J=8.1 Hz), 7.67 (1H, d, J=7.0 Hz), 7.57 (1H, t, J=7.6 Hz), 4.00 (2H, s), 2.70 (3H, s).

Intermediate 63 tert-Butyl (2-chloro-8-methylquinolin-3-yl)methylcarbamate

To a solution of Intermediate 62 (3 g, 14.6 mmol) in DCM (60 mL) was added di-tert-butyl dicarbonate (3.5 g, 16 mmol) in one portion and the mixture was stirred overnight. DIPEA (2.54 mL, 14.6 mmol) was added and the mixture was stirred for a further 6 h. Solvents were removed in vacuo and the residue was triturated with Et$_2$O to give the title compound (3.5 g, 78%). $\delta_H$ (CDCl$_3$) 8.12 (1H, s), 7.66 (1H, d, J=8.1 Hz), 7.56 (1H, d, J 7.0 Hz), 7.44 (1H, t, J=7.6 Hz), 5.20 (1H, br s), 4.52 (2H, d, J=6.5 Hz), 2.76 (3H, s), 1.45 (9H, s). LCMS (ES+) 307 (M+H)$^+$, RT 3.88 minutes (Method 1).

Intermediate 64 tert-Butyl[8-methyl-2-(3-oxopiperazin-1-yl)quinolin-3-yl]methylcarbamate

Intermediate 63 (500 mg, 1.6 mmol), 2-oxopiperazine (820 mg, 8.2 mmol), NMP (8 mL) and DIPEA (1.4 mL, 8.2 mmol) were combined in a sealed tube and heated to 130° C. for 36 h. After cooling, Et$_2$O was added to the reaction mixture and the organic layer was washed with water and brine. The organic layer was dried (MgSO$_4$), filtered and the solvent was removed in vacuo. Purification by column chromatography on silica, eluting with EtOAc, gave the title compound (405 mg, 67%) as a yellow gum. $\delta_H$ (CDCl$_3$) 8.00 (1H, s), 7.57 (1H, d, J=8.1 Hz), 7.48 (1H, d, J=7.1 Hz), 7.35-7.24 (1H, m), 6.10 (1H, s), 5.06 (1H, s), 4.51 (2H, d, J=6.1 Hz), 4.16-4.05 (2H, m), 3.50 (4H, s), 2.69 (3H, s), 1.49 (9H, s). LCMS (ES+) 371 (M+H)$^+$, RT 3.26 minutes (Method 2).

Intermediate 65

4-[3-(Aminomethyl)-8-methylquinolin-2-yl]piperazin-2-one

To a solution of Intermediate 64 (390 mg, 1.1 mmol) in DCM (3 mL) was added TFA (3 mL) and the mixture was stirred for 1 h. The solvents were removed in vacuo and the residue was redissolved in MeOH and passed through a SCX cartridge, eluting with 0-0.1M MeOH/NH$_3$ in MeOH. The solvent was removed in vacuo to give the title compound (280 mg, 98%). $\delta_H$ (CDCl$_3$) 8.09 (1H, s), 7.58 (1H, d, J=8.1 Hz), 7.47 (1H, d, J 7.1 Hz), 7.31 (1H, t, J=7.6 Hz), 5.96 (1H, s), 4.13 (2H, s), 4.05 (2H, s), 3.62-3.49 (4H, m), 2.70 (3H, s), 1.56 (2H, s). LCMS (ES+) 270 (M+H)$^+$, RT 2.17 minutes (Method 1).

Intermediate 66

(S)-tert-Butyl 1-[2-(4-acetylpiperazin-1-yl)-8-methylquinolin-3-yl]ethylcarbamate Intermediate 4 (150 mg, 0.47 mmol), 1-acetylpiperazine (300 mg, 2.34 mmol), DIPEA (0.42 mL, 2.34 mmol) and NMP (3 mL) were combined in a sealed tube and heated to 140° C. for 48 h. After cooling, the reaction mixture was dissolved in a 1:1 mixture of EtOAc and Et$_2$O (100 mL) and washed with saturated brine (3×25 mL). The organic layer was dried (MgSO$_4$) and concentrated in vacuo. Purification by column chromatography on silica, eluting with 0-100% EtOAc in isohexane, afforded the title compound (151 mg, 78%) as a white solid. LCMS (ES+) 413 (M+H)$^+$.

Intermediate 67

(S)-1-{4-[3-(1-Aminoethyl)-8-methylquinolin-2-yl]piperazin-1-yl}ethanone

Intermediate 66 (151 mg, 0.37 mmol) was dissolved in DCM (3 mL) and TFA (2 mL) and the reaction mixture was stirred at r.t. for 2 h. The solvent was removed in vacuo and the resulting oil was azeotroped with toluene (3×20 mL). The residue was dissolved in DCM and passed through a SCX column, eluting with 50% DCM in MeOH, then 0.7M NH$_3$ in MeOH, to give the title compound (100 mg, 87%) as a yellow gum. LCMS (ES+) 313 (M+H)$^+$.

Intermediate 68

4-[3-(Hydroxymethyl)-8-methylquinolin-2-yl]piperazin-2-one (2-Chloro-8-methylquinolin-3-yl)methanol (250 mg, 1.13 mmol), 2-oxopiperazine (566 mg, 5.66 mmol), DIPEA (1 mL, 5.66 mmol) and NMP (3 mL) were combined in a sealed tube and heated to 140° C. for 24 h. After cooling, the reaction mixture was dissolved in a 1:1 mixture of EtOAc and Et$_2$O (100 mL) and washed with saturated brine (3×25 mL). The organic layer was dried (MgSO$_4$) and concentrated in vacuo. Purification by column chromatography on silica, eluting with 5% MeOH in DCM, afforded the title compound (155 mg, 51%) as a white solid. LCMS (ES+) 272 (M+H)$^+$.

Intermediate 69

(S)-1-[8-Chloro-2-(3,3-difluoropyrrolidin-1-yl)quinolin-3-yl]ethanamine

A mixture of Intermediate 11 (0.341 g, 1.00 mmol), 3,3-difluoropyrrolidine hydrochloride (0.431 g, 3.00 mmol) and DIPEA (0.84 mL, 5.00 mmol) in NMP (10 mL) was heated at 140° C. for 16 h. After cooling, Et$_2$O (250 mL) was added and the mixture was washed with water (3×100 mL) and brine (100 mL). The organic layer was separated, dried (MgSO$_4$), concentrated in vacuo and the residue purified by column chromatography (SiO$_2$, 0-100% EtOAc in isohexane) to afford a pale brown solid (0.236 g, 57%). LCMS (ES+) 412

(M+H)⁺. This solid was dissolved in a mixture of DCM (10 mL) and TFA (4 mL), and the reaction mixture was stirred at r.t. for 3 h. The solvent was removed in vacuo, and the residue was dissolved in DCM-MeOH (1:1) and passed through an SCX cartridge, washing with MeOH (100 mL) and eluting with 1M NH₃ in MeOH (30 mL). The eluate was concentrated in vacuo to afford the title compound (152 mg, 85%) as a pale brown gum. $\delta_H$ (CDCl₃) 8.18 (1H, s), 7.69-7.59 (2H, m), 7.27-7.17 (1H, m), 4.47 (1H, q, J=6.45 Hz), 4.12-3.84 (4H, m), 2.55-2.41 (2H, m), 1.49 (3H, d, J=6.46 Hz), NH₂ exchanging. LCMS (ES+) 312 (M+H)⁺.

Intermediate 70

(S)-1-{8-Chloro-2-[(R)-3-fluoropyrrolidin-1-yl]quinolin-3yl}ethanamine

Following the procedure described for Intermediate 69, Intermediate 11 (0.341 g, 1.00 mmol), S-(+)-3-fluoropyrrolidine hydrochloride (0.628 g, 5.00 mmol) and DIPEA (0.84 mL, 5.00 mmol) in NMP (10 mL) afforded a pale cream solid (0.238 g, 60%). LCMS (ES+) 394 (M+H)⁺. This solid was dissolved in a mixture of DCM (10 mL) and TFA (4 mL), and the reaction mixture was stirred at r.t. for 3 h. The solvent was removed in vacuo and the residue dissolved in DCM-MeOH (1:1) and passed through an SCX cartridge, washing with MeOH (100 mL) and eluting with 1M NH₃ in MeOH (30 mL). The eluate was concentrated in vacuo to afford the title compound (168 mg, 95%) as a pale brown gum. $\delta_H$ (CDCl₃) 8.08 (1H, s), 7.65 (1H, dd, J 7.52, 1.37 Hz), 7.57 (1H, dd, J 8.02, 1.36 Hz), 7.17 (1H, t, J 7.77 Hz), 5.50-5.43 (1H, m), 5.36-5.29 (1H, m), 4.55 (1H, q, J=6.43 Hz), 4.25 (1H, dd, J 13.12, 3.81 Hz), 4.19-4.03 (2H, m), 3.90-3.80 (1H, m,), 3.73-3.66 (1H, m), 2.42-2.31 (1H, m), 2.26-2.05 (1H, m), 1.57 (3H, d, J=6.44 Hz). LCMS (ES+) 294 (M+H)⁺.

Intermediate 71

(S)-1-{8-Chloro-2-[(S)-3-fluoropyrrolidin-1-yl]quinolin-3-yl}ethanamine

Following the procedure described for Intermediate 69, Intermediate 11 (0.341 g, 1.00 mmol), R-(−)-3-fluoropyrrolidine hydrochloride (0.628 g, 5.00 mmol) and DIPEA (0.84 mL, 5.00 mmol) in NMP (10 mL) afforded a pale cream solid (0.264 g, 67%). LCMS (ES+) 394 (M+H)⁺. This solid was dissolved in a mixture of DCM (10 mL) and TFA (4 mL), and the reaction mixture was stirred at r.t. for 3 h. The solvent was removed in vacuo, and the residue was dissolved in DCM-MeOH (1:1) and passed through an SCX cartridge, washing with MeOH (100 mL) and eluting with 1M NH₃ in MeOH (30 mL). The eluate was concentrated in vacuo to afford the title compound (165 mg, 84%) as a pale brown gum. $\delta_H$ (CDCl₃) 8.17 (1H, s), 7.66-7.56 (2H, m), 7.16 (1H, t, J 7.76 Hz), 5.46 (1H, t, J=3.72 Hz), 5.32 (1H, t, J=3.73 Hz), 4.57 (1H, q, J=6.47 Hz), 4.20 (1H, dd, J 13.23, 3.73 Hz), 4.13-3.85 (3H, m), 3.81-3.74 (1H, m), 2.42-2.31 (1H, m), 2.24-2.02 (1H, m), 1.38 (3H, d, J=6.47 Hz). LCMS (ES+) 294 (M+H)⁺.

Intermediate 72

(S)-4-[3-(1-Aminoethyl)-8-chloroquinolin-2-yl]-N,N-dimethylpiperazine-1-carboxamide hydrochloride salt Intermediate 11 (150 mg, 0.44 mmol), N,N-dimethylpiperazine-1-carboxamide (173 mg, 1.1 mmol), NMP (2 mL) and DIPEA (0.38 mL, 2.2 mmol) were combined in a sealed tube and heated to 140° C. for 36 h. After cooling, Et₂O (50 mL) was added to the reaction mixture. The organic layer was washed with water (4×20 mL) and brine (20 mL). The organic layer was separated, dried (MgSO₄), filtered and concentrated in vacuo. Purification by column chromatography (SiO₂, 0-5% MeOH in EtOAc) gave a yellow gum (128 mg, 63%). This material was dissolved in MeOH (3 mL) and HCl (2N solution in Et₂O, 3 mL) was added. The reaction mixture was stirred at r.t. for 16 h. The solvent was removed in vacuo to afford the title compound (110 mg, quantitative) as an off-white solid. LCMS (ES+) 362 (M+H)⁺.

Intermediate 73

(S)-1-{4-[3-(1-Aminoethyl)-8-chloroquinolin-2-yl]-[1,4]diazepan-1-yl}ethanone

Following the procedure described for Intermediate 72, Intermediate 11 (150 mg, 0.44 mmol), 1-([1,4]diazepan-1-yl)ethanone (0.051 mL, 1.1 mmol) and DIPEA (0.38 mL, 2.2 mmol) in NMP (2 mL) gave a yellow gum (154 mg, 78%). This material was dissolved in DCM (4 mL) and TFA (2 mL) was added. The reaction mixture was stirred at r.t. for 2 h. The solvent was removed in vacuo, and the residue was dissolved in DCM-MeOH (1:1) and passed through an SCX cartridge, washing with MeOH (100 mL) and eluting with 1M NH₃ in MeOH (30 mL). The eluate was concentrated in vacuo to afford the title compound (100 mg, 84%) as a pale yellow gum. $\delta_H$ (CDCl₃) 8.16 (1H, d, J=6.85 Hz), 7.71-7.59 (2H, m), 7.24-7.22 (1H, m), 4.46 (1H, q, J=6.46 Hz), 4.05-3.76 (3H, m), 3.72-3.46 (5H, m), 2.17-2.08 (4H, m), 2.04-1.87 (1H, m), 1.48 (3H, dd, J 6.44, 1.14 Hz), NH₂ exchanging. LCMS (ES+) 346 (M+H)⁺.

Intermediate 74

(S)-tert-Butyl 1-[7-fluoro-8-methyl-2-(pyrrolidin-1-yl)quinolin-3-yl]ethylcarbamate To a solution of Intermediate 27 (280 mg, 0.83 mmol) in n-butanol (3 mL) were added pyrrolidine (0.20 mL, 2.33 mmol) and DIPEA (0.42 mL, 2.33 mmol). The resulting solution was heated at 120° C. for 16 h. The mixture was diluted with EtOAc (50 mL) and Et₂O (50 mL) and washed with brine (3×25 mL). The organic layer was separated, dried (MgSO₄), filtered and the solvent removed in vacuo. Purification by column chromatography (SiO₂, 5-10% Et₂O in petrol 40-60) gave the title compound (270 mg, 87%) as a pale yellow oil. LCMS (ES+) 375 (M+H)⁺.

Intermediate 75

(S)-2-{4-[3-(1-Aminoethyl)-8-chloroquinolin-2yl]piperazin-1-yl}ethanol bis hydrochloride salt Intermediate 11 (700 mg, 2.05 mmol), 1-(2-hydroxyethyl)piperazine (1 mL), n-butanol (6 mL) and DIPEA (1 mL) were combined in a sealed tube and heated to 120° C. for 4 days. The reaction mixture was cooled, concentrated onto silica and purified by column chromatography (SiO₂, 0-100% EtOAc in isohexane) to give a clear gum (681 mg, 76%). This gum (670 mg, 1.54 mmol), MeOH (5 mL) and HCl (2N in Et₂O, 5 mL) were combined and stirred at r.t. for 24 h. The reaction mixture was concentrated to give the title compound (670 mg, quantitative) as a yellow solid. LCMS (ES+) 375 (M+H)⁺.

Intermediate 76

(S)-tert Butyl 1-{7-fluoro-2-[4-(2-hydroxyacetyl)piperazin-1-yl]-8-methylquinolin-3-yl}ethylcarbamate Intermediate 27 (500 mg, 1.48 mmol), 2-hydroxy-1-(piperazin-1-yl)ethanone hydrochloride (7.8 mmol), n-butanol (6 mL) and DIPEA (1 mL) were combined in a sealed tube and heated to 130° C. for 3 days. The reaction mixture was cooled, concentrated onto silica and purified by column chromatography (SiO$_2$, 0-100% EtOAc in isohexane) to give the title compound (43.9 mg, 6%) as a clear gum. $\delta_H$ (CDCl$_3$) 7.97 (1H, s), 7.53 (1H, dd, J 8.90, 6.02 Hz), 7.17 (1H, t, J=8.98 Hz), 5.14 (1H, s), 5.05 (1H, d, J=7.43 Hz), 4.33-4.03 (2H, m), 3.94-3.15 (6H, m), 3.19 (2H, br s), 2.59 (3H, d, J=2.38 Hz), 1.52-1.41 (12H, m), OH exchanging. LCMS (ES+) 447 (M+H)$^+$.

Intermediate 77

(S)-tert-Butyl (S)-1-{2-[(R)-3-(acetamidomethyl)pyrrolidin-1-yl]-8-chloroquinolin-3-yl}ethylcarbamate Intermediate 11 (700 mg, 2.05 mmol), (S)-3-(acetamidomethyl)pyrrolidine hydrochloride (712 mg, 4 mmol), n-butanol (12 mL) and DIPEA (3 mL) were combined in a sealed tube and heated to 130° C. for 3 days. The reaction mixture was cooled, concentrated onto silica and purified by column chromatography (SiO$_2$, 0-100% EtOAc in isohexane) to give the title compound (243 mg, 27%) as a white solid and the regioisomer (189 mg) as a clear glass. $\delta_H$ (DMSO-d$_6$) 8.10 (1H, s), 8.06 (1H, d, J=6.96 Hz), 7.72-7.67 (2H, m), 7.59 (1H, d, J=7.95 Hz), 7.22 (1H, t, J=7.74 Hz), 5.25-5.15 (1H, m), 3.90-3.60 (3H, m), 3.45 (1H, dd, J 10.83, 5.37 Hz), 3.16 (2H, t, J=6.46 Hz), 2.48-2.42 (1H, m), 2.13-2.01 (1H, m), 1.86 (3H, s), 1.80-1.76 (1H, m), 1.46-1.26 (12H, m). LCMS (ES+) 448 (M+H)$^+$.

Intermediate 78

(S)-tert-Butyl 1-[2-(4-carbamoylpiperidin-1-yl)-7-fluoro-8-methylquinolin-3-yl]ethyl-carbamate Intermediate 27 (700 mg, 2.05 mmol), piperidine-4-carboxylic acid amide (500 mg, 3.9 mmol), n-butanol (10 mL) and DIPEA (4 mL) were combined in a sealed tube and heated to 130° C. for 13 days. The reaction mixture was cooled, concentrated onto silica and purified by column chromatography (SiO$_2$, 0-100% EtOAc in isohexane) to give the title compound (823 mg) as a clear gum. LCMS (ES+) 431 (M+H)$^+$.

Intermediate 79

(S)-tert-Butyl 1-{7-fluoro-8-methyl-2-[4-(2,2,2-trifluoroethyl)piperazin-1-yl]quinolin-3yl}ethylcarbamate To a solution of Intermediate 27 (500 mg, 1.48 mmol) in NMP (6 mL) were added 1-(2,2,2-trifluoroethyl)piperazine (500 mg, 3.00 mmol) and DIPEA (1.3 mL) and the resulting solution was heated under microwave irradiation at 130° C. for 1.5 h. The reaction mixture was taken up in EtOAc (150 mL) and washed with water (2×50 mL) and brine (50 mL). The organic phase was separated, dried (phase separation cartridge) and the solvent removed in vacuo. Purification by column chromatography (SiO$_2$, 20% EtOAc in isohexane) gave the title compound (216 mg, 31%) as a beige solid. $\delta_H$ (DMSO-d$_6$) 8.21 (1H, s), 7.74 (1H, t, J=7.54 Hz), 7.59 (1H, t, J=8.65 Hz), 7.32 (1H, t, J=9.12 Hz), 5.06-5.00 (1H, m), 3.56-3.50 (2H, m), 3.15-3.07 (2H, m), 2.96-2.90 (2H, m), 2.89-2.79 (2H, m), 2.60-2.55 (2H, m), 1.41 (9H, s), 1.34 (3H, d, J=7.37 Hz).

Intermediate 80

(S)-1-{7-Fluoro-8-methyl-2-[4-(2,2,2-trifluoroethyl)piperazin-1-yl]quinolin-3-yl}-ethanamine bis hydrochloric acid salt To a solution of Intermediate 79 (216 mg, 0.46 mmol) in DCM (5 mL) was added TFA (5 mL) and the resulting solution stirred at r.t. for 15 minutes. The solvent was removed in vacuo and the residue dissolved in MeOH (6 mL), placed on an SCX cartridge, washed (MeOH) and eluted (3.5M ammonia in MeOH), followed by concentration in vacuo. The residue was dissolved in MeOH and HCl (4M in 1,4-dioxane) and then concentrated in vacuo to afford the title compound (186 mg, 100%) as a white solid. $\delta_H$ (DMSO-d$_6$) 8.54 (1H, s), 8.46 (2H, s), 7.77 (1H, dd, J 8.90, 6.26 Hz), 7.60-7.32 (1H, m), 5.08-4.75 (5H, m), 3.28 (3H, br s), 2.96 (3H, br s), 2.56 (3H, dd, J 7.54, 2.27 Hz), 1.64 (3H, d, J=6.67 Hz).

Intermediate 81 tert-Butyl (S)-1-{2-[(3S,5R)-3,5-dimethylpiperazin-1-yl]-7-fluoro-8-methylquinolin-3-yl}ethylcarbamate To a solution of Intermediate 27 (500 mg, 1.48 mmol) in NMP (6 mL) were added (2S,6R)-2,6-dimethylpiperazine (340 mg, 3.00 mmol) and DIPEA (1.3 mL) and the resulting solution was heated at 140° C. for 16 h. The reaction mixture was taken up in EtOAc (150 mL) and washed with water (2×50 mL) and brine (50 mL). The organic phase was separated, dried (MgSO$_4$), filtered and the solvent removed in vacuo. Purification by column chromatography (SiO$_2$, 0-5% MeOH in EtOAc) gave the title compound (530 mg, 86%) as a beige solid. $\delta_H$ (CDCl$_3$) 7.90 (1H, s), 7.49 (1H, dd, J 8.87, 6.12 Hz), 7.12 (1H, t, J=8.98 Hz), 5.04 (2H, d, J=38.75 Hz), 3.65 (1H, d, J=12.33 Hz), 3.43 (1H, d, J=12.40 Hz), 3.26 (1H, s), 3.14-3.09 (1H, m), 2.79 (1H, t, J=11.35 Hz), 2.60 (3H, d, J=2.40 Hz), 2.43 (1H, t, J=11.28 Hz), 1.48-1.42 (13H, m), 1.15 (6H, dd, J 14.95, 6.35 Hz).

Intermediate 82

(S)-1-{2-[3S,5R)-3,5-Dimethylpiperazin-1-yl]-7-fluoro-8methylquinolin-3-yl}-ethanamine bis hydrochloric acid salt To a solution of Intermediate 81 (530 mg, 1.27 mmol) in DCM (5 mL) was added TFA (5 mL) and the resulting solution stirred at r.t. for 0.25 h. The solvent was removed in vacuo and the residue dissolved in MeOH (6 mL), placed on an SCX cartridge, washed (MeOH) and eluted (3.5M ammonia in MeOH). The eluate was evaporated in vacuo and the residue was dissolved in MeOH and HCl (4M in 1,4-dioxane, 10 mL). The solvent was evaporated in vacuo to afford the title compound (448 mg, 100%) as a white solid. $\delta_H$ (DMSO-d$_6$) 9.76 (1H, d, J=10.25 Hz), 8.99 (1H, d, J=11.52 Hz), 8.61 (1H, s), 8.52 (3H, s), 7.82 (1H, dd, J 8.95, 6.22 Hz), 7.44 (1H, t, J=9.12

Hz), 4.76-4.70 (1H, m), 3.65-3.59 (2H, m), 3.57 (2H, s), 3.13-3.01 (2H, m), 2.57-2.54 (3H, m), 1.64 (3H, t, J=6.49 Hz), 1.33 (6H, 2×d, J=6.26 Hz).

Intermediate 83

(S)-1-[7-Fluoro-2-(4-isopropylpiperazin-1-yl)-8-methylquinolin-3-yl]ethanamine hydrochloric acid salt To a solution of Intermediate 27 (500 mg, 1.48 mmol) in NMP (6 mL) were added 1-isopropylpiperazine (379 mg, 3.00 mmol) and DIPEA (1.3 mL) and the resulting solution was heated in a sealed tube at 140° C. for 64 h. The reaction mixture was taken up in EtOAc (150 mL) and washed with water (2×50 mL) and brine (50 mL). The organic phase was separated, dried (phase separation cartridge) and the solvent removed in vacuo. Purification by column chromatography ($SiO_2$, 0-5% MeOH in EtOAc) gave an off-white solid (450 mg, 71%). To a solution of this material (450 mg, 1.05 mmol) in DCM (5 mL) was added TFA (5 mL) and the resulting solution was stirred at r.t. for 15 minutes. The solvents were removed in vacuo and the residue was dissolved in MeOH (6 mL) and placed on an SCX cartridge, washed (MeOH), eluted (3.5M ammonia in MeOH) and concentrated in vacuo. The residue was redissolved in MeOH and HCl (4M in 1,4-dioxane) and concentrated in vacuo to afford the title compound (380 mg, 100%) as a white solid. $\delta_H$ (DMSO-$d_6$) 10.89 (1H, s), 8.58 (3H, s), 7.82 (1H, dd, J 8.94, 6.24 Hz), 7.44 (1H, t, J 9.12 Hz), 7.23 (1H, t, J=50.95 Hz), 4.89-4.59 (6H, m), 3.69-3.59 (2H, m), 3.50 (4H, t, J=11.46 Hz), 3.40 (1H, t, J=9.64 Hz), 3.29 (1H, s), 2.57 (3H, d, J=2.22 Hz), 1.66 (3H, t, J=6.59 Hz), 1.36 (6H, d, J=6.57 Hz).

Intermediate 84

(S)-1-{4-[3-(1-Aminoethyl)-7-fluoro-8-methylquinolin-2-yl]piperazin-1-yl}-2,2-dimethylpropan-1-one hydrochloric acid salt To a solution of Intermediate 27 (500 mg, 1.48 mmol) in NMP (6 mL) were added 2,2-dimethyl-1-(piperazin-1-yl) propan-1-one (500 mg, 3.00 mmol) and DIPEA (1.3 mL) and the resulting solution was heated at 140° C. for 16 h. The reaction mixture was taken up in EtOAc (150 mL) and washed with water (2×50 mL) and brine (50 mL). The organic phase was separated, dried (phase separation cartridge) and the solvent removed in vacuo. Purification by column chromatography ($SiO_2$, 10-20% EtOAc in isohexane) gave a beige solid (460 mg, 66%). To a solution of this material (460 mg, 0.97 mmol) in DCM (6 mL) was added TFA (3 mL) and the resulting solution was stirred at r.t. for 15 minutes. The solvents were removed in vacuo and the residue was dissolved in MeOH (6 mL) and placed on an SCX cartridge, washed (MeOH), eluted (7M ammonia in MeOH) and concentrated in vacuo. The residue was redissolved in MeOH and HCl (4M in 1,4-dioxane). The solvent was evaporated in vacuo to afford the title compound (397 mg, 100%) as a white solid. $\delta_H$ (CDCl$_3$) 8.11 (1H, s), 7.54 (1H, dd, J 8.86, 6.07 Hz), 7.15 (1H, t, J 9.00 Hz), 4.51 (1H, q, J=6.50 Hz), 3.87 (4H, t, J=5.05 Hz), 3.39-3.26 (4H, m), 2.60 (3H, d, J=2.39 Hz), 1.50 (3H, d, J=6.49 Hz), 1.34 (9H, s), NH$_2$ exchanging.

Intermediate 85

(R,E)-N-[(8-Bromo-2-chloroquinolin-3-yl)methylidene]-2-methylpropane-2-sulfinamide Following the procedure described for Intermediate 1, 8-bromo-2-chloro-quinoline-3-carbaldehyde (280 mg, 1.04 mmol), (R)-(+)-2-methyl-2-propanesulfinamide (125 mg, 1.04 mmol) and titanium isopropoxide (0.61 mL, 2.08 mmol) afforded the title compound (335 mg, 87%) as a yellow solid. $\delta_H$ (CDCl$_3$) 9.12 (1H, s), 8.82 (1H, s), 8.15 (1H, dd, J 7.52, 1.31 Hz), 7.92 (1H, dd, J 8.17, 1.30 Hz), 7.52-7.44 (1H, m), 1.33 (9H, s).

Intermediate 86

(R,E)-N-[(2-Chloro-5-fluoro-8-methylquinolin-3-yl)methylidene]-2-methylpropane-2-sulfinamide Following the procedure described for Intermediate 1,2-chloro-5-fluoro-8, methylquinoline-3-carbaldehyde (800 mg, 3.57 mmol), (R)-(+)-2-methyl-2-propane-sulfinamide (430 mg, 3.57 mmol) and titanium isopropoxide (2.1 mL, 7.14 mmol) afforded the title compound (1.1 g, 94%) as a yellow solid. $\delta_H$ (CDCl$_3$) 9.12 (1H, s), 9.05 (1H, s), 7.62-7.56 (1H, m), 7.18 (1H, dd, J 9.35, 8.00 Hz), 2.73 (3H, s), 1.33 (9H, s).

Intermediate 87

(R)-N-[(S)-1-(8-Bromo-2-chloroquinolin-3-yl) ethyl]-2-methylpropane-2-sulfinamide Following the procedure described for Intermediate 2, Intermediate 85 (305 mg, 0.82 mmol) and methylmagnesium bromide (0.55 mL, 1.64 mmol, 3.0M in Et$_2$O), after purification by column chromatography ($SiO_2$, 80% EtOAc in isohexane), afforded the title compound (120 mg, 38%) as an off-white solid. $\delta_H$ (CDCl$_3$) 8.24 (1H, s), 8.05 (1H, dd, J 7.51, 1.31 Hz), 7.78 (1H, dd, J 8.14, 1.31 Hz), 7.42 (1H, t, J=7.82 Hz), 5.16-5.09 (1H, m), 3.48-3.43 (1H, m), 1.71 (3H, d, J=6.75 Hz), 1.25 (9H, s).

Intermediate 88

(R)-N-[(S)-1-(2-Chloro-5-fluoro-8-methylquinolin-3-yl)ethyl]-2-methylpropane-2-sulfinamide Following the procedure described for Intermediate 2, Intermediate 86 (1.1 g, 3.36 mmol) and methylmagnesium bromide (2.2 mL, 6.72 mmol, 3.0M in Et$_2$O), after purification by column chromatography ($SiO_2$, 40-60% EtOAc in petrol 40-60), afforded the title compound (485 mg, 42%) as a cream solid. $\delta_H$ (CDCl$_3$) 8.46 (1H, s), 7.47 (1H, t, J=6.93 Hz), 7.12 (1H, t, J=8.76 Hz), 5.18-5.10 (1H, m), 3.46 (1H, d, J=4.33 Hz), 2.71 (3H, s), 1.69 (3H, d, J=6.69 Hz), 1.26 (9H, s).

Intermediate 89

(S)-tert-Butyl 1-(8-bromo-2-chloroquinolin-3yl)ethylcarbamate

To a solution of Intermediate 87 (120 mg, 0.31 mmol) in MeOH (3 mL) was added HCl (0.8 mL, 3.08 mmol, 4M in 1,4-dioxane) and the mixture was stirred at r.t. for 30 minutes. The solvent was removed in vacuo to give a viscous colourless oil (110 mg). This oil was dissolved in dry DCM (10 mL) and treated with TEA (0.2 mL, 1.54 mmol) followed by di-tert-butyl dicarbonate (101 mg, 0.46 mmol). The reaction mixture was stirred at r.t. overnight. More di-tert-butyl dicarbonate (20 mg) and TEA (0.1 mL) were added and the mixture stirred at r.t. overnight. Water (20 mL) was added, and the mixture was extracted with DCM (50 mL). The organic layer was separated, dried (MgSO$_4$) and filtered, and the solvent was removed in vacuo. Purification by column chromatography (SiO$_2$, 25% EtOAc in petrol 40-60) afforded the title compound (105 mg, 88%) as a white solid. δ$_H$ (CDCl$_3$) 8.12 (1H, s), 8.02 (1H, dd, J 7.49, 1.31 Hz), 7.77 (1H, dd, J 8.14, 1.31 Hz), 7.40 (1H, t, J=7.81 Hz), 5.25-5.05 (2H, m), 1.41 (12H, br s).

Intermediate 90

(S)-tert-Butyl 1-(2-chloro-5-fluoro-8-methylquinolin-3-yl)ethylcarbamate

Following the procedure described for Intermediate 89, Intermediate 88 (480 mg, 1.40 mmol) and HCl (3.5 mL, 14 mmol, 4M in 1,4-dioxane) in MeOH (3 mL), followed by di-tert-butyl dicarbonate (475 mg, 2.18 mmol) and TEA (1 mL, 7.26 mmol), afforded the title compound (400 mg, 81%) as a white solid. δ$_H$ (CDCl$_3$) 8.34 (1H, s), 7.45 (1H, t, J=6.94 Hz), 7.10 (1H, dd, J 9.63, 7.96 Hz), 5.25-5.15 (1H, m), 5.08 (1H, br s), 2.70 (3H, s), 1.54 (3H, d, J=9.6 Hz), 1.43 (9H, s).

Intermediate 91

(S)-tert-Butyl 1-[8-bromo-2-(3-oxopiperazin-1-yl)quinolin-3-yl]ethylcarbamate

To a solution of Intermediate 89 (100 mg, 0.26 mmol) in NMP (3 mL) were added piperazin-2-one (130 mg, 1.3 mmol) and DIPEA (0.23 mL, 1.3 mmol) and the mixture was heated at 140° C. in a sealed tube overnight. Water (20 mL) was added, then the mixture was extracted with EtOAc (80 mL) and washed with water (4×20 mL). The organic layer was separated, dried (MgSO$_4$), filtered and the solvent removed in vacuo. Purification by column chromatography (SiO$_2$, 80% EtOAc in isohexane) afforded the title compound (75 mg, 64%) as an off-white foamy solid. δ$_H$ (CDCl$_3$) 8.02 (1H, s), 7.93 (1H, dd, J 7.48, 1.31 Hz), 7.68 (1H, dd, J 8.01, 1.30 Hz), 7.29-7.22 (1H, m), 6.38 (1H, s), 5.15-5.05 (2H, m), 4.36 (1H, d, J=17.65 Hz), 4.04 (1H, d, J=17.66 Hz), 3.95-3.88 (1H, m), 3.77-3.70 (1H, m), 3.50-3.35 (2H, m), 1.50-1.35 (12H, m).

Intermediate 92

(S)-tert-Butyl 1-[5-fluoro-8-methyl-2-(3-oxopiperazin-1-yl)quinolin-3-yl]ethylcarbamate Following the procedure described for Intermediate 91, Intermediate 90 (200 mg, 0.59 mmol), piperazin-2-one (295 mg, 2.95 mmol) and DIPEA (0.53 mL, 2.95 mmol) in NMP (3 mL) afforded the title compound (139 mg, 59%) as a lilac solid. δ$_H$ (CDCl$_3$) 8.26 (1H, s), 7.37 (1H, t, J=7.01 Hz), 6.99 (1H, t, J=8.85 Hz), 5.97 (1H, s), 5.18-5.10 (1H, m), 5.05-4.90 (1H, m), 4.30 (1H, d, J=17.6 Hz), 3.95 (1H, d, J=17.2 Hz), 3.95-3.85 (1H, m), 3.88 (1H, s), 3.68-3.60 (1H, m), 3.43-3.35 (2H, m), 2.63 (3H, s), 1.45-1.41 (12H, m).

Intermediate 93

(S)-tert-Butyl 1-[2-(4-acetamidopiperidin-1-yl)-8-chloroquinolin-3-yl]ethylcarbamate Similarly, Intermediate 11 (150 mg, 0.44 mmol), 4-(acetylamino)piperidine (311 mg, 2.19 mmol) and DIPEA (0.39 mL, 2.19 mmol) in NMP (3 mL) afforded the title compound (144 mg, 73%) as an off-white solid. δ$_H$ (CDCl$_3$) 7.95 (1H, s), 7.68 (1H, dd, J 7.6, 1.6 Hz), 7.60 (1H, dd, J 8.0, 1.2 Hz), 7.27 (1H, t, J=7.8 Hz), 5.45-5.40 (1H, m), 5.12-5.03 (1H, m), 4.93-4.86 (1H, m), 4.10-4.00 (1H, m), 3.81-3.76 (1H, m), 3.64-3.57 (1H, m), 3.38-3.30 (1H, m), 3.06-2.97 (1H, m), 2.16-2.04 (2H, m), 2.00 (3H, s), 1.86-1.77 (1H, m), 1.67-1.56 (1H, m), 1.48-1.38 (12H, m).

Intermediate 94 tert-Butyl (S)-1-{2-[(R)-3-acetamidopyrrolidin-1-yl]-7-fluoro-8-methylquinolin-3-yl}ethylcarbamate Similarly, Intermediate 27 (150 mg, 0.44 mmol), 3-(R)-(+)-acetamidopyrrolidine (283 mg, 2.21 mmol) and DIPEA (0.4 mL, 2.21 mmol) in NMP (2 mL) afforded the title compound (173 mg, 91%) as a white solid. δ$_H$ (CDCl$_3$) 7.90 (1H, s), 7.47 (1H, dd, J 8.80, 6.19 Hz), 7.05 (1H, t, J=8.99 Hz), 6.22-6.12 (1H, m), 5.30-5.20 (1H, m), 4.83-4.75 (1H, m), 4.65-4.58 (1H, m), 3.86-3.76 (2H, m), 3.78-3.66 (1H, m), 3.75-3.60 (2H, m), 2.55 (3H, d, J=2.32 Hz), 2.32-2.22 (1H, m), 1.99 (3H, s), 1.50-1.40 (13H, m).

Intermediate 95

(S)-4-[3-(1-Aminoethyl)-8-bromoquinolin-2-yl]piperazin-2-one

To a solution of Intermediate 91 (75 mg, 0.17 mmol) in DCM (3 mL) was added TFA (1 mL) and the reaction was stirred at r.t. for 60 minutes. The mixture was diluted with DCM (20 mL) and ice before being basified with 2M NaOH solution. The aqueous layer was extracted with DCM (2×40 mL), then the organic layers were combined, dried (MgSO$_4$) and filtered. The solvent was removed in vacuo to afford the title compound (35 mg, 60%) as a pale yellow oil. δ$_H$ (CDCl$_3$) 8.23 (1H, s), 7.93 (1H, dd, J 7.6, 1.2 Hz), 7.70 (1H, d, J=8.0 Hz), 7.26 (1H, t, J=7.8 Hz), 6.10-6.05 (1H, m), 4.57-4.52 (1H, m), 4.16 (1H, d, J=17.6 Hz), 4.10 (1H, d, J=17.6 Hz), 3.80-3.55 (4H, m), 1.54 (3H, d, J=6.8 Hz), NH$_2$ exchanging.

Intermediate 96

(S)-4-[3-(1-Aminoethyl)-5-fluoro-8-methylquinolin-2-yl]piperazin-2-one

Following the procedure described for Intermediate 95, Intermediate 92 (130 mg, 0.32 mmol) and TFA (1 mL) in DCM (3 mL) afforded the title compound (76 mg, 78%) as an off-white sticky foam. δ$_H$ (CDCl$_3$) 8.42 (1H, s), 7.36 (1H, t, J=7.01 Hz), 6.98 (1H, dd, J 9.75, 7.92 Hz), 6.02 (1H, s), 4.50 (1H, q, J=6.53 Hz), 4.11 (2H, s), 3.72-3.64 (1H, m), 3.61-3.51 (3H, m), 2.63 (3H, s), 1.52 (3H, d, J=6.4 Hz), NH$_2$ exchanging.

Intermediate 97

N-[(R)-1-{3-[(S)-1-Aminoethyl]-7-fluoro-8-methylquinolin-2-yl}pyrrolidin-3-yl]-acetamide A solution of Intermediate 94 (170 mg, 0.40 mmol) and HCl (1.0 mL, 3.95 mmol, 4M in 1,4-dioxane) in 1,4-dioxane (6 mL) was stirred at r.t. overnight. The solvent was removed in vacuo to afford the title compound (200 mg, quantitative) as a cream solid. δ$_H$ (MeOD-d$_4$) 8.49 (1H, s), 7.76 (1H, dd, J 8.84, 5.65 Hz), 7.26 (1H, t, J 9.08 Hz), 5.00 (1H, q, J=6.73 Hz), 4.51-4.44 (1H, m), 4.15-3.98 (3H, m), 3.85 (1H, dd, J 10.21, 5.59 Hz), 2.49 (3H, d, J=2.08 Hz), 2.38-2.28 (1H, m), 2.16-2.07 (1H, m), 1.91 (3H, s), 1.71 (3H, d, J=6.69 Hz).

Intermediate 98

(S)-1-{8-Chloro-2-[(R)-2-(methoxymethyl)pyrrolidin-1-yl]quinolin-3-yl}ethanamine A solution of Intermediate 11 (150 mg, 0.44 mmol), (R)-2-(methoxymethyl)-pyrrolidine (0.082 mL, 0.66 mmol) and DIPEA (0.39 mL, 2.2 mmol) in NMP (2 mL) was heated at 140° C. for 20 h. After cooling, the mixture was dissolved in a 1:1 mixture of EtOAc and Et$_2$O (200 mL) and washed with saturated brine (3×30 mL). The organic layer was separated, dried (MgSO$_4$), filtered and concentrated in vacuo. Purification by column chromatography (SiO$_2$, 5-10% EtOAc in isohexane) gave an off-white solid (174 mg, 94%). LCMS (ES+) 420, 422 (M+H)$^+$. To the off-white solid (174 mg, 0.415 mmol) dissolved in DCM (5 mL) was added TFA (2 mL). The reaction mixture was stirred at r.t. for 2 h. The solvent was removed in vacuo and the residue azeotroped with toluene. Ion exchange chromatography (SCX cartridge eluting with 0.35M NH$_3$ in MeOH) gave the title compound (95 mg, 72%) as a yellow solid. $\delta_H$ (CDCl$_3$) 7.98 (1H, s), 7.65 (1H, dd, J 7.51, 1.31 Hz), 7.57 (1H, d, J=8.02 Hz), 7.17 (1H, t, J=7.76 Hz), 5.00-4.92 (1H, m), 4.48 (1H, q, J=6.43 Hz), 3.86-3.77 (1H, m), 3.69 (1H, dd, J 9.61, 3.29 Hz), 3.60 (1H, dd, J 9.61, 5.88 Hz), 3.38-3.27 (1H, m), 3.34 (3H, s), 2.25-2.16 (1H, m), 2.08-1.84 (5H, m), 1.60 (3H, d, J=6.40 Hz).

Intermediate 99

(S)-1-{8-Chloro-2-[(S)-2-(methoxymethyl)pyrrolidin-1-yl]quinolin-3-yl}ethanamine A solution of Intermediate 11 (150 mg, 0.44 mmol), (S)-2-(methoxymethyl)-pyrrolidine (0.082 mL, 0.66 mmol) and DIPEA (0.39 mL, 2.2 mmol) in NMP (2 mL) was heated at 140° C. for 20 h. After cooling, the mixture was dissolved in a 1:1 mixture of EtOAc and Et$_2$O (200 mL) and washed with saturated brine (3×30 mL). The organic layer was dried (MgSO$_4$), filtered and concentrated in vacuo. Purification by column chromatography (SiO$_2$, 5-10% EtOAc in isohexane) gave an off-white solid (150 mg, 81%). LCMS (ES+) 420, 422 (M+H)$^+$. To the off-white solid (150 mg, 0.358 mmol) dissolved in DCM (5 mL) was added TFA (2 mL). The reaction mixture was stirred at r.t. for 2 h, concentrated in vacuo and azeotroped with toluene. Ion exchange chromatography (SCX cartridge eluting with 0.35M NH$_3$ in MeOH) gave the title compound (107 mg, 94%) as a yellow solid. $\delta_H$ (CDCl$_3$) 8.18 (1H, s), 7.63 (1H, dd, J 7.60, 1.20 Hz), 7.58 (1H, dd, J 7.60, 1.20 Hz), 7:15 (1H, t, J 7.76 Hz), 4.96-4.88 (1H, m), 4.56 (1H, q, J=6.47 Hz), 3.83-3.72 (2H, m), 3.53-3.41 (2H, m), 3.38 (3H, s), 2.29-2.16 (1H, m), 2.06-1.99 (1H, m), 1.96-1.82 (2H, m), 1.70-1.54 (2H, m), 1.31 (3H, d, J=6.40 Hz).

Intermediate 100

N-[(2,8-Dichloroquinolin-3-yl)methyl]-2-methylpropane-2-sulfinamide

A solution of Intermediate 8 (3.15 g, 9.6 mmol) in dry THF (45 mL) was cooled to 5° C. and treated with sodium borohydride (400 mg, 10.6 mmol) portionwise. The reaction was allowed to attain r.t., stirred for 16 h, cooled to 10° C. and MeOH (10 mL) was added dropwise. The mixture was partitioned between EtOAc (100 mL) and water (30 mL) and the organic layer was washed with water (30 mL) and brine (30 mL), separated and dried (phase separation cartridge). The solvent was removed in vacuo to give the title compound (3.17 g, 100%). $\delta_H$ (CDCl$_3$) 8.25 (1H, s), 7.85-7.74 (2H, m), 7.53-7.46 (1H, m), 4.65-4.52 (2H, m), 3.77 (1H, t, J=6.42 Hz), 1.27-1.18 (9H, m).

Intermediate 101 tert-Butyl (2,8-dichloroquinolin-3-yl)methylcarbamate

Intermediate 100 (3.17 g, 9.6 mmol) was dissolved in MeOH (20 mL) and 4M HCl in 1,4-dioxane (30 mL) was added. The mixture was stirred for 2 h and the solvent removed in vacuo. The residue was taken up in MeOH and placed on an SCX cartridge, washed (MeOH) and eluted with 3.5M NH$_3$ in MeOH. The solvent was removed in vacuo and the residue was dissolved in DCM (20 ml) and treated with di-tert-butyl dicarbonate (850 mg, 3.9 mmol). The mixture was stirred for 5 minutes before the dropwise addition of DIPEA (460 mg, 3.5 mmol). The reaction mixture was stirred for 16 h. The solvent was removed in vacuo and the residue was triturated with Et$_2$O to give the title compound (785 mg, 27%) as a yellow solid. $\delta_H$ (CDCl$_3$) 8.18 (1H, s), 7.82 (1H, d, J 7.55 Hz), 7.75 (1H, d, J=8.17 Hz), 7.48 (1H, t, J=7.85 Hz), 5.21 (1H, s), 4.54 (2H, d, J=6.41 Hz), 1.45 (9H, s).

Intermediate 102 tert-Butyl[8-chloro-2-(3-oxopiperazin-1-yl)quinolin-3-yl]methylcarbamate

Intermediate 101 (785 mg, 2.4 mmol), piperazin-2-one (963 mg, 9.6 mmol), NMP (10 mL) and DIPEA (2.15 mL, 12.0 mmol) were combined in a sealed tube and heated to 130° C. for 16 h. The reaction mixture was then cooled and partitioned between EtOAc (100 mL) and water (20 mL). The organic layer was washed with water (2×30 mL) and brine (30 mL), separated, dried (MgSO$_4$) and concentrated in vacuo. Purification by column chromatography (SiO$_2$ 5% MeOH in DCM) gave the title compound (550 mg, 59%) as an off-white solid. $\delta_H$ (DMSO-d$_6$) 8.13 (1H, s), 8.01 (1H, s), 7.89-7.81 (2H, m), 7.59 (1H, s), 7.42 (1H, t, J 7.80 Hz), 4.33 (2H, d, J=5.83 Hz), 3.97 (2H, s), 3.51 (2H, d, J=5.37 Hz), 3.42-3.40 (2H, m), 1.45 (9H, s).

Intermediate 103

4-[3-(Aminomethyl)-8-chloroquinolin-2-yl]piperazin-2-one

Intermediate 102 (520 mg, 1.3 mmol) in DCM (16 mL) was treated with TFA (4 mL) and stirred for 30 minutes. The solvents were removed in vacuo and the residue was redissolved in MeOH and passed through a SCX cartridge eluting with 7M NH$_3$/MeOH. The solvent was removed in vacuo to give the title compound (200 mg, 53%). $\delta_H$ (CDCl$_3$) 8.16 (1H, s), 7.71 (1H, dd, J 7.53, 1.33 Hz), 7.64 (1H, dd, J 8.09, 1.35 Hz), 7.30 (1H, t, J 7.80 Hz), 5.92 (1H, s), 4.19 (2H, s), 4.05 (2H, s), 3.74 (2H, t, J 5.33 Hz), 3.67 (2H, d, J=5.57 Hz), NH$_2$ exchanging.

Example 1

6-Methyl-N-{(S)-1-[8-methyl-2-(morpholin-4-yl)quinolin-3-yl]ethyl}-[1,3,5]triazine-2,4-diamine To a solution of Intermediate 5 (97 mg, 0.26 mmol) in DCM (2 mL) was added TFA (2 mL) and the resulting solution was stirred at r.t. for 2 h. The solvents were removed in vacuo and the residue was redissolved in n-butanol (3 mL). DIPEA (0.42 mL, 2.33 mmol) and 2-amino-4-chloro-6-methyl-[1,3,5]triazine (102 mg, 0.71 mmol) were added and the resulting solution was heated in a microwave at 150° C. for 1 h. The solvent was removed in vacuo and the residue redissolved in DCM (20 mL) and the mixture washed with water (2×5 mL). The organic layer was separated, dried (MgSO$_4$), filtered and the solvent removed in vacuo. Purification by preparative HPLC afforded the title compound (74 mg, 75%) as a white solid. $\delta_H$ (CDCl$_3$) 7.96 (s, 1H), 7.52 (d, J=8.0 Hz, 1H), 7.45 (d, J=7.0 Hz, 1H), 7.28 (t, J=7.0 Hz, 1H), 5.38-5.68 (m, 2H), 4.90-5.10 (m, 2H), 3.95-4.03 (m, 2H), 3.84-3.91 (m, 2H), 3.54-3.86 (m, 2H), 3.11-3.18 (m, 2H), 2.72 (s, 3H), 2.11-2.34 (m, 3H), 1.51 (s, 3H). LCMS (ES+) 380 (M+H)$^+$, RT 4.24 minutes (Method 11); RT 23.3 minutes (Method 7).

Example 2

6-Methyl-N-{(S)-1-[8-methyl-2-(pyrrolidin-1-yl) quinolin-3-yl]ethyl}-[1,3,5]triazine-2,4-diamine The title compound was prepared in a similar manner to Example 1, using Intermediate 6, and was obtained as a white solid (51 mg, 60%) after purification by preparative HPLC. $\delta_H$ (CDCl$_3$) 7.88 (s, 1H), 7.45 (d, J=8.0 Hz, 1H), 7.38 (d, J 7.0 Hz, 1H), 7.12 (dd, J 8.0, 7.0 Hz, 1H), 5.60 (q, J 6.3 Hz, 1H), 5.04 (s, 2H), 3.77-3.83 (m, 2H), 3.60-3.70 (m, 2H), 2.65 (s, 3H), 1.91-2.08 (m, 4H), 1.48 (d, J=6.3 Hz, 3H). LCMS (ES+) 364 (M+H)$^+$, RT 2.22 minutes (Method 12).

Example 3

4-{3-[(S)-1-(4-Amino-6-methyl-[1,3,5]triazin-2-ylamino)ethyl]-8-methylquinolin-2-yl}-piperazin-2-one To a solution of Intermediate 7 (75 mg, 0.26 mmol) in n-butanol (2.0 mL) were added 2-amino-4-chloro-6-methyl-[1,3,5]triazine (76 mg, 0.52 mmol) and DIPEA (0.08 mL, 0.6 mmol). The reaction mixture was heated at 160° C. in a microwave for 1 h. The solvent was removed in vacuo and the residue purified by column chromatography (SiO$_2$, 4% MeOH in DCM) to give the title compound (28 mg, 24%) as a light brown solid. $\delta_H$ (CDCl$_3$) 8.02 (s, 1H), 7.47 (d, J=6.8 Hz, 1H), 7.41 (d, J=6.8 Hz, 1H), 7.25 (t, J=6.8 Hz, 1H), 6.38 (d, J=6.8 Hz, 1H), 5.35-5.60 (m, 2H), 5.05 (d, J=17.2 Hz, 1H), 4.73 (d, J=17.2 Hz, 1H), 4.17-4.28 (m, 1H), 3.95-4.09 (br m, 1H), 3.45-3.58 (br m, 2H), 2.67 (s, 3H), 2.22 (s, 3H), 2.20 (br s, 2H), 1.37 (d, J=6.8 Hz, 3H). LCMS (ES+) 393 (M+H)$^+$, RT 3.32 minutes (Method 12).

Example 4

N$^2$-[(S)-1-{8-Chloro-2-[(S)-3-methylmorpholin-4-yl]quinolin-3-yl}ethyl]-[1,3,5]triazine-2,4-diamine A solution/suspension of Intermediate 13 (35 mg, 0.09 mmol), 2-amino-4-chloro-[1,3,5]triazine (18 mg, 0.14 mmol) and DIPEA (0.10 mL, 0.46 mmol) in n-butanol (1.5 mL) was heated at 120° C. under microwave irradiation for 1 h. The solvent was removed in vacuo and the residue purified by preparative HPLC to afford the title compound (14 mg, 38%) as an off-white solid. $\delta_H$ (MeOD-d$_4$) 8.27 (1H, s), 8.00 (1H, s), 7.76 (2H, t), 7.38 (1H, t), 5.66 (1H, m), 4.05-3.98 (1H, m), 3.94-3.81 (3H, m), 3.46 (1H, m), 3.35 (2H, under MeOD), 1.60 (3H, d), 1.15 (3H, d) (3 NH missing, 2H morph under MeOH). LCMS (ES+) 400 (M+H)$^+$, RT 2.63 minutes (Method 2).

Example 5

N$^2$-[(S)-1-{8-Chloro-2-[(S)-3-methylmorpholin-4-yl]quinolin-3-yl}ethyl]-6-methyl-[1,3,5]triazine-2,4-diamine Following the procedure described for Example 4, Intermediate 13 (35 mg, 0.09 mmol), 2-amino-4-chloro-6-methyl-[1,3,5]triazine (20 mg, 0.14 mmol) and DIPEA (0.10 mL, 0.46 mmol) in n-butanol (1.5 mL) gave the title compound (26 mg, 68%) as an off-white solid. $\delta_H$ (MeOD-d$_4$) 8.29 (1H, m), 7.75 (2H, d, J=8.5 Hz), 7.37 (1H, m), 5.67 (1H, q, J=6.8 Hz), 4.02 (1H, s), 3.94-3.81 (3H, m), 3.50 (1H, s), 3.35 (2H, under MeOH), 2.21 (3H, s), 1.59 (3H, s), 1.20 (3H, m). LCMS (ES+) 412 (M+H)$^+$, RT 3.22 minutes (Method 1).

Example 6

N-[(S)-1-{3-[(S)-1-(4-Amino-6-methyl-[1,3,5]triazin-2-ylamino)ethyl]-8-methylquinolin-2-yl}pyrrolidin-3-yl]acetamide Following the procedure described for Example 1, Intermediate 16 (80 mg, 0.19 mmol), DCM (2 mL) and TFA (2 mL) gave the intermediate amine. This was dissolved in n-butanol (2 mL). DIPEA (0.65 mL, 3.75 mmol) and 2-amino-4-chloro-6-methyl-[1,3,5]triazine (163 mg, 1.13 mmol) were added, to give the title compound (16 mg, 20%) as a solid. $\delta_H$ (MeOD-d$_4$) 8.03 (1H, s), 7.50 (1H, d, J=8.0 Hz), 7.39 (1H, d, J=7.0 Hz), 7.15 (1H, t, J=7.5 Hz), 5.68 (1H, m), 4.45-4.36 (1H, m), 4.12-3.93 (2H, m), 3.75-3.64 (2H, m), 2.72-2.58 (3H, m), 2.38-2.30 (1H, m), 2.36-2.05 (3H, m), 1.99 (4H, m), 1.47 (3H, d, J=6.8 Hz). LCMS (ES+) 421 (M+H)$^+$, RT 2.75 minutes (Method 1).

Example 7

(S)-6-Methyl-N$^2$-{1-[8-methyl-2-thiomorpholin-4-yl]quinolin-3-yl]ethyl}-[1,3,5]triazine-2,4-diamine Following the procedure described for Example 1, Intermediate 17 (80 mg, 0.21 mmol), DCM (2 mL) and TFA (2 mL) gave the intermediate amine. This was dissolved in NMP (2 mL). DIPEA (0.18 mL, 1.0 mmol) and 2-amino-4-chloro-6-methyl-[1,3,5]triazine (45 mg, 0.31 mmol) were added, to give the title compound (16 mg, 20%) as a solid. $\delta_H$ (DMSO-d$_6$) (at 125° C.) 8.24 (1H, s), 7.62 (1H, d, J=8.0 Hz), 7.49 (1H, d, J=7.0 Hz), 7.34-7.29 (1H, m), 7.11 (1H, d), 6.02 (2H, s), 5.57-5.50 (1H, m), 3.86 (2H, m), 3.51 (2H, m), 3.00-2.93 (2H, m), 2.91-2.80 (2H, m), 2.71 (3H, s), 2.14 (3H, s), 1.48 (3H, d, J=6.8 Hz). LCMS (ES+) 396 (M+H)$^+$, RT 21.23 minutes (Method 6).

Example 8

(S)-6-Methyl-N$^2$-{1-[8-chloro-2-(1,1-dioxothiomorpholin-4-yl)quinolin-3-yl]ethyl}-[1,3,5]triazine-2,4-diamine Intermediate 18 (55 mg, 0.12 mmol) was dissolved in 1,4-dioxane (1 mL). HCl (4M in 1,4-dioxane; 0.62 mL) was added and the resulting solution was stirred overnight. The solvent was removed in vacuo. The resulting crude amine was dissolved in NMP (1 mL). DIPEA (0.22 mL, 1.25 mmol) and 2-amino-4-chloro-6-methyl-[1,3,5]triazine (91 mg, 0.63 mmol) were added and the mixture was heated under microwave irradiation to 150° C. for 1 h. After cooling, the solvents were removed in vacuo. The crude material was dissolved in DCM and the organic layer was washed with water and brine. The organic layer was dried (MgSO$_4$), filtered and the solvent removed in vacuo. Purification by preparative HPLC gave the title compound (4.6 mg, 8%) as a solid. $\delta_H$ (DMSO-d$_6$) 8.39 (1H, s), 7.81 (2H, d, J=7.8 Hz), 7.46-7.41 (1H, m), 6.12 (2H, s), 5.50 (1H, d, J=7.2 Hz), 4.10-4.05 (2H, m), 3.96-3.90 (2H, m), 3.53-3.48 (2H, m), 3.35-3.31 (1H, m), 2.52 (2H, under DMSO), 2.13 (3H, s), 1.50 (3H, d, J=6.8 Hz). LCMS (ES+) 448 (M+H)$^+$, RT 2.29 minutes (Method 2).

Example 9

(S)-N-(1-{3-[1-(4-Amino-6-methyl-[1,3,5]triazin-2-ylamino)ethyl]-8-chloroquinolin-2-yl}piperidin-4-yl)methanesulfonamide Following the procedure described for Example 8, Intermediate 19 (266 mg, 0.55 mmol), 1,4-dioxane (1 mL) and HCl (4M in 1,4-dioxane; 2.75 mL) gave the intermediate amine. This was dissolved in NMP (3 mL), and DIPEA (0.96 mL, 5.5 mmol) and 2-amino-4-chloro-6-methyl-[1,3,5]triazine (399 mg, 2.75 mmol) were added, to give the title compound (37 mg, 13%) as a solid. $\delta_H$ (DMSO-d$_6$) 8.26 (1H, s), 7.88 (1H, d, J=8.0 Hz), 7.82-7.74 (2H, m), 7.36-7.42 (2H, m), 7.20 (1H, dd, J 15.5, 7.2 Hz), 6.65 (1H, s), 6.33 (1H, s), 5.47-5.35 (1H, m), 4.30 (1H, d, J=12.6 Hz), 4.08 (1H, d, J=12.9 Hz), 3.63 (2H, d), 3.00 (3H, s), 2.79 (2H, m), 2.18-2.08 (2H, m), 2.06 (2H, m), 1.88 (1H, d), 1.66 (1H, d, J=12.6 Hz), 1.42-1.35 (3H, m). LCMS (ES+) 491 (M+H)$^+$, RT 2.93 minutes (Method 1).

Example 10

(S)-N-(1-{3-[1-(4-Amino-[1,3,5]triazin-2-ylamino)ethyl]-8-chloroquinolin-2-yl}-piperidin-4-yl)methanesulfonamide Following the procedure described for Example 8, Intermediate 19 (266 mg, 0.55 mmol), 1,4-dioxane (1 mL) and HCl (4M in 1,4-dioxane; 2.75 mL) gave the intermediate amine. This was dissolved in NMP (3 mL), and DIPEA (0.96 mL, 5.5 mmol) and 2-amino-4-chloro-[1,3,5]triazine (358 mg, 2.75 mmol) were added, to give the title compound (22 mg, 13%) as a solid. $\delta_H$ (DMSO-d$_6$) 8.26 (1H, s), 8.02 (1H, s), 7.96 (1H, d, J=7.9 Hz), 7.79 (2H, d, J=7.7 Hz), 7.42-7.35 (1H, m), 7.18 (1H, m), 5.45-5.32 (1H, m), 4.15-3.96 (1H, m), 3.62 (1H, m), 3.42 (1H, m), 3.26 (2H, m), 3.00 (3H, s), 2.86-2.74 (1H, m), 2.11 (2H, m), 1.98 (1H, s), 1.85 (1H, m), 1.66 (1H, m), 1.42 (3H, d, J=6.6 Hz). LCMS (ES+) 477 (M+H)$^+$, RT 2.52 minutes (Method 2).

Example 11

(S)-1-(4-{3-[1-(4-Amino-[1,3,5]triazin-2-ylamino)ethyl]-8-chloroquinolin-2-yl}piperazin-1-yl)ethanone Following the procedure described for Example 8, Intermediate 20 (193 mg, 0.45 mmol), 1,4-dioxane (1 mL) and HCl (4M in 1,4-dioxane; 2.25 mL) gave the intermediate amine. This was dissolved in NMP (2.5 mL), and DIPEA (0.78 mL, 4.5 mmol) and 2-amino-4-chloro-[1,3,5]triazine (293 mg, 2.25 mmol) were added. Purification by preparative HPLC followed by column chromatography on silica, eluting with 0-5% MeOH in DCM, gave the title compound (15 mg, 19%). $\delta_H$ (DMSO-d$_6$) 8.34-8.27 (1H, m), 8.06-7.95 (2H, m), 7.85-7.81 (3H, m), 7.47-7.39 (1H, m), 5.50-5.39 (1H, m), 3.82-3.64 (7H, m), 3.24-3.02 (2H, m), 2.11 (3H, s), 1.43 (3H, d, J=6.6 Hz). LCMS (ES+) 427 (M+H)$^+$, RT 15.55 minutes (Method 6).

Example 12

(S)-1-(4-{3-[1-(4-Amino-6-methyl-[1,3,5-]triazin-2-ylamino)ethyl]-8-chloroquinolin-2-yl}piperazin-1-yl)ethanone Following the procedure described for Example 6, Intermediate 20 (193 mg, 0.45 mmol), 1,4-dioxane (1 mL) and HCl (4M in 1,4-dioxane; 2.25 mL) gave the intermediate amine. This was redissolved in NMP (2.5 mL), and DIPEA (0.78 mL, 4.5 mmol) and 2-amino-4-chloro-6-methyl-[1,3,5]triazine (293 mg, 2.25 mmol) were added, to give the title compound (33 mg, 17%). $\delta_H$ (DMSO-d$_6$) 8.35 (1H, s), 7.79-7.75 (2H, m), 7.41-7.36 (1H, m), 7.22 (1H, d, J=8.2 Hz), 6.11 (2H, s), 5.61-5.54 (1H, m), 3.86-3.78 (2H, m), 3.75-3.64 (5H, m), 3.34-3.26 (2H, m) 2.51 (2H, m), 2.16-2.05 (3H, m), 1.52-1.46 (3H, m). LCMS (ES+) 441 (M+H)$^+$, RT 2.78 minutes (Method 1).

Example 13

(S)-4-{3-[1-(4-Amino-[1,3,5]triazin-2-ylamino)ethyl]-8-methylquinolin-2-yl}piperazin-2-one To a solution of Intermediate 7 (100 mg, 0.35 mmol) in n-butanol (2.0 mL) was added 2-amino-4-chloro-[1,3,5]triazine (50 mg, 0.37 mmol) and DIPEA (0.1 mL, 0.7 mmol). The reaction mixture was heated at 100° C. overnight. The solvent was removed in vacuo and the residue purified by preparative HPLC to give the title compound (6 mg, 5%) as an off-white solid. $\delta_H$ (CDCl$_3$) 8.11 (1H, s), 8.02 (1H, s), 7.51 (1H, d, J=8.0 Hz), 7.44 (1H, d, J=7.0 Hz), 7.31-7.21 (1H, m), 6.23-6.05 (2H, m), 5.41 (1H, m), 5.12 (1H, d, J=17.5 Hz), 4.67 (1H, d, J=17.4 Hz), 4.32-4.22 (1H, m), 4.11-4.02 (1H, m), 3.60-3.45 (2H, m), 2.68 (3H, s), 1.79 (2H, s), 1.40 (3H, d, J=6.6 Hz). LCMS (ES+) 379 (M+H)$^+$, RT 14.58 minutes (Method 6).

Example 14

(S)-4-{3-[1-(4-Amino-[1,3,5]triazin-2-ylamino)ethyl]-8-chloroquinolin-2-yl}piperazin-2-one To a solution of Intermediate 30 (120 mg, 0.39 mmol) in n-butanol (2.5 mL) was added 2-amino-4-chloro-[1,3,5]triazine (95 mg, 0.79 mmol) and DIPEA (0.14 mL, 0.79 mmol). The reaction mixture was heated at 120° C. under microwave irradiation for 1 h. The solvent was removed in vacuo and the residue purified by preparative HPLC followed by chromatography on an SCX column, eluting with 1M NH$_3$ in MeOH, to give the title compound (20 mg, 13%) as an off-white solid. $\delta_H$ (DMSO-d$_6$) 8.37-8.28 (1H, m), 8.20 (1H, d, J=7.3 Hz), 8.13 (1H, s), 8.06-7.97 (1H, m), 7.90-7.77 (2H, m), 7.44-7.36 (1H, m), 7.05-6.80 (2H, m), 5.48-5.37 and 5.31-5.23 (1H, m), 4.82 (1H, d, J=17.3 Hz), 4.37 (1H, d, J=17.2 Hz), 4.23-3.82 (2H, m), 3.45-3.20 (2H, under H₂O), 1.45-1.30 (3H, m). LCMS (ES+) 399 (M+H)⁺, RT 16.73 minutes (Method 6).

Example 15

(S)-4-{3-[1-(4-Amino-6-methyl-[1,3,5]triazin-2-ylamino)ethyl]-8-chloroquinolin-2-yl}piperazin-2-one To a solution of Intermediate 30 (120 mg, 0.39 mmol) in n-butanol (2.5 mL) was added 2-amino-4-chloro-6-methyl-[1,3,5]triazine (114 mg, 0.79 mmol) and DIPEA (0.14 mL, 0.79 mmol). The reaction mixture was heated at 120° C. under microwave irradiation for 1 h. The solvent was removed in vacuo and the residue purified by preparative HPLC to give the title compound (39 mg, 24%) as an off-white solid. $\delta_H$ (DMSO-d₆) 8.34-8.28 (1H, m), 8.15-8.06 (2H, m), 7.84-7.78 (2H, m), 7.46-7.36 (1H, m), 6.96-6.69 (2H, m), 5.44-5.39 and 5.31-5.23 (1H, m), 4.86 (1H, d, J 17.3 Hz), 4.37 (1H, d, J 17.2 Hz), 4.31-3.84 (2H, m), 3.45-3.20 (2H, under H₂O), 2.14 and 2.06 (3H, 2 s), 1.40-1.29 (3H, m). LCMS (ES+) 413 (M+H)⁺, RT 15.52 minutes (Method 6).

Example 16

(S)-4-{3-[1-(4-(4-Amino-[1,3,5]triazin-2-ylamino)ethyl]-7-fluoro-8-methylquinolin-2-yl}piperazin-2-one To a solution of Intermediate 29 (270 mg, 0.67 mmol) in MeOH (2 mL) was added hydrogen chloride (1 mL; 4N solution in 1,4-dioxane) and the mixture was stirred at r.t. overnight. The solvents were removed in vacuo to give 200 mg of a mauve solid. Half of this solid was dissolved in n-butanol (2 mL). DIPEA (0.1 mL, 0.78 mmol) and 2-amino-4-chloro-[1,3,5]triazine (52 mg, 0.4 mmol) were added and the resulting solution was heated at 110° C. overnight. The solvent was removed in vacuo and the residue was purified by preparative HPLC to give the title compound (20 mg, 16%) as an off-white solid. $\delta_H$ (CDCl₃) 8.09 (1H, s), 7.99 (1H, s), 7.45 (1H, dd, J 8.9, 6.1 Hz), 7.10 (1H, t, J=9.0 Hz), 6.70 (1H, d, J=7.0 Hz), 6.40 (1H, br s), 5.44-5.35 (2H, m), 5.19 (1H, d, J 17.5 Hz), 4.68 (1H, d, J 17.5 Hz), 4.28-4.17 (1H, m), 4.14-4.06 (1H, m), 3.60-3.51 (2H, m), 2.57 (3H, s), 1.39 (3H, d, J=6.6 Hz). LCMS (ES+) 397 (M+H)⁺, RT 2.28 minutes (Method 2).

Example 17

(S)-4-{3-[1-(4-Amino-6-methyl-[1,3,5]triazin-2-ylamino)ethyl]-7-fluoro-8-methyl-quinolin-2-yl}piperazin-2-one To a solution of Intermediate 29 (270 mg, 0.67 mmol) in MeOH (2 mL) was added hydrogen chloride (1 mL; 4N solution in 1,4-dioxane) and the mixture was stirred at r.t. overnight. The solvents were removed in vacuo to give 200 mg of a mauve solid. Half of this solid was dissolved in n-butanol (2 mL). DIPEA (0.1 mL, 0.78 mmol) and 2-amino-4-chloro-6-methyl-[1,3,5]triazine (60 mg, 0.4 mmol) were added and the resulting solution was heated at 110° C. overnight. The solvent was removed in vacuo and the residue was purified by preparative HPLC to give the title compound (45 mg, 33%) as a cream solid. $\delta_H$ (CDCl₃) 8.01 (1H, s), 7.46 (1H, dd, J 8.9, 6.0 Hz), 7.11 (1H, t, J=7.1 Hz), 6.87 (1H, d, J=7.1 Hz), 6.74 (1H, br s), 5.45-5.37 (1H, m), 5.14 (1H, d J 17.5 Hz), 4.71 (1H, d, J 17.5 Hz), 4.26-4.16 (1H, m), 4.12-4.03 (1H, m), 3.64-3.46 (2H, m), 2.69-2.51 (5H, m), 2.27 (3H, s), 1.38 (3H, d, J=6.6 Hz). LCMS (ES+) 441 (M+H)⁺, RT 2.04 minutes (Method 1).

Example 18

N-{(1S)-1-[8-Chloro-2-(pyrrolidin-1-yl)quinolin-3-yl]ethyl}-[1,3,5]triazine-2,4-diamine To a solution of Intermediate 38 (44 mg, 0.16 mmol) in 1,4-dioxane (2 mL) were added 2-amino-4-chloro-[1,3,5]triazine (42 mg, 0.32 mmol) and DIPEA (0.06 mL, 0.35 mmol) and the mixture was heated at 120° C. under microwave irradiation for 1 h. The solvent was removed in vacuo and the residue purified by preparative HPLC to afford the title compound (5.4 mg, 9%) as an off-white solid. $\delta_H$ (DMSO-d₆) 8.14-8.00 (1H, m), 7.74-7.62 (2H, m), 7.24-7.14 (1H, m), 6.83-6.73 (2H, m), 5.71-5.61 (1H, m), 3.78 (4H, d, J 17.65 Hz), 2.52 (2H, under DMSO), 2.06-1.94 (4H, s), 1.40-1.33 (3H, m). LCMS (ES+) 370 (M+H)⁺, RT 3.42 minutes (Method 1).

Example 19

N-{(1S)-1-[8-Chloro-2-(morpholin-4-yl)quinolin-3-yl]ethyl}-6-methyl-[1,3,5]triazine-2,4-diamine Following the procedure described for Example 18, Intermediate 39 (75 mg, 0.26 mmol), 2-amino-4-chloro-6-methyl-[1,3,5]triazine (74 mg, 0.57 mmol) and DIPEA (0.088 mL, 0.57 mmol) in 1,4-dioxane (2 mL) afforded the title compound (70 mg, 68%) as an off-white solid. $\delta_H$ (DMSO-d₆) 8.31 (1H, d, J=6.3 Hz), 7.89 (1H, d, J=8.1 Hz), 7.79 (2H, dd, J 19.1, 7.7 Hz), 7.41 (1H, t, J=7.8 Hz), 6.59 (2H, d, J=8.3 Hz), 5.47 (1H, m), 3.97-3.89 (2H, m), 3.81 (3H, t, J=8.3 Hz), 3.68 (1H, d, J=12.8 Hz), 3.13 (2H, m), 2.13 (2H, s), 2.05 (1H, s), 1.41 (3H, d, J=6.5 Hz). LCMS (ES+) 400 (M+H)⁺, RT 3.10 minutes (Method 1).

Example 20

(3R)-1-(3-{(1S)-1-[(4-Amino-[1,3,5]triazin-2-yl)amino]ethyl}-8-chloroquinolin-2-yl)pyrrolidin-3-ol Following the procedure described for Example 18, Intermediate 40 (55 mg, 0.19 mmol), 2-amino-4-chloro-[1,3,5]triazine (50 mg, 0.38 mmol) and DIPEA (0.065 mL, 0.38 mmol) in 1,4-dioxane (2 mL) afforded the title compound (14 mg, 19%) as an off-white solid. $\delta_H$ (DMSO-d₆) 8.14-7.89 (2H, m), 7.73-7.62 (2H, m), 7.27-7.15 (1H, m), 6.85 (1H, s), 6.60 (1H, s), 5.70-5.56 (1H, m), 4.48 (1H, s), 4.11-4.00 (1H, m), 3.96 (1H, d, J=11.2 Hz), 3.77-3.67 (3H, m), 3.58 (1H, d, J=11.6 Hz), 2.00 (2H, s), 1.34 (3H, d, J=6.8 Hz). LCMS (ES+) 386 (M+H)⁺, RT 10.79 minutes (Method 5).

Example 21

(3R)-1-(3-{(1S)-1-[(4-Amino-6-methyl-[1,3,5]triazin-2-yl)amino]ethyl}-8-chloro-quinolin-2-yl)pyrrolidin-3-ol Following the procedure described for Example 18, Intermediate 40 (55 mg, 0.19 mmol), 2-amino-4-chloro-6-methyl-[1,3,5]triazine (55 mg, 0.38 mmol) and DIPEA (0.065 mL, 0.38 mmol) in 1,4-dioxane (2 mL) afforded the title compound (31 mg, 40%) as an off-white solid. $\delta_H$ (DMSO-d₆)

8.06 (1H, d, J=10.42 Hz), 7.93 (1H, d), 7.77-7.62 (2H, m), 7.18 (1H, t, J=7.73 Hz), 6.64 (2H, m), 5.61 (1H, m), 4.94 (1H, m), 4.48 (1H, s), 4.11-3.92 (2H, m), 3.83-3.63 (2H, m), 2.16 (2H, s), 2.09 (1H, s), 2.04-1.97 (2H, m), 1.32 (3H, d, J=6.5 Hz). LCMS (ES+) 400 (M+H)$^+$, RT 15.76 minutes (Method 6).

Example 22

(3S)-1-(3-{(1S)-1-[(4-Amino-[1,3,5]-triazin-2-yl) amino]ethyl}-8-chloroquinolin-2-yl)pyrrolidin-3-ol Following the procedure described for Example 18, Intermediate 41 (55 mg, 0.19 mmol), 2-amino-4-chloro-[1,3,5] triazine (50 mg, 0.38 mmol) and DIPEA (0.065 mL, 0.38 mmol) in 1,4-dioxane (2 mL) afforded the title compound (12 mg, 16%) as an off-white solid. $\delta_H$ (DMSO-d$_6$) 8.12 (1H, s), 8.05-7.88 (2H, m), 7.67 (2H, t, J=9.02 Hz), 7.18 (1H, t, J=7.72 Hz), 6.87 (1H, s), 6.62 (1H, s), 5.67 (1H, m), 5.16 (1H, br s), 4.44 (1H, d, J=7.47 Hz), 4.00-3.81 (3H, m), 3.66-3.59 (1H, m), 2.13 (1H, s), 1.92 (1H, t, J=8.69 Hz), 1.46 (3H, d, J=6.73 Hz). LCMS (ES+) 386 (M+H)$^+$, RT 15.93 minutes (Method 6).

Example 23

(3S)-1-(3-{(1S)-1-[(4-Amino-6-methyl-[1,3,5]triazin-2-yl)amino]ethyl}-8-chloroquinolin-2-yl)pyrrolidin-3-ol Following the procedure described for Example 18, Intermediate 41 (55 mg, 0.19 mmol), 2-amino-4-chloro-6-methyl-[1,3,5]triazine (55 mg, 0.38 mmol) and DIPEA (0.065 mL, 0.38 mmol) in 1,4-dioxane (2 mL) afforded the title compound (30 mg, 39%) as an off-white solid. $\delta_H$ (DMSO-d$_6$) 8.13 (1H, d, J=11.9 Hz), 7.86 (1H, d, J=7.6 Hz), 7.73-7.62 (2H, m), 7.24-7.14 (1H, m), 6.77 (1H, s), 6.62 (1H, br s), 6.50 (1H, br s), 5.80-5.62 (1H, m), 4.44 (1H, s), 4.00-3.94 (2H, m), 3.90-3.80 (1H, m), 3.63 (1H, m), 2.10 (4H, m), 1.97-1.89 (1H, m), 1.44 (3H, d, J=6.7 Hz). LCMS (ES+) 400 (M+H)$^+$, RT 15.62 minutes (Method 6).

Example 24

1-(3-{(1S)-1-[(4-Amino-[1,3,5]triazin-2-yl)amino] ethyl}-8-chloroquinolin-2-yl)-[1,4]-diazepan-5-one Following the procedure described for Example 18, Intermediate 42 (55 mg, 0.17 mmol), 2-amino-4-chloro-[1,3,5] triazine (45 mg, 0.35 mmol) and DIPEA (0.2 mL) in 1,4-dioxane (3 mL) afforded the title compound (8 mg, 11%) as an off-white solid. $\delta_H$ (DMSO-d$_6$) 8.32-8.24 (1H, m), 8.08-8.00 (1H, m), 7.96 (1H, d, J=7.88 Hz), 7.81 (2H, d, J=7.84 Hz), 7.72 (1H, s), 7.41 (1H, t, J=7.78 Hz), 6.77 (2H, m), 5.36 (1H, d, J=11.4 Hz), 3.75-3.61 (3H, m), 3.51-3.43 (3H, m), 2.85 (1H, m), 2.70 (1H, m), 1.43 (3H, d, J=6.5 Hz). LCMS (ES+) 413 (M+H)$^+$, RT 2.20 minutes (Method 2).

Example 25

1-(3-{(1S)-1-[(4-Amino-6-methyl-[1,3,5]triazin-2-yl)amino]ethyl}-8-chloroquinolin-2-yl)-[1,4]diaz-epan-5-one Following the procedure described for Example 18, Intermediate 42 (55 mg, 0.17 mmol), 2-amino-4-chloro-6-methyl-[1,3,5]triazine (50 mg, 0.35 mmol) and DIPEA (0.2 mL) in 1,4-dioxane (3 mL) afforded the title compound (32 mg, 43%) as an off-white solid. $\delta_H$ (DMSO-d$_6$) 8.26 (1H, d, J=3.0 Hz), 7.95-7.63 (4H, m), 6.67 (2H, m), 5.50-5.25 (1H, m), 4.25-3.20 (9H, m), 2.93-2.80 (1H, m), 2.73-2.64 (1H, m), 2.14 and 2.05 (3H, 2×s). LCMS (ES+) 427 (M+H)$^+$, RT 2.10 minutes (Method 2).

Example 26

4-(3-{(1S)-1-[(4-Amino-[1,3,5]triazin-2-yl)amino] ethyl}-8-chloroquinolin-2-yl)-1-methylpiperazin-2-one Following the procedure described for Example 18, Intermediate 43 (83 mg, 0.26 mmol), 2-amino-4-chloro-[1,3,5] triazine (68 mg, 0.52 mmol) and DIPEA (0.15 mL, 0.83 mmol) in 1,4-dioxane (3 mL) afforded the title compound (35 mg, 33%) as an off-white solid. $\delta_H$ (DMSO-d$_6$) 8.32 (1H, s), 8.19 (1H, d, J=7.36 Hz), 8.03 (1H, s), 7.89-7.76 (2H, m), 7.41 (1H, m), 7.00 (1H, s), 6.94 (1H, s), 5.28 (1H, t, J 7.06 Hz), 4.88 (1H, d, J=17.15 Hz), 4.42 (1H, d, J=17.10 Hz), 4.25-4.06 (2H, m), 3.52 (1H, m), 3.50-3.26 (1H, m), 2.94 (3H, s), 1.34 (3H, d, J=6.58 Hz). LCMS (ES+) 413 (M+H)$^+$, RT 2.42 minutes (Method 1).

Example 27

4-(3-{(1S)-1-[(4-Amino-6-methyl-[1,3,5]triazin-2-yl)amino]ethyl}-8-chloroquinolin-2-yl)-1-methylpip-erazin-2-one Following the procedure described for Example 18, Intermediate 43 (83 mg, 0.26 mmol), 2-amino-4-chloro-6-methyl-[1,3,5]triazine (75 mg, 0.52 mmol) and DIPEA (0.15 mL, 0.83 mmol) in 1,4-dioxane (3 mL) afforded the title compound (72 mg, 67%) as an off-white solid. $\delta_H$ (DMSO-d$_6$) 8.34-8.23 (1H, m), 8.12 (1H, d, J=7.37 Hz), 7.84-7.78 (2H, m), 7.41 (1H, m), 6.87 (2H, m), 5.32-5.24 (1H, m), 4.93 (1H, d, J=17.17 Hz), 4.42 (1H, d, J=17.12 Hz), 4.36-4.25 (1H, m), 4.20-4.08 (1H, m), 3.59-3.47 (1H, m), 3.45-3.36 (1H, m), 3.06-2.84 (3H, m), 2.14 (2H, s), 2.08 (1H, s), 1.40-1.30 (3H, m). LCMS (ES+) 427 (M+H)$^+$, RT 2.26 minutes (Method 2).

Example 28

1-(3-{(1S)-1-[(4-Amino-[1,3,5]triazin-2-yl)amino] ethyl}-8-chloroquinolin-2-yl)-imidazolidin-2-one Following the procedure described for Example 18, Intermediate 44 (54 mg, 0.19 mmol), 2-amino-4-chloro-[1,3,5] triazine (49 mg, 0.37 mmol) and DIPEA (0.1 mL, 0.58 mmol) in 1,4-dioxane (3 mL) afforded the title compound (7 mg, 9%) as an off-white solid. $\delta_H$ (DMSO-d$_6$) 8.21 (1H, s), 7.90-7.80 (2H, m), 7.64 (1H, m), 7.42 (1H, t, J=7.81 Hz), 7.15 (1H, m), 7.00 (1H, s), 6.71 (1H, s), 6.61 (1H, s), 4.75 (1H, m), 4.41 (2H, m), 3.76-3.55 (2H, m), 1.48 (3H, t, J=7.33 Hz). LCMS (ES+) 385 (M+H)$^+$, RT 2.16 minutes (Method 2).

Example 29

(S)-(4-{3-[1-(4-Amino-[1,3,5]triazin-2-ylamino) ethyl]-8-methylquinolin-2-yl}piperazin-1-yl)cyclo-propyl)methanone Intermediate 47 (62 mg, 0.18 mmol) was dissolved in NMP (2 mL) and DIPEA (0.095 mL, 0.55 mmol) was added, followed by 2-amino-4-chloro-[1,3,5]triazine (28 mg, 0.22 mmol). The mixture was heated under microwave irradiation to 150° C. for 1 h. After cooling, the solvents were removed in vacuo. Purification by preparative HPLC gave the title compound (32 mg, 22%) as an off-white solid. $\delta_H$ (CDCl$_3$) 8.15 (1H, s), 7.99 (1H, s), 7.54 (1H, d, J=8.0 Hz), 7.46 (1H, d, J=7.0 Hz), 7.34-7.27 (1H, m), 5.70-5.40 (2H, m), 4.95 (2H, br s), 4.10-3.00 (8H, m), 2.70 (3H, s), 1.84-1.79 (1H, m), 1.55 (3H, s), 1.06-1.01 (2H, m), 0.84-0.77 (2H, m). LCMS (ES+) 433 (M+H)$^+$, RT 3.02 minutes (Method 2).

Example 30

(S)-4-(8-Chloro-3-{1-[4-(methylamino)-[1,3,5]triazin-2-ylamino]ethyl}quinolin-2-yl)piperazin-2-one Intermediate 30 (75 mg, 0.25 mmol) was dissolved in n-butanol (3 mL). DIPEA (0.34 mL, 1.94 mmol) was added, followed by 4-chloro-N-methyl-[1,3,5]triazin-2-amine (71 mg, 0.49 mmol). The mixture was heated under microwave irradiation to 130° C. for 1.5 h. After cooling, the solvents were removed in vacuo. Purification by preparative HPLC gave the title compound (23 mg, 22%). $\delta_H$ (DMSO-d$_6$) 8.40-8.26 (1H, m), 8.20-7.91 (3H, m), 7.86-7.76 (2H, m), 7.45-7.36 (1H, m), 7.32-7.22 (1H, m), 5.47-5.35 and 5.28-5.19 (1H, m), 4.83-3.80 (4H, m), 3.70-3.23 (2H, m), 2.84-2.61 (3H, m), 1.55-1.30 (3H, m). LCMS (ES+) 413 (M+H)$^+$, RT 2.20 minutes (Method 2).

Example 31

1-(3-{(1S)-1-[(4-Amino-6-methyl-[1,3,5]triazin-2-yl)amino]ethyl}-8-methylquinolin-2-yl)-[1,4]diazepan-5-one A mixture of Intermediate 4 (100 mg, 0.31 mmol), [1,4] diazepan-5-one (178 mg, 1.56 mmol) and DIPEA (0.28 mL, 1.56 mmol) in NMP (3 mL) was heated at 140° C. for 4 days. The mixture was poured into water (10 mL) and the aqueous extracted with DCM (2×50 mL). The organic layers were combined, dried (MgSO$_4$), filtered and concentrated in vacuo. The residue was purified by column chromatography on silica, eluting with 5% MeOH in DCM, to give an orange oil. This oil was dissolved in DCM (5 mL) and to this solution was added TFA (2 mL). The mixture was stirred at r.t. for 1 h and the solvent removed in vacuo. To a portion (77 mg, 0.26 mmol) of the resulting product in n-butanol (2 mL) were added 2-amino-4-chloro-6-methyl-[1,3,5]triazine (76 mg, 0.52 mmol) and DIPEA (0.7 mL, 0.54 mmol) and the mixture was heated at 160° C. under microwave irradiation for 1 h. Purification by preparative HPLC afforded the title compound (50 mg, 25%) as a beige solid. $\delta_H$ (CDCl$_3$) 7.99 (1H, s), 7.52 (1H, d, J=8.0 Hz), 7.45 (1H, d, J 7.0 Hz), 7.32-7.25 (1H, m), 6.63-6.50 (1H, m), 5.89-5.72 (1H, m), 5.71-5.09 (3H, m), 3.90-3.24 (3H, m), 3.10 (1H, q, J=7.4 Hz), 3.03-2.92 (1H, m), 2.89-2.78 (1H, m), 2.67 (3H, s), 2.28-1.96 (2H, m), 1.68-1.30 (6H, m). LCMS (ES+) 407 (M+H)$^+$, RT 2.63 minutes (Method 1).

Example 32

1-(3-{(1S)-1-[(4-Amino-[1,3,5]triazin-2-yl)amino]ethyl}-8-methylquinolin-2-yl)-[1,4]-diazepan-5-one A mixture of Intermediate 4 (100 mg, 0.31 mmol), [1,4] diazepan-5-one (178 mg, 1.56 mmol) and DIPEA (0.28 mL, 1.56 mmol) in NMP (3 mL) was heated at 140° C. for 4 days. The mixture was poured into water (10 mL) and the aqueous extracted with DCM (2×50 mL). The organic layers were combined, dried (MgSO$_4$), filtered and concentrated in vacuo. The residue was purified by column chromatography on silica, eluting with 5% MeOH in DCM, to give an orange oil. This oil was dissolved in DCM (5 mL) and to this solution was added TFA (2 mL). The mixture was stirred at r.t. for 1 h and the solvent removed in vacuo. To a portion (50 mg, 0.17 mmol) of the resulting product in n-butanol (2 mL) were added 2-amino-4-chloro-[1,3,5]triazine (40 mg, 0.33 mmol) and DIPEA (0.8 mL, 0.65 mmol) and the mixture was heated at 120° C. overnight. Purification by column chromatography on silica, eluting with 5% methanolic ammonia in DCM, afforded the title compound (15 mg, 20%) as a pale yellow solid. $\delta_H$ (MeOD-d$_4$) 8.16 (1H, s), 8.08-7.97 (1H, m), 7.60 (1H, d, J=8.1 Hz), 7.47 (1H, d, J=7.0 Hz), 7.30 (1H, t, J 7.5 Hz), 5.58-5.52 (1H, m), 3.83-3.24 (6H, m), 3.03-2.92 (1H, m), 2.89-2.78 (1H, m), 2.69 (3H, s), 1.57-1.51 (3H, m). LCMS (ES+) 393 (M+H)$^+$, RT 12.10 minutes (Method 5).

Example 33

6-Methyl-N-{(1S)-1-[8-methyl-2-(piperazin-1-yl)quinolin-3-yl]ethyl}-[1,3,5]triazine-2,4-diamine To a solution of Intermediate 3 (500 mg, 2.26 mmol) in DCM (5 mL) was added trifluoroacetic anhydride (1.0 mL, 4.5 mmol) and the mixture was stirred at r.t. overnight and then washed with 2M NaOH solution (10 mL). The organic layer was separated, dried (MgSO$_4$), filtered and concentrated in vacuo to give an off-white solid. A portion of this solid (100 mg, 0.31 mmol) was dissolved in NMP (2 mL) and to this solution were added tert-butyl 1-piperazinecarboxylate (60 mg, 0.31 mmol) and DIPEA (0.08 mL, 0.65 mmol). The mixture was heated at 140° C. for 3 days. After cooling to r.t., NaOH solution (2M; 2 mL) was added and the mixture stirred overnight. The mixture was poured into water (10 mL) and extracted with Et$_2$O (3×20 mL). The organics were combined, dried (MgSO$_4$), filtered and concentrated in vacuo to give an orange oil. A portion of this oil (50 mg, 0.135 mmol) was dissolved in n-butanol (2 mL) and to this solution were added 2-amino-4-chloro-6-methyl-[1,3,5]triazine (38 mg, 0.27 mmol) and DIPEA (0.35 mL, 0.27 mmol). The mixture was heated at 160° C. under microwave irradiation for 1 h. The solvent was removed in vacuo and the residue was purified by preparative HPLC to give an off-white solid. This solid (12 mg, 0.025 mmol) was dissolved in DCM (5 mL) and treated with TFA (0.5 mL) at r.t. overnight. The mixture was washed with 2M NaOH solution (3×20 mL), and the organic layer was separated, dried (MgSO$_4$), filtered and concentrated in vacuo to give the title compound (9.2 mg, 8%) as a white solid. $\delta_H$ (CDCl$_3$) 7.94 (1H, s), 7.51 (1H, d, J=8.1 Hz), 7.44 (1H, d, J=7.1 Hz), 7.30-7.21 (1H, m), 5.67-5.38 (2H, m), 4.95 (2H, br s), 3.76-3.48 (2H, m), 3.19-3.00 (4H, m), 2.71 (3H, s), 2.33-2.14 (3H, m), 1.78 (3H, br s), 1.55-1.43 (3H, m). LCMS (ES−) 377 (M−H)$^-$, RT 2.50 minutes (Method 1).

Example 34

(S)-(4-{3-[1-(4-Amino-6-methyl-[1,3,5]triazin-2-ylamino)ethyl]-8-chloroquinolin-2-yl}piperazin-1-yl)(cyclopropyl)methanone Intermediate 49 (65 mg, 0.18 mmol) was dissolved in NMP (2 mL). DIPEA (0.065 mL, 0.36 mmol) was added, followed by 2-amino-4-chloro-6-methyl-[1,3,5]-triazine (31 mg, 0.22 mmol). The mixture was heated under microwave irradiation to 150° C. for 1 h. After cooling, the solvents were removed in vacuo. Purification by preparative HPLC gave the title compound (32 mg, 84%) as a pale brown solid. $\delta_H$ (DMSO-$d_6$) 8.35-8.30 (1H, m), 7.92 (1H, d, J=8.0 Hz), 7.93-7.78 (2H, m), 7.42 (1H, t, J=7.8 Hz), 6.65 (2H, br s), 5.55-5.43 m), 4.08 (1H, br s), 3.82 (2H, br s), 3.73 (2H, br s), 3.63 (1H, s), 3.16 (1H, br s), 3.10 (1H, m), 2.07 (1H, br s), 1.41 (3H, d, J=6.5 Hz), 0.84-0.76 (4H, m). LCMS (ES+) 467 (M+H)$^+$, RT 2.44 minutes (Method 2).

Example 35

(S)-(4-{3-[1-(4-Amino-[1,3,5]triazin-2-ylamino)ethyl]-8-chloroquinolin-2-yl}piperazin-1-yl)(cyclopropyl)methanone Following the procedure described for Example 34, Intermediate 49 (65 mg, 0.18 mmol), NMP (2 mL), DIPEA (0.065 mL, 0.36 mmol) and 2-amino-4-chloro-[1,3,5]-triazine (28 mg, 0.22 mmol) gave the title compound (21 mg, 26%) as an off-white solid after further purification by column chromatography on silica, eluting with 0-6% MeOH in EtOAc. $\delta_H$ (CDCl$_3$) 8.25 (1H, s), 8.19 (1H, s), 7.74 (1H, d, J=7.4 Hz), 7.69 (1H, d, J=8.6 Hz), 7.38-7.30 (1H, m), 7.13 (1H, br s), 5.51 (1H, br s), 3.90 (2H, br s), 3.67 (4H, br s), 3.44 (2H, br s), 1.83 (1H, s), 1.65 (3H, s), 1.13-0.88 (2H, m), 0.83-0.45 (2H, m). LCMS (ES+) 453 (M+H)$^+$, RT 2.61 minutes (Method 2).

Example 36

(S)-2-(4-{3-[1-(4-Amino-6-methyl-[1,3,5]triazin-2-ylamino)ethyl]-8-methylquinolin-2-yl}piperazin-1-yl)-N,N-dimethylacetamide Following the procedure described for Example 34, Intermediate 51 (85 mg, 0.24 mmol), NMP (2 mL), DIPEA (0.083 mL, 0.48 mmol) and 2-amino-4-chloro-6-methyl-[1,3,5]triazine (41 mg, 0.29 mmol) gave the title compound (42 mg, 38%) as a brown gum. $\delta_H$ (DMSO-$d_6$) 8.22-8.13 (1H, m), 7.86-7.70 (1H, m), 7.62 (1H, d, J=8.1 Hz), 7.49 (1H, d, J=6.9 Hz), 7.35-7.29 (1H, m), 6.75-6.50 (2H, m), 5.56-5.35 m), 3.83-3.57 (4H, m), 3.27 (2H, s), 3.15-3.00 (5H, m), 2.87 (3H, s), 2.76-2.70 (2H, m), 2.66 (3H, s), 2.09 (3H, d, J=33.1 Hz), 1.40-1.37 (3H, m). LCMS (ES+) 464 (M+H)$^+$, RT 16.36 minutes (Method 6).

Example 37

(S)-2-(4-{3-[1-(4-Amino-6-methyl-[1,3,5]triazin-2-ylamino)ethyl]-8-methylquinolin-2-yl}piperazin-1-yl)-1-(morpholin-4-yl)ethanone Following the procedure described for Example 34, Intermediate 53 (70 mg, 0.16 mmol), NMP (2 mL), DIPEA (0.14 mL, 0.8 mmol) and 2-amino-4-chloro-6-methyl-[1,3,5]triazine (28 mg, 0.19 mmol) gave the title compound (19 mg, 23%) as an off-white glass. $\delta_H$ (CDCl$_3$) 8.02-7.93 (1H, m), 7.55 (1H, d, J=7.9 Hz), 7.47 (1H, d, J=6.9 Hz), 7.31 (1H, d, J=7.6 Hz), 6.11 (1H, br s), 5.65-5.05 (3H, m), 3.80-3.60 (10H, m), 3.43-3.35 (2H, m), 3.30-3.17 (2H, m), 2.98-2.75 (4H, m), 2.73 (3H, s), 2.32-2.23 (3H, m), 1.56-1.44 (3H, m). LCMS (ES+) 506 (M+H)$^+$, RT 2.51 minutes (Method 1).

Example 38

(S)-N$^2$-(1-{8-Chloro-2-[4-methylsulfonyl)piperazin-1-yl]quinolin-3-yl}ethyl)-6-methyl-[1,3,5]triazine-2,4-diamine Following the procedure described for Example 34, Intermediate 55 (85 mg, 0.23 mmol), NMP (2 mL), DIPEA (0.08 mL, 0.46 mmol) and 2-amino-4-chloro-6-methyl-[1,3,5]triazine (40 mg, 0.27 mmol) gave the title compound (43 mg, 39%) as a pale yellow solid. $\delta_H$ (DMSO-$d_6$) 8.31 (1H, d, J=5.8 Hz), 7.95 (1H, d, J=8.0 Hz), 7.83 (2H, d, J=7.7 Hz), 7.43 (1H, t, J=7.8 Hz), 6.72 (1H, br s), 6.62 (1H, br s), 5.46-5.37 (1H, m), 3.76 (2H, s), 3.49 (2H, s), 3.42-3.28 (2H, m), 3.28-3.16 (2H, m), 3.01 (3H, s), 2.14 (3H, s), 1.39 (3H, d, J=6.6 Hz). LCMS (ES+) 477 (M+H)$^+$, RT 2.86 minutes (Method 1).

Example 39

(S)-Ethyl 2-(4-{3-[1-(4-amino-6-methyl-[1,3,5]triazin-2-ylamino)ethyl]-8-chloroquinolin-2-yl}piperazin-1-yl)acetate Intermediate 57 (120 mg, 0.24 mmol) was dissolved in n-butanol (3 mL). DIPEA (0.17 mL, 0.97 mmol) was added, followed by 2-amino-4-chloro-6-methyl-[1,3,5]triazine (41 mg, 0.29 mmol). The mixture was heated under microwave irradiation to 130° C. for 1 h. After cooling, the solvents were removed in vacuo. Purification by preparative HPLC gave the title compound (38 mg, 32%) as an off-white solid. $\delta_H$ (CDCl$_3$) 8.01 (1H, s), 7.71 (1H, d, J=7.5 Hz), 7.61 (1H, d, J=7.9 Hz), 7.29 (1H, t, J 5.5), 6.15 (1H, br s), 5.52 (2H, s), 5.39 (1H, s), 4.24 (2H, dd, J 14.2, 7.1 Hz), 3.77 (2H, s), 3.41 (4H, s), 2.99 (2H, d, J=7.7 Hz), 2.92 (2H, s), 2.34 (3H, s), 1.55 (3H, s), 1.32 (3H, t, J=7.1 Hz). LCMS (ES+) 485 (M+H)$^+$, RT 2.79 minutes (Method 1).

Example 40

(S)-2-(4-{3-[1-(4-Amino-[1,3,5]triazin-2-ylamino)ethyl]-8-chloroquinolin-2-yl}piperazin-1-yl)-N,N-dimethylacetamide Following the procedure described for Example 39, Intermediate 59 (62 mg, 0.17 mmol), n-butanol (2 mL), DIPEA (0.057 mL, 0.33 mmol) and 2-amino-4-chloro-[1,3,5]-triazine (26 mg, 0.20 mmol) gave the title compound (40 mg, 53%) as a pale yellow solid. $\delta_H$ (CDCl$_3$) 8.14 (1H, s), 8.01 (1H, s), 7.71 (1H, dd, J 7.5, 1.3 Hz), 7.61 (1H, d, J=8.0 Hz), 7.33-7.26 (1H, m), 5.75 (1H, br s), 5.51-5.44 (1H, m), 5.22 (1H, br s), 5.07 (1H, br s), 3.87 (2H, s), 3.50 (4H, s), 3.15 (3H, s), 3.05 (2H, d, J=10.3 Hz), 3.00 (3H, s), 1.53 (3H, d, J=6.5 Hz). LCMS (ES+) 470 (M+H)$^+$, RT 7.04 minutes (Method 8).

Example 41

(S)-N$^2$-(4-Methoxybenzyl)-6-methyl-N$^4$-{1-[8-methyl-2-(pyrrolidin-1-yl)quinolin-3-yl]ethyl}-[1,3,5]triazine-2,4-diamine Intermediate 28 (79.5 mg, 0.31 mmol), 4-chloro-N-(4-methoxybenzyl)-6-methyl-[1,3,5]triazine-2-amine (123 mg, 0.47 mmol), DIPEA (0.277 mL, 0.48 mmol) and n-butanol (2.5 mL) were combined in a sealed tube and heated under microwave irradiation to 140° C. for 1.5 h. After cooling, the n-butanol was removed in vacuo. Purification by column chromatography on silica, eluting with 20% MeOH in DCM, gave a brown oil (204 mg). Further purification by preparative HPLC gave the title compound (64 mg, 43%) as a yellow solid. $\delta_H$ (DMSO-d$_6$) 8.12 (1H, s), 7.51 (1H, d, J=8.05 Hz), 7.40 (1H, d, J=8.05 Hz), 7.19-7.13 (4H, m), 6.90-6.88 (1H, m), 6.79-6.77 (2H, d, J=8.05 Hz), 5.76 5.72 (1H, m), 4.50-4.38 (2H, m), 3.79-3.68 (7H, m), 2.63 (3H, s), 2.15 (3H, s), 1.99-1.88 (4H, m), 1.51 (3H, s, J=6.57 Hz). LCMS (ES+) 484 (M+H)$^+$, RT 2.13 minutes (Method 2).

Example 42

(S)-4-(3-{1-[4-(4-Methoxybenzylamino)-6-methyl-[1,3,5]triazin-2-ylamino]ethyl}-8-methylquinolin-2-yl)piperazin-2-one Intermediate 7 (75.9 mg, 0.267 mmol), 4-chloro-N-(4-methoxybenzyl)-6-methyl-[1,3,5]triazine-2-amine (106 mg, 0.40 mmol), DIPEA (0.335 mL, 1.87 mmol) and n-butanol (2.5 mL) were combined in a sealed tube and heated under microwave irradiation to 140° C. for 1.5 h. After cooling, the excess n-butanol was concentrated in vacuo. Purification by column chromatography on silica, eluting with 10% MeOH in DCM, gave a pale yellow oil (70 mg). Further purification by preparative HPLC gave the title compound (30 mg, 22%) as a white solid. $\delta_H$(DMSO-d$_6$) 8.20 (1H, s), 7.60 (1H, d, J 7.2 Hz), 7.47 (1H, d, J=6.8 Hz), 7.32-7.22 (2H, m), 7.17 (2H, d, J=7.2 Hz), 7.10 (1H, br s), 6.85 (1H, br s), 6.78 (2H, d, J=7.6 Hz), 5.57 5.51 (1H, m), 4.48-4.35 (2H, m), 4.17 (1H, d, J=16.8 Hz), 3.89 (1H, d, J=16.8 Hz), 3.82-3.76 (1H, m), 3.71 (3H, s), 3.53-3.39 (2H, m), 3.37-3.27 (1H, m), 2.67 (3H, s), 2.13 (3H, s), 1.48 (3H, d, J=6.8 Hz). LCMS (ES+) 513 (M+H)$^+$, RT 2.35 minutes (Method 2).

Example 43

N-{(1S)-1-[7-Fluoro-2-(pyrrolidin-1-yl)quinolin-3-yl]ethyl}-[1,3,5]triazine-2,4-diamine A mixture of Intermediate 26 (324 mg, 1.0 mmol), pyrrolidine (142 mg, 2.0 mmol) and DIPEA (0.28 mL, 2.0 mmol) in n-butanol (2 mL) was heated at 120° C. for 3 days. The solvent was removed in vacuo and the residue purified by column chromatography on silica, eluting with Et$_2$O, to give a yellow oil. This was dissolved in MeOH (5 mL) and to this solution was added 4M HCl in 1,4-dioxane (2 mL). The mixture was stirred at r.t. overnight and the solvent removed in vacuo. To a portion (100 mg, 0.39 mmol) of the resulting product in n-butanol (2 mL) were added 2-amino-4-chloro-[1,3,5]triazine (55 mg, 0.43 mmol) and DIPEA (0.2 mL) and the mixture was heated at 110° C. overnight. Purification by preparative HPLC afforded the title compound (14 mg, 8%) as an off-white solid. $\delta_H$ (CDCl$_3$) 8.20-8.13 (1H, m), 7.86 (1H, s), 7.54 (1H, dd, J 8.8, 6.3 Hz), 7.34 (1H, dd, J 10.9, 2.6 Hz), 7.00-6.94 (1H, m), 5.57-5.42 (1H, m), 5.00 (2H, br s), 3.81-3.74 (2H, m), 3.76-3.64 (3H, m), 2.09-1.88 (4H, m), 1.48 (3H, d, J=6.21 Hz). LCMS (ES+) 354 (M+H)$^+$, RT 17.54 minutes (Method 6).

Example 44

N-[1-(3-{(1S)-1-[(4-Amino-[1,3,5]triazin-2-yl)amino]ethyl}-7-fluoroquinolin-2-yl)-piperidin-4-yl]acetamide A mixture of Intermediate 26 (324 mg, 1.0 mmol), 4-(acetylamino)piperidine (284 mg, 2.0 mmol) and DIPEA (0.28 mL, 2.0 mmol) in n-butanol (2 mL) was heated at 120° C. for 3 days. The solvent was removed in vacuo and the residue purified by column chromatography on silica, eluting with Et$_2$O, to give a yellow oil. This was dissolved in MeOH (5 mL) and to this solution was added 4M HCl in 1,4-dioxane (2 mL). The mixture was stirred at r.t. overnight and the solvent removed in vacuo. To a portion (100 mg, 0.3 mmol) of the resulting product in n-butanol (2 mL) were added 2-amino-4-chloro-[1,3,5]triazine (44 mg, 0.34 mmol) and DIPEA (0.2 mL) and the mixture was heated at 110° C. overnight. Purification by preparative HPLC afforded the title compound (40 mg, 18%) as a pale yellow solid. $\delta_H$ (CDCl$_3$) 8.11 (1H, s), 7.95 (1H, s), 7.63 (1H, dd, J 8.9, 6.1 Hz), 7.49 (1H, dd, J 10.4, 2.5 Hz), 7.15 (1H, m), 6.06 (1H, s), 5.53 (1H, s), 5.37 (1H, s), 5.20 (2H, s), 4.07-3.98 (1H, m), 3.88 (1H, s), 3.49 (1H, m), 3.32 (1H, t, J=11.7 Hz), 2.92 (1H, t, J=11.5 Hz), 2.17-2.07 (2H, m), 2.17-1.90 (3H, m), 1.78-1.58 (2H, m), 1.51 (3H, d, J=6.7 Hz). LCMS (ES+) 425 (M+H)$^+$, RT 7.08 minutes (Method 8).

Example 45

N-{(1S)-1-[7-Fluoro-2-(pyrrolidin-1-yl)quinolin-3-yl]ethyl}-6-methyl-[1,3,5]triazine-2,4-diamine A mixture of Intermediate 26 (324 mg, 1.0 mmol), pyrrolidine (142 mg, 2.0 mmol) and DIPEA (0.28 mL, 2.0 mmol) in n-butanol (2 mL) was heated at 120° C. for 3 days. The solvent was removed in vacuo and the residue purified by column chromatography on silica, eluting with Et$_2$O, to give a yellow oil. This was dissolved in MeOH (5 mL) and to this solution was added 4M HCl in 1,4-dioxane (2 mL). The mixture was stirred at r.t. overnight and the solvent removed in vacuo. To a portion (57 mg, 0.22 mmol) of the resulting product in n-butanol (1 mL) were added 2-amino-4-chloro-6-methyl-[1,3,5]triazine (36 mg, 0.25 mmol) and DIPEA (64 mg, 0.5 mmol) and the mixture was heated at 160° C. under microwave irradiation for 1 h. Purification by preparative HPLC afforded the title compound (29 mg, 94%) as an off-white solid. $\delta_H$ (CDCl$_3$) 7.86 (1H, s), 7.56-7.48 (1H, m), 7.34 (1H, dd, J 10.9, 2.5 Hz), 6.99-6.92 (1H, m), 5.84-5.16 (4H, m), 3.91-3.61 (4H, m), 2.44-1.78 (7H, m), 1.44 (3H, m). LCMS (ES+) 368 (M+H)$^+$, RT 2.95 minutes (Method 1).

Example 46

N-[1-(3-{(1S)-1-[(4-Amino-6-methyl-[1,3,5]triazin-2-yl)amino]ethyl}-7-fluoroquinolin-2-yl)piperidin-4-yl]acetamide A mixture of Intermediate 26 (324 mg, 1.0 mmol), 4-(acetylamino)piperidine (284 mg, 2.0 mmol) and DIPEA (0.28 mL, 2.0 mmol) in n-butanol (2 mL) was heated at 120° C. for 3 days. The solvent was removed in vacuo and the residue purified by column chromatography on silica, eluting with Et$_2$O, to give a yellow oil. This was dissolved in MeOH (5 mL) and to this solution was added 4M HCl in 1,4-dioxane (2 mL). The mixture was stirred at r.t. overnight and the solvent removed in vacuo. To a portion (73 mg, 0.22 mmol) of the resulting product in n-butanol (1 mL) were added 2-amino-4-chloro-6-methyl-[1,3,5]triazine (36 mg, 0.25 mmol) and DIPEA (64 mg, 0.5 mmol) and the mixture was heated at 160° C. under microwave irradiation for 1 h. Purification by preparative HPLC afforded the title compound (50 mg, 30%)$_{as}$ an off-white solid. $\delta_H$ (CDCl$_3$) 8.03-7.95 (1H, m), 7.69-7.61 (1H, m), 7.49 (1H, dd, J 10.4, 2.5 Hz), 7.18-7.11 (1H, m), 5.80-5.24 (4H, m), 4.08-3.80 (2H, m), 3.57-3.42

(1H, m), 3.37-3.27 (1H, m), 2.98-2.86 (1H, m), 2.29-2.03 (5H, m), 1.81-1.60 (2H, m), 1.53-1.49 (3H, m). LCMS (ES+) 439 (M+H)+, RT 1.90 minutes (Method 2).

Example 47

1-[4-(3-{(1S)-1-[(4-Amino-6-methyl-[1,3,5]triazin-2-yl)amino]ethyl}-7-fluoroquinolin-2-yl)piperazin-1-yl]ethanone A mixture of Intermediate 26 (324 mg, 1.0 mmol), 1-acetylpiperazine (256 mg, 2.0 mmol) and DIPEA (0.28 mL, 2.0 mmol) in n-butanol (2 mL) was heated at 120° C. for 3 days. The solvent was removed in vacuo and the residue purified by column chromatography on silica, eluting with Et$_2$O, to give a yellow oil. This was dissolved in MeOH (5 mL) and to this solution was added 4M HCl in 1,4-dioxane (2 mL). The mixture was stirred at r.t. overnight and the solvent removed in vacuo. To a portion (70 mg, 0.22 mmol) of the resulting product in n-butanol (1 mL) were added 2-amino-4-chloro-6-methyl-[1,3,5]triazine (36 mg, 0.25 mmol) and DIPEA (64 mg, 0.5 mmol) and the mixture was heated at 160° C. under microwave irradiation for 1 h. Purification by preparative HPLC afforded the title compound (4.2 mg, 4%) as an off-white solid. $\delta_H$ (CDCl$_3$) 8.05-7.95 (1H, m), 7.71-7.63 (1H, m), 7.50 (1H, dd, J 10.3, 2.5 Hz), 7.18 (1H, dt, J 10.8, 4.1 Hz), 5.60-4.90 (3H, m), 3.97-3.87 (1H, m), 3.84-3.50 (6H, m), 3.28-3.18 (1H, m), 3.11-3.01 (1H, m), 2.44-2.02 (6H, m), 1.56-1.47 (3H, LCMS (ES+) 425 (M+H)+, RT 4.32 minutes (Method 1).

Example 48

1-[4-(3-{(1S)-1-[(4-Amino-[1,3,5]triazin-2-yl)amino]ethyl}-7-fluoroquinolin-2-yl)-piperazin-1-yl]ethanone A mixture of Intermediate 26 (324 mg, 1.0 mmol), 1-acetylpiperazine (256 mg, 2.0 mmol) and DIPEA (0.28 mL, 2.0 mmol) in n-butanol (2 mL) was heated at 120° C. for 3 days. The solvent was removed in vacuo and the residue purified by column chromatography on silica, eluting with Et$_2$O, to give a yellow oil. This was dissolved in MeOH (5 mL) and to this solution was added 4M HCl in 1,4-dioxane (2 mL). The mixture was stirred at r.t. overnight and the solvent removed in vacuo. To a portion (100 mg, 0.31 mmol) of the resulting product in n-butanol (1 mL) were added 2-amino-4-chloro-[1,3,5]triazine (45 mg, 0.34 mmol) and DIPEA (0.2 mL) and the mixture was heated at 160° C. under microwave irradiation for 1 h. Purification by preparative HPLC afforded the title compound (11 mg, 9%) as an off-white solid. $\delta_H$ (CDCl$_3$) 8.19 (1H, s), 8.01 (1H, s), 7.67 (1H, dd, J 8.9, 6.0 Hz), 7.50 (1H, dd, J 10.3, 2.5 Hz), 7.18 (1H, td, J 8.6, 2.6 Hz), 5.71-5.04 (3H, m), 3.93-3.47 (6H, m), 3.27-2.97 (2H, m), 2.16 (3H, s), 1.52 (3H, d, J=6.6 Hz). LCMS (ES+) 411 (M+H)+, RT 14.46 minutes (Method 6).

Example 49

4-{[8-Methyl-2-(pyrrolidin-1-yl)quinolin-3-yl]methoxy}-[1,3,5]triazin-2-amine

Intermediate 60 (100 mg, 0.39 mmol) and 2-amino-4-chloro-[1,3,5]triazine (61 mg, 0.47 mmol) were combined in DMF (2 mL). NaH (60% suspension in mineral oil, 34 mg, 0.86 mmol) was added and the resulting mixture was heated at 80° C. overnight. After cooling, Et$_2$O (10 mL) was added and the mixture was washed with water and brine. The organic layer was dried (MgSO$_4$), filtered and the solvent was removed in vacuo. Purification by column chromatography on silica, eluting with 30-50% EtOAc in isohexane, gave the title compound (9.1 mg, 9.6%). $\delta_H$ (CDCl$_3$) 8.41 (1H, s), 8.02 (1H, s), 7.49-7.37 (2H, m), 7.11 (1H, t, J=7.50 Hz), 5.50 (2H, s), 3.75 (4H, t, J=6.27 Hz), 2.64 (2H, s), 2.03-1.96 (4H, m), 1.90-1.74 (3H, m). LCMS (ES+) 337 (M+H)+, RT 3.93 minutes (Method 1).

Example 50

4-{[8-Methyl-2-(morpholin-4-yl)quinolin-3-yl]methoxy}-[1,3,5]triazin-2-amine

Intermediate 61 (200 mg, 0.78 mmol) and 2-amino-4-chloro-[1,3,5]triazine (120 mg, 0.93 mmol) were combined in 1,4-dioxane (3 mL). NaH (60% suspension in mineral oil, 37 mg, 0.93 mmol) was added and the resulting mixture was heated at 80° C. overnight. After cooling, Et$_2$O (10 mL) was added and the mixture was washed with water and brine. The organic layer was dried (MgSO$_4$), filtered and the solvent was removed in vacuo. Purification by column chromatography on silica, eluting with 50-100% EtOAc in isohexane, gave the title compound (5.1 mg, 1.8%). $\delta_H$ (CDCl$_3$) 8.43 (1H, s), 8.21 (1H, s), 7.56 (1H, d, J=8.1 Hz), 7.48 (1H, d, J 7.0 Hz), 7.29 (1H, d, J=7.6 Hz), 5.55 (2H, s), 5.37 (2H, s), 3.92 (4H, t, J=4.55 Hz), 3.38 (4H, t, J=4.56 Hz), 2.71 (3H, s). LCMS (ES+) 353 (M+H)+, RT 3.47 minutes (Method 1).

Example 51

4-{3-[(4-Amino-[1,3,5]triazin-2-ylamino)methyl]-8-methylquinolin-2-yl}piperazin-2-one Intermediate 65 (100 mg, 0.37 mmol) was dissolved in NMP (1.5 mL). DIPEA (0.32 mL, 0.19 mmol) was added, followed by 2-amino-4-chloro-[1,3,5]triazine (97 mg, 0.74 mmol). The mixture was heated under microwave irradiation to 150° C. for 1 h. After cooling, the solvents were removed in vacuo. Purification by preparative HPLC gave the title compound (21 mg, 16%) as a pale brown solid. $\delta_H$ (DMSO-d$_6$) 8.08 (1H, s), 8.03 (1H, s), 7.95 (1H, d, J=14.44 Hz), 7.89 (1H, s), 7.75-7.65 (1H, m), 7.52 (1H, d, J=6.98 Hz), 7.32 (1H, t, J=7.54 Hz), 6.88 (2H, m), 4.68-4.60 (2H, m), 4.03 (1H, s), 3.94 (1H, s), 3.51 (2H, s), 3.39-3.35 (2H, m), 2.66 (3H, s). LCMS (ES+) 365 (M+H)+, RT 7.22 minutes (Method 8).

Example 52

4-{3-[(4-Amino-6-methyl-[1,3,5]triazin-2-ylamino)methyl]-8-methylquinolin-2-yl}-piperazin-2-one Following the procedure described for Example 51, Intermediate 65 (100 mg, 0.37 mmol), NMP (1.5 mL), DIPEA (0.32 mL, 0.19 mmol) and 2-amino-4-chloro-6-methyl-[1,3,5]triazine (106 mg, 0.74 mmol) gave the title compound (64 mg, 46%). $\delta_H$ (CDCl$_3$) 8.00 (1H, s), 7.53 (1H, d, J=8.1 Hz), 7.47 (1H, d, J=7.0 Hz), 7.30 (1H, t, J=7.4 Hz), 6.17 (1H, s), 5.93 (1H, d, J 7.1 Hz), 4.74 (2H, s), 4.35 (1H, s), 3.63 (3H, s), 2.69 (3H, s), 2.29 (3H, s), 1.70 (3H, s). LCMS (ES+) 476 (M+H)+, RT 7.21 minutes (Method 8).

Example 53

(S)-1-(4-{3-[1-(4-Amino-[1,3,5]-triazin-2-ylamino)ethyl]-8-methylquinolin-2-yl}-piperazin-1-yl)ethanone Intermediate 67 (100 mg, 0.32 mmol), 2-amino-4-chloro-[1,3,5]triazine (50 mg, 0.38 mmol), DIPEA (0.29 mL, 1.60 mmol) and NMP (2 mL) were combined in a sealed tube and heated under microwave irradiation to 120° C. for 1 h. After cooling, the reaction mixture was dissolved in a 1:1 mixture of EtOAc and Et$_2$O (200 mL) and washed with saturated brine (3×50 mL). The organic layer was dried (MgSO$_4$) and concentrated in vacuo. Purification by column chromatography on silica, eluting with 10% MeOH in DCM, afforded the title compound (45 mg, 35%) as a white solid. $\delta_H$(CDCl$_3$) 8.15-8.05 (1H, m), 8.05-7.95 (1H, m), 7.53 (1H, d, J=8.05 Hz), 7.47 (1H, d, J=8.05 Hz), 7.33-7.27 (1H, m), 6.55-6.50 (1H, m), 5.62-5.40 (3H,m), 4.00-3.86 (1H, m), 3.85-3.65 (3H, m), 3.61 (2H, d, J=10.77 Hz), 3.30-3.16 (1H, m), 3.15-3.05 (1H, m), 2.71 (3H, s), 2.16 (3H, s), 1.54 (3H, d, J=6.57 Hz). LCMS (ES+) 407 (M+H)+, RT 2.80 minutes (Method 1).

Example 54

4-{3-[(4-Amino-[1,3,5]triazin-2-yloxy)methyl]-8-methylquinolin-2-yl}piperazin-2-one Intermediate 68 (80 mg, 0.29 mmol) was suspended in 1,4-dioxane (5 mL) and NaH (30 mg, 0.74 mmol; 60% dispersion in mineral oil) was added. The reaction mixture was heated at 80° C. for 15 minutes. 2-Amino-4-chloro-[1,3,5]triazine (58 mg, 0.44 mmol) was added and the mixture was heated at 80° C. for a further 5 h. After cooling, the mixture was dissolved in EtOAc (100 mL) and washed with water (20 mL) and brine (20 mL). The organic layer was dried (MgSO$_4$), filtered and concentrated in vacuo. Purification by column chromatography on silica, eluting with 0-10% MeOH in DCM, afforded the title compound (52 mg, 49%) as a cream solid. $\delta_H$ (DMSO-d$_6$) 8.34 (2H, d, J=8.71 Hz), 7.95 (1H, s), 7.76 (1H, d, J=8.02 Hz), 7.64 (1H, s), 7.61-7.55 (2H, m), 7.37 (1H, t, J=7.53 Hz), 5.54 (2H, s), 3.97 (2H, s), 3.56 (2H, t, J=5.24 Hz), 2.67 (3H, s), 2.54 (2H, under DMSO). LCMS (ES+) 366 (M+H)+, RT 2.44 minutes (Method 1).

Example 55

4-{3-[(4-Amino-6-methyl-[1,3,5]triazin-2-yloxy)methyl]-8-methylquinolin-2-yl}-piperazin-2-one Intermediate 68 (50 mg, 0.18 mmol) was suspended in 1,4-dioxane (5 mL) and NaH (18 mg, 0.45 mmol; 60% dispersion in mineral oil) was added. The reaction mixture was heated at 80° C. for 15 minutes. 2-Amino-4-chloro-6-methyl-[1,3,5]triazine (40 mg, 0.28 mmol) was added and the mixture was heated at 80° C. for a further 5 h. After cooling, the mixture was dissolved in EtOAc (100 mL) and washed with water (20 mL) and brine (20 mL). The organic layer was dried (MgSO$_4$), filtered and concentrated in vacuo. Purification by column chromatography on silica, eluting with 0-10% MeOH in DCM, afforded the title compound (34 mg, 50%) as a white solid. $\delta_H$ (DMSO-d$_6$) 8.34 (1H, s), 7.95 (1H, s), 7.70 (1H, d, J=8.0 Hz), 7.57 (1H, d, J=8.0 Hz), 7.53-7.43 (2H, m), 7.37 (1H, t, J=8.0 Hz), 5.52 (2H, s), 3.97 (2H, s), 3.60-3.53 (2H, m), 2.66 (3H, s), 2.54 (2H, under DMSO), 2.28 (3H, s). LCMS (ES+) 380 (M+H)+, RT 2.49 minutes (Method 1).

Example 56

(S)-4-(8-Chloro-3-{1-[4-(dimethylamino)-[1,3,5]triazin-2-ylamino]ethyl}quinolin-2-yl)piperazin-2-one Following the procedure described for Example 30, Intermediate 30 (75 mg, 0.24 mmol), 4-chloro-N,N-dimethyl-[1,3,5]triazin-2-amine (78 mg, 0.49 mmol) and DIPEA (0.34 mL, 1.92 mmol) in n-butanol (3.0 mL) afforded the title compound (23.1 mg, 23%) as a pale yellow solid. $\delta_H$ (DMSO-d$_6$) 8.34 (1H, s), 8.12-7.91 (3H, m), 7.82 (2H, d, J=7.60 Hz), 7.45-7.37 (1H, m), 5.47-5.30 (1H, m), 4.22-3.23 (6H, m), 3.20-2.85 (6H, m), 1.58-1.39 (3H, m). LCMS (ES+) 427 (M+H)+, 2.28 minutes (Method 2).

Example 57

(S)-N$^2$-{1-[8-Chloro-2-(3,3-difluoropyrrolidin-1-yl)quinolin-3-yl]ethyl}-[1,3,5]triazine-2,4-diamine Similarly, Intermediate 69 (76 mg, 0.24 mmol), 2-amino-4-chloro-[1,3,5]triazine (35 mg, 0.27 mmol) and DIPEA (0.15 mL, 0.85 mmol) in n-butanol (2.0 mL) afforded the title compound (26.1 mg, 27%) as a pale yellow solid. $\delta_H$ (DMSO-d$_6$) 8.26-8.17 (1H, m), 8.06-7.94 (1H, m), 7.86-7.71 (2H, m), 7.34-7.25 (1H, m), 6.90-6.60 (2H, m), 5.56-5.46 (1H, m), 4.40-4.22 (1H, m), 4.15-3.93 (2H, m), 2.60-2.50 (3H, m), 1.45-1.39 (3H, m), one NH not visible. LCMS (ES+) 406 (M+H)+, 3.03 minutes (Method 2).

Example 58

(S)-N$^2$-{1-[8-Chloro-2-(3,3-difluoropyrrolidin-1-yl)quinolin-3-yl]ethyl}-6-methyl-[1,3,5]triazine-2,4-diamine Similarly, Intermediate 69 (76 mg, 0.24 mmol), 2-amino-4-chloro-6-methyl-[1,3,5]triazine (39 mg, 0.27 mmol) and DIPEA (0.15 mL, 0.85 mmol) in n-butanol (2.0 mL) afforded the title compound (55.3 mg, 54%) as a pale yellow solid. $\delta_H$ (DMSO-d$_6$) 8.28-8.16 (1H, m), 7.94-7.72 (3H, m), 7.30 (1H, t, J=7.78 Hz), 6.94-6.27 (2H, m), 5.61-5.46 (1H, m), 4.41-3.94 (5H,m), 2.61-2.51 (1H, m), 2.19-2.02 (3H, m), 1.40 (3H, d, J=6.69 Hz). LCMS (ES+) 420 (M+H)+, 2.69 minutes (Method 2).

Example 59

N$^2$-[(S)-1-{8-Chloro-2-[(R)-3-fluoropyrrolidin-1-yl]quinolin-3-yl}ethyl]-[1,3,5]triazine-2,4-diamine Similarly, Intermediate 70 (84 mg, 0.29 mmol), 2-amino-4-chloro-[1,3,5]triazine (41 mg, 0.35 mmol) and DIPEA (0.15 mL, 0.85 mmol) in n-butanol (2.0 mL) afforded the title compound (42.5 mg, 38%) as a pale yellow solid. $\delta_H$ (DMSO-d$_6$) 8.23 (1H, s), 8.04-7.86 (1H, m), 7.75-7.66 (2H, m), 7.26-7.18 (1H, m), 6.98-6.49 (2H, m), 5.74-5.65 (1H, m), 5.60-5.55 & 5.47-5.41 (1H, 2×m), 4.21-3.89 (4H, m), 2.35-2.15

(2H, m), 1.57-1.49 (3H, m), 1H under solvent peak. LCMS (ES+) 388 (M+H)+, 3.20 minutes (Method 1).

Example 60

N²-[(S)-1-{8-Chloro-2-[(R)-3-fluoropyrrolidin-1-yl]quinolin-3yl}ethyl]-6-methyl-[1,3,5]triazine-2,4-diamine Similarly, Intermediate 70 (84 mg, 0.29 mmol), 2-amino-4-chloro-6-methyl-[1,3,5]triazine (45 mg, 0.35 mmol) and DIPEA (0.15 mL, 0.85 mmol) in n-butanol (2.0 mL) afforded the title compound (48.8 mg, 42%) as a pale yellow solid. $\delta_H$ (DMSO-$d_6$) 8.26-8.19 (1H, m), 7.84-7.63 (2H, m), 7.26-7.18 (1H, m), 6.95-6.29 (2H, m), 5.82-5.64 (1H, m), 5.63-5.55 & 5.46-5.43 (1H, 2×m), 4.21-3.86 (5H, m), 2.35-2.16 (2H, m), 2.09 (3H, d, J=13.73 Hz), 1.57-1.43 (3H, m). LCMS (ES+) 388 (M+H)+, 3.20 minutes (Method 8).

Example 61

N²-[(S)-1-{8-Chloro-2-[(S)-3-fluoropyrrolidin-1-yl]quinolin-3-yl}ethyl]-6-methyl-[1,3,5]triazine-2,4-diamine Similarly, Intermediate 71 (83 mg, 0.28 mmol), 2-amino-4-chloro-6-methyl-[1,3,5]triazine (45 mg, 0.31 mmol) and DIPEA (0.15 mL, 0.85 mmol) in n-butanol (2.0 mL) afforded the title compound (53 mg, 52%) as a pale yellow solid. $\delta_H$ (DMSO-$d_6$) 8.12 & 8.09 (1H, 2×s), 7.93 & 7.82 (1H, 2×d, J=7.45 Hz), 7.73-7.67 (2H, m), 7.23 (1H, t, J=7.76 Hz), 5.71-5.58 (1H, m), 5.47 (1H, s), 4.24 (1H, dd, J 13.33, 3.21 Hz), 4.17-4.00 (2H, m), 3.96-3.75 (2H, m), 2.40-2.25 (2H, m), 2.17 & 2.07 (3H, 2×s), 1.33 (3H, d, J=6.78 Hz), 1H under solvent. LCMS (ES+) 402 (M+H)+, 2.50 minutes (Method 2).

Example 62

(S)-Ethyl 2-(4-{3-[1-(4-amino-[1,3,5]triazin-2-ylamino)ethyl]-8-chloroquinolin-2-yl}piperazin-1-yl)acetate A solution of Intermediate 57 (120 mg, 0.243 mmol), 2-amino-4-chloro-[1,3,5]triazine (38 mg, 0.292 mmol) and DIPEA (0.17 mL, 0.97 mmol) in n-butanol (3 mL) was heated at 130° C. under microwave irradiation for 1 h. The solvent was removed in vacuo and the residue purified by preparative HPLC to afford the title compound (34 mg, 30%) as a white solid. $\delta_H$ (CDCl₃) 8.13 (1H, s), 7.96 (1H, s), 7.68 (1H, dd, J 7.51, 1.34 Hz), 7.57 (1H, dd, J 8.08, 1.34 Hz), 7.26 (1H, m), 5.73-5.75 (1H, m), 5.53-5.37 (2H, m), 5.09-4.93 (1H, m), 4.22 (2H, q, J=7.13 Hz), 3.81-3.72 (3H, m), 3.44-3.28 (5H, m), 3.00-2.73 (5H, m), 1.30 (3H, t, J 7.13 Hz). LCMS (ES+) 471 (M+H)+, 7.27 minutes (Method 8).

Example 63

(S)-4-{3-[1-(4-Amino-[1,3,5]triazin-2-ylamino)ethyl]-8-chloroquinolin-2-yl}-N,N-dimethylpiperazine-1-carboxamide Following the procedure described for Example 29, Intermediate 72 (60 mg, 0.139 mmol), 2-amino-4-chloro-[1,3,5]triazine (21.8 mg, 0.169 mmol) and DIPEA (0.150 mL, 0.834 mmol) in NMP (2.0 mL) gave the title compound (12 mg, 19%) as an off-white solid. $\delta_H$ (DMSO-$d_6$) 8.29 (1H, d, J=12.49 Hz), 8.03 (1H, d, J=6.29 Hz), 7.96 (1H, d, J=7.81 Hz), 7.82 (2H, d, J 7.76 Hz), 7.42 (1H, t, J 7.81 Hz), 6.77 (2H, d, J=75.58 Hz), 5.50-5.36 (1H, m), 3.68-3.64 (2H, m), 3.49-3.45 (2H, m), 3.15-3.11 (2H, m), 2.83 (6H, s), 1.43 (3H, d, J=6.62 Hz), 2H under H₂O. LCMS (ES+) 456 (M+H)+, 2.57 minutes (Method 2).

Example 64

(S)-1-(4-{3-[1-(4-Amino-6-methyl-[1,3,5]triazin-2-ylamino)ethyl]-8-chloroquinolin-2-yl}-[1,4]diazepan-1-yl)ethanone Following the procedure described for Example 30, Intermediate 73 (93 mg, 0.27 mmol), 2-amino-4-chloro-6-methyl-[1,3,5]triazine (46 mg, 0.32 mmol) and DIPEA (0.10 mL, 0.45 mmol) in n-butanol (3.0 mL) afforded the title compound (109 mg, 89%) as an off-white solid. $\delta_H$ (DMSO-$d_6$) 8.29 (1H, d, J=12.49 Hz), 8.03 (1H, d, J=6.29 Hz), 7.96 (1H, d, J=7.81 Hz), 7.82 (2H, d, J=7.76 Hz), 7.42 (1H, t, J=7.81 Hz), 6.77 (2H, d, J=75.97 Hz), 5.50-5.36 (1H, m), 3.66 (3H, s), 3.47 (3H, s), 3.13 (3H, s), 2.83 (5H, s), 1.43 (3H, d, J=6.62 Hz), 1H under H₂O. LCMS (ES+) 455 (M+H)+, 2.30 minutes (Method 2).

Example 65

(S)-4-(7-Fluoro-8-methyl-3-{1-[4-(methylamino)-[1,3,5]triazin-2-ylamino]ethyl}-quinolin-2-yl)piperazin-2-one TFA (1 mL) was added to a stirred solution of Intermediate 29 (1.50 g, 3.73 mmol) in DCM and the mixture was allowed to stand at r.t. for 16 h before being concentrated in vacuo. The residue was dissolved in MeOH (10 mL) and purified by SCX column chromatography, eluting with MeOH and then 1M NH₃ in MeOH, to afford a clear oil (1.10 g, 97%). To a solution of this oil (80 mg, 0.26 mmol) in n-butanol (2.2 mL) were added 4-chloro-N-methyl-[1,3,5]triazin-2-amine (50 mg, 0.34 mmol) and DIPEA (0.13 mL, 0.78 mmol). The reaction mixture was heated at 140° C. for 20 h. The solvent was removed in vacuo, and the residue was dissolved in DCM (20 mL) and washed with water (2×5 mL). The organic layer was separated, dried (MgSO₄), filtered and concentrated in vacuo. The residue was purified by preparative HPLC, followed by column chromatography (SiO₂, 5% MeOH in DCM), to give the title compound (15 mg, 14%) as an off-white solid. $\delta_H$ (DMSO-$d_6$) 8.33-8.23 (1H, m), 8.13-7.88 (3H, m), 7.80-7.67 (1H, m), 7.36-7.17 (2H, m), 5.47-5.39 & 5.33-5.22 (1H, 2×m), 4.47 & 4.33 (1H, 2×d, J=17.13 Hz), 4.18-3.96 (1H, m), 3.91-3.72 (1H, m), 3.74-3.09 (1H, m), 2.78 (2H, dd, J 14.48, 4.83 Hz), 2.65 (3H, d, J=4.73 Hz), 1.50 (3H, d, J=6.66 Hz), 1.50 & 1.41 (3H, 2×d, J=6.66 Hz). LCMS (ES+) 411 (M+H)+, 2.24 minutes (Method 2).

Example 66

(S)-N²-{1-[7-Fluoro-8-methyl-2-(pyrrolidin-1-yl)quinolin-3-yl]ethyl}-6-methyl-[1,3,5]triazine-2,4-diamine Intermediate 74 (270 mg, 0.73 mmol) was dissolved in 1,4-dioxane (10 mL) and HCl (4M in 1,4-dioxane, 4 mL) was added. The reaction mixture was stirred at r.t. for 2 h then basified with 15% NaOH solution and extracted with DCM (50 mL). The organic layer was separated, dried (MgSO₄), filtered and concentrated in vacuo to afford a yellow oil (200 mg, 73%). This material (70 mg, 0.25 mmol), 2-amino-4- chloro-6-methyl-[1,3,5]triazine (40 mg, 0.27 mmol) and DIPEA (100 mg, 0.78 mmol) in n-butanol (2.0 mL) were stirred at 110° C. for 18 h. The solvent was removed in vacuo and the residue purified by preparative HPLC to afford the title compound (20 mg, 21%) as a cream solid. $\delta_H$ (DMSO-$d_6$) 7.84 (1H, s), 7.39 (1H, dd, J 8.80, 6.24 Hz), 6.96 (1H, t, J 9.02 Hz), 5.70-5.50 (1H, m), 5.52-5.42 (1H, m), 4.99 (2H, s), 3.87-3.77 (2H, m), 3.75-3.67 (3H, m), 2.54 (3H, d, J=2.38 Hz), 2.28 (2H, br s), 2.08-1.91 (4H, m), 1.46 (3H, d, J=6.67 Hz). LCMS (ES+) 382 (M+H)$^+$, 2.19 minutes (Method 2).

Example 67

(S)-2-[4-(8-Chloro-3-{1-[4-(methylamino)-[1,3,5] triazin-2-ylamino]ethyl}quinolin-2-yl)piperazin-1-yl]ethanol Intermediate 75 (40 mg, 0.10 mmol), n-butanol (6 mL), DIPEA (1 mL) and 4-chloro-N-methyl-[1,3,5]triazin-2-amine (50 mg, 0.35 mmol) were combined in a sealed tube and heated under microwave irradiation to 140° C. for 1 h. The reaction mixture was then concentrated to dryness and purified by preparative HPLC to give the title compound (4.5 mg, 10%) as an off-white solid. $\delta_H$ (DMSO-$d_6$) 8.35-7.90 (2H, m), 7.80 (2H, d, J=7.65 Hz), 7.39 (2H, t, J=7.81 Hz), 7.30-7.20 (1H, m), 5.55-5.25 (1H, m), 4.45 (1H, m), 3.80-3.55 (3H, m), 3.40-2.40 (12H, m), 1.55-1.35 (3H, LCMS (ES+) 443 (M+H)$^+$, 3.07 minutes (Method 1).

Example 68

(S)-2-(4-{3-[1-(4-Amino-[1,3,5]triazin-2-ylamino) ethyl]-8-chloroquinolin-2-yl}piperazin-1-yl)ethanol Intermediate 75 (65 mg, 0.17 mmol), n-butanol (5 mL), DIPEA (1 mL) and 2-amino-4-chloro-[1,3,5]triazine (30 mg, 0.23 mmol) were combined in a sealed tube and heated under microwave irradiation to 140° C. for 1 h. The reaction mixture was then concentrated and purified by preparative HPLC to give the title compound (33.4 mg, 48%) as an off-white solid. $\delta_H$ (DMSO-$d_6$) 8.27-8.20 (1H, m), 8.02 (1H, s), 7.96-7.79 (2H, m), 7.39 (1H, t, J 7.80 Hz), 7.00-6.40 (3H, br m), 5.43-5.35 (1H, m), 4.50-4.40 (1H, m), 3.75-3.52 (4H, m), 3.18-3.11 (2H, m), 2.78-2.51 (4H, m), 1.41 (3H, d, J=6.54 Hz), 2H under H$_2$O peak. LCMS (ES+) 429 (M+H)$^+$, 6.95 minutes (Method 8).

Example 69

(S)-2-(4-{3-[1-(4-Amino-6-methyl-[1,3,5]triazin-2-ylamino)ethyl]-8-chloroquinolin-2-yl}piperazin-1-yl)ethanol Intermediate 75 (65 mg, 0.17 mmol), n-butanol (5 mL), DIPEA (1 mL) and 2-amino-4-chloro-6-methyl-[1,3,5]triazine (23 mg, 0.17 mmol) were combined in a sealed tube and heated under microwave irradiation to 140° C. for 1 h. The reaction mixture was concentrated and purified by preparative HPLC to give the title compound (35.8 mg, 48%) as an off-white solid. $\delta_H$ (DMSO-$d_6$) 8.26 (1H, d, J=13.47 Hz), 7.89-7.73 (3H, m), 7.39 (1H, t, J 7.78 Hz), 6.52 (2H, d, J 103.10 Hz), 5.45 (1H, d, J=45.97 Hz), 4.45 (1H, s), 3.75 (2H, d, J 47.55 Hz), 3.59 (2H, d, J=6.08 Hz), 3.14 (3H, s), 2.82-2.70 (3H, m), 2.65 (3H, s), 2.15-2.09 (2H, m), 1.39 (3H, d, J=6.56 Hz). LCMS (ES+) 443 (M+H)$^+$, 6.89 minutes (Method 8).

Example 70

(S)-1-(4-{3-[1-(4-Amino-[1,3,5]triazin-2-ylamino) ethyl]-7-fluoro-8-methylquinolin-2-yl}piperazin-1-yl)-2-hydroxyethanone Intermediate 76 (43 mg, 0.09 mmol), MeOH (5 mL) and HCl (2N in Et$_2$O, 2 mL) were combined and stirred at r.t. for 5 h. The reaction mixture was then concentrated to dryness. The resulting material (40 mg), n-butanol (6 mL), DIPEA (1 mL) and 2-amino-4-chloro-[1,3,5]triazine (45 mg, 0.35 mmol) were combined and heated under microwave irradiation to 150° C. for 40 minutes. The reaction mixture was then concentrated and purified by preparative HPLC to give the title compound (8.19 mg, 21%) as an off-white solid. $\delta_H$ (DMSO-$d_6$) 8.26 (1H, d, J=7.72 Hz), 8.04-7.93 (1H, m), 7.77-7.71 (1H, m), 7.33 (1H, t, J=9.11 Hz), 5.48-5.41 (1H, m), 4.68-4.60 (1H, m), 4.22-4.17 (2H, m), 3.88-3.46 (7H, m), 3.18-2.97 (3H, m), 1.42 (3H, d, J=6.58 Hz), 3 NH and OH not visible. LCMS (ES+) 441 (M+H)$^+$, 9.92 minutes (Method 9).

Example 71

(S)-Ethyl 2-[4-(8-chloro-3-{1-[4-(methylamino)-[1, 3,5]triazin-2-ylamino]ethyl}quinolin-2-yl)piperazin-1-yl]acetate Intermediate 57 (60 mg, 0.16 mmol), n-butanol (6 mL), DIPEA (1 mL) and 4-chloro-N-methyl-[1,3,5]triazin-2-amine (50 mg, 0.35 mmol) were combined in a sealed tube and heated under microwave irradiation to 140° C. for 1 h. The reaction mixture was concentrated and purified by preparative HPLC to give the title compound (12.4 mg, 16%) as an off-white solid. $\delta_H$ (DMSO-$d_6$) 8.28 (1H, t, J=18.54 Hz), 8.13-7.92 (2H, m), 7.81 (2H, d, J=7.65 Hz), 7.40 (1H, t, J=7.79 Hz), 7.28 (1H, d, J=5.11 Hz), 5.53-5.32 (1H, m), 4.16 (2H, q, J=7.11 Hz), 3.66 (2H, d, J=31.57 Hz), 3.29-3.10 (3H, m), 2.93-2.63 (8H, m), 1.56-1.38 (3H, m), 1.25 (3H, t, J=7.16 Hz). LCMS (ES+) 485 (M+H)$^+$, 3.13 minutes (Method 1).

Example 72

(S)-2-(4-{3-[1-(4-Amino-6-methyl-[1,3,5]triazin-2-ylamino)ethyl]-8-chloroquinolin-2-yl}piperazin-1-yl)acetic acid Intermediate 56 (500 mg, 1.05 mmol), EtOH (5 mL) and HCl (2N in Et$_2$O, 5 mL) were combined and stirred at r.t. for 4 days. The reaction mixture was then concentrated to give a yellow glass (526 mg, quantitative). A portion of this glass (60 mg, 0.14 mmol), n-butanol (6 mL), DIPEA (1 mL) and 2-amino-4-chloro-6-methyl-[1,3,5]triazine (19.3 mg, 0.41 mmol) were combined in a sealed tube and heated under microwave irradiation to 140° C. for 1 h. NaOH solution (15%; 0.25 ml) was then added to the reaction mixture, which was heated under microwave irradiation at 140° C. for 1 h. The reaction mixture was then concentrated and purified by preparative HPLC to give the title compound (29.3 mg, 46%) as an off-white solid. $\delta_H$ (DMSO-$d_6$) 8.35-8.24 (1H, m), 7.90-7.71 (3H, m), 7.43-7.36 (1H, m), 6.90-6.35 (2H, m), 5.55-5.35 (1H, m), 3.90-3.65 (3H, m), 3.20 (3H, s), 3.00-2.80 (5H, m), 2.14-2.10 (2H, m), 1.42-1.35 (3H, m). LCMS (ES+) 457 (M+H)$^+$, 7.69 minutes (Method 9).

Example 73

(S)-2-[4-(8-Chloro-3-{1-[4-(methylamino)-[1,3,5]triazin-2-ylamino]ethyl}quinolin-2-yl)piperazin-1-yl]acetic acid Following the procedure described for Example 72, a portion of the yellow glass (60 mg, 0.14 mmol), n-butanol (6 mL), DIPEA (1 mL) and 4-chloro-N-methyl-[1,3,5]triazin-2-amine (50 mg, 0.35 mmol) were combined in a sealed tube and heated under microwave irradiation to 140° C. for 1 h. NaOH solution (15%; 0.4 mL) was then added to the reaction mixture, which was stirred at r.t. for 2 days. The reaction mixture was concentrated and purified by preparative HPLC to give the title compound (11 mg, 17%) as a white solid. $\delta_H$ (DMSO-d$_6$) 8.33-8.20 (1H, m), 8.14-7.90 (2H, m), 7.80 (2H, d, J=7.68 Hz), 7.39 (1H, t, J=7.81 Hz), 7.29-7.24 (1H, m), 5.49-5.42 (1H, m), 3.78-3.54 (3H, m), 3.19 (4H, d, J=13.91 Hz), 2.87-2.63 (6H, m), 1.49 & 1.42 (3H, 2×d, J=6.61 Hz), 1H under solvent. LCMS (ES+) 457 (M+H)$^+$, 2.12 minutes (Method 1).

Example 74

N-{[(R)-1-{3-[(S)-1-(4-Amino-6-methyl-[1,3,5]triazin-2-ylamino)ethyl]-8-chloro-quinolin-2-yl}pyrrolidin-3-yl]methyl}acetamide Intermediate 77 (240 mg, 0.54 mmol), MeOH (5 mL) and HCl (2N in Et$_2$O, 5 mL) were combined and stirred at r.t. for 21 h. The reaction mixture was then concentrated to give a yellow solid (250 mg). A portion of this solid (50 mg, 0.13 mmol), n-butanol (6 mL), DIPEA (1 mL) and 2-amino-4-chloro-6-methyl-[1,3,5]triazine (40 mg, 0.28 mmol) were combined in a sealed tube and heated under microwave irradiation to 160° C. for 2 h. The reaction mixture was concentrated and purified by preparative HPLC to give the title compound (35.2 mg, 60%) as a clear glass. $\delta_H$ (DMSO-d$_6$) 8.14-8.04 (2H, m), 7.85-7.62 (3H, m), 7.19 (1H, t, J=7.75 Hz), 6.64 (2H, br s), 5.80-5.60 (1H, m), 4.12 (1H, br s), 3.98-3.81 (2H, m), 3.80-3.70 (1H, m), 3.60-3.45 (1H, m), 3.20-3.10 (1H, m), 2.61-2.47 (1H, m), 2.16-2.00 (4H, m), 1.86 (3H, s), 1.41-1.36 (3H, m). LCMS (ES+) 455 (M+H)$^+$, 2.64 minutes (Method 1).

Example 75

(S)-1-{3-[1-(4-Amino-6-methyl-[1,3,5]triazin-2-ylamino)ethyl]-7-fluoro-8-methyl-quinolin-2-yl}piperidine-4-carboxamide Intermediate 78 (800 mg, 1.86 mmol), MeOH (10 mL) and HCl (2N in Et$_2$O, 7 mL) were combined and stirred at r.t. for 19 h. The reaction mixture was concentrated to give a yellow solid (680 mg, quantitative). A portion of this solid (50 mg, 0.14 mmol), n-butanol (6 mL), DIPEA (1 mL) and 2-amino-4-chloro-6-methyl-[1,3,5]triazine (40 mg, 0.35 mmol) were combined in a sealed tube and heated under microwave irradiation to 160° C. for 2 h. The reaction mixture was concentrated and purified by preparative HPLC to give the title compound (19.9 mg) as a clear glass. $\delta_H$ (DMSO-d$_6$) 8.20 (1H, s), 7.79 (1H, d, J=7.96 Hz), 7.68 (1H, t, J=7.78 Hz), 7.38-7.21 (2H, m), 6.83 (1H, d, J=14.36 Hz), 6.70-6.36 (2H, m), 5.52-5.38 (1H, m), 4.37 (0.5H, d, J=12.06 Hz), 4.12 (0.5H, d, J=12.56 Hz), 3.70-3.58 (1H, m), 3.23-3.11 (1H, m), 2.66 (1H, dd, J 23.39, 12.03 Hz), 2.36 (1H, t, J=10.34 Hz), 2.12 (2H, s), 1.91 (5H, s), 1.45-1.33 (3H, m). LCMS (ES+) 439 (M+H)$^+$, 2.74 minutes (Method 1).

Example 76

(S)-1-{3-[1-(4-Amino-[1,3,5]triazin-2-ylamino)ethyl]-7-fluoro-8-methylquinolin-2-yl}piperidine-4-carboxamide Following the procedure described for Example 75, a portion of the yellow solid (50 mg, 0.14 mmol), n-butanol (6 mL), DIPEA (1 mL) and 2-amino-4-chloro-[1,3,5]-triazine (30 mg, 0.23 mmol) were combined in a sealed tube and heated under microwave irradiation to 160° C. for 2 h. The reaction mixture was concentrated and purified by preparative HPLC to give the title compound (16.8 mg, 28%) as a clear glass. $\delta_H$ (DMSO-d$_6$) 8.09 (1H, s), 7.88 (1H, d, J=7.14 Hz), 7.74 (1H, d, J=8.01 Hz), 7.63-7.54 (1H, m), 7.25-7.10 (2H, m), 6.71 (1H, d, J=14.43 Hz), 5.31 (1H, d, J=8.65 Hz), 3.98 (1H, d, J=12.52 Hz), 3.50 (1H, d, J=12.07 Hz), 3.08 (1H, s), 3.00 (1H, d, J=12.63 Hz), 2.56 (1H, d, J=22.10 Hz), 2.24 (1H, s), 1.87-1.61 (4H, m), 1.31 (3H, t, J=8.10 Hz), 3H under solvent peak. LCMS (ES+) 425 (M+H)$^+$, 2.32 minutes (Method 2).

Example 77

(S)-N$^2$-(1-{7-Fluoro-8-methyl-2-[4-(2,2,2-trifluoroethyl)piperazin-1-yl]quinolin-3-yl}ethyl)-6-methyl-[1,3,5]triazine-2,4-diamine To a solution of Intermediate 80 (76 mg, 0.187 mmol) in NMP (1.5 mL) were added DIPEA (0.160 mL) and 2-amino-4-chloro-6-methyl-[1,3,5]triazine (27 mg, 0.187 mmol) and the resulting solution was heated under microwave irradiation at 140° C. for 1.5 h. DMSO (1.5 mL) was added and the mixture was purified by preparative HPLC to afford the title compound (33 mg, 37%) as an off-white solid. $\delta_H$ (DMSO-d$_6$) 8.27-8.19 (1H, m), 7.84 (1H, d, J=7.89 Hz), 7.71 (1H, t, J=7.46 Hz), 7.30 (1H, t, J=9.12 Hz), 5.38 (1H, t, J=7.18 Hz), 3.79 (1H, s), 3.67 (1H, s), 3.12 (3H, s), 2.99-2.95 (2H, m), 2.86 (3H, d, J=8.94 Hz), 2.59-2.54 (4H, m), 2.13-2.05 (3H, m), 1.43-1.35 (3H, m), 1H under solvent peak. LCMS (ES+) 479 (M+H)$^+$, 8.69 minutes (Method 8).

Example 78

N$^2$-[(S)-1-{2-[(3S,5R)-3,5-Dimethylpiperazin-1-yl]-7-fluoro-8-methylquinolin-3-yl}ethyl]-6-methyl-[1,3,5]triazine-2,4-diamine To a solution of Intermediate 82 (100 mg, 0.28 mmol) in NMP (1.5 mL) were added DIPEA (0.246 mL) and 2-amino-4-chloro-6-methyl-[1,3,5]triazine (40 mg, 0.28 mmol) and the resulting solution was heated under microwave irradiation at 140° C. for 1.5 h. DMSO (1.5 mL) was added and the mixture was purified by preparative HPLC to afford the title compound (84 mg, 70%) as an off-white solid. $\delta_H$ (DMSO-d$_6$) 8.30 (1H, s), 7.79-7.67 (2H, m), 7.30 (1H, t, J=9.10 Hz), 6.63 (1H, br s), 5.44 (1H, d, J=11.70 Hz), 4.22-4.11 (1H, m), 3.85-3.73 (1H, m) 3.50 (2H, t, J=11.85 Hz), 3.10 (1H, s), 2.82 (1H, s), 2.56 (3H, d, J=2.20 Hz), 2.10 (4H, t, J=9.59 Hz), 1.39 (3H, dd, J 12.90, 6.61 Hz), 1.15 (3H, d, J=6.17 Hz), 1.04 (2H, d, J=6.23 Hz), 0.96 (1H, d, J=6.23 Hz), 1H under solvent. LCMS (ES+) 425 (M+H)$^+$, 7.07 minutes (Method 9).

Example 79

(S)-N$^2$-{1-[7-Fluoro-2-(4-isopropylpiperazin-1-yl)-8-methylquinolin-3-yl]ethyl}-6-methyl-[1,3,5]triazine-2,4-diamine To a solution of Intermediate 83 (100 mg, 0.27 mmol) in NMP (1.5 mL) were added DIPEA (0.240 mL) and 2-amino-4-chloro-6-methyl-[1,3,5]triazine (40 mg, 0.27 mmol) and the resulting solution was heated under microwave irradiation at 140° C. for 1.5 h. DMSO (1.5 mL) was added and the mixture was purified by preparative HPLC to afford the title compound (60 mg, 50%) as an off-white solid. $\delta_H$(CDCl$_3$) 7.92 (1H, s), 7.47 (1H, dd, J 8.88, 6.03 Hz), 7.12 (1H, t, J=8.98 Hz), 5.53 (2H, d, J=72.38 Hz), 4.98 (2H, s), 3.74 (3H, s), 3.27 (3H, s), 2.93-2.73 (6H, m), 2.61-2.57 (3H, m), 2.27 (3H, s), 1.16 (6H, d, J=6.49 Hz). LCMS (ES+) 439 (M+H)$^+$, 7.08 minutes (Method 9).

Example 80

(S)-1-(4-{3-[1-(4-Amino-6-methyl-[1,3,5]triazin-2-ylamino)ethyl]-7-fluoro-8-methylquinolin-2-yl}piperazin-1-yl)-2,2-dimethylpropan-1-one To a solution of Intermediate 84 (100 mg, 0.245 mmol) in NMP (1.5 mL) were added DIPEA (0.230 mL) and 2-amino-4-chloro-6-methyl-[1,3,5]triazine (35 mg, 0.245 mmol) and the resulting solution was heated under microwave irradiation at 140° C. for 1.5 h. DMSO (1.5 mL) was added and the mixture was purified by preparative HPLC to afford the title compound (13 mg, 11%) as an off white solid. $\delta_H$(DMSO-d$_6$) 8.26 (1H, d, J=10.72 Hz), 7.73 (2H, s), 7.32 (1H, t, J=9.09 Hz), 6.67 (2H, d, J=56.37 Hz), 5.56-5.43 (1H, m), 3.93-3.85 (2H, m), 3.77 (3H, d, J=9.80 Hz), 3.63-3.53 (1H, m), 3.09 (2H, t, J=12.97 Hz), 2.56 (3H, m), 2.18-2.03 (3H, m), 1.41 (3H, d, J=6.52 Hz), 1.29 (9H, s). LCMS (ES+) 481 (M+H)$^+$, 10.52 minutes (Method 10).

Example 81

(S)-4-{3-[1-(4-Amino-[1,3,5]triazin-2-ylamino)ethyl]-8-bromoquinolin-2-yl}piperazin-2-one To a solution of Intermediate 95 (35 mg, 0.10 mmol) in dry n-butanol (1.5 mL) were added 2-amino-4-chloro-[1,3,5]triazine (20 mg, 0.15 mmol) and DIPEA (0.09 mL, 0.5 mmol). The reaction mixture was heated at 130° C. under microwave irradiation for 90 minutes. The solvent was removed in vacuo and the residue purified by preparative HPLC to afford the title compound (6 mg, 11%) as an off-white solid. $\delta_H$(MeOD-d$_4$) 8.26 (1H, s), 8.05 (1H, s), 7.96 (1H, d, J=7.53 Hz), 7.79 (1H, d, J=7.91 Hz), 7.32 (1H, t, J=7.8 Hz), 5.60-5.45 (1H, m), 4.50 (1H, d, J=17.6 Hz), 4.39 (1H, d, J=18.4 Hz), 4.15-4.08 (2H, m), 3.60-3.52 (1H, m), 3.48-3.40 (1H, m), 1.49 (3H, d, J=6.87 Hz). LCMS (ES+) 443, 445 (M+H)$^+$, 2.60 minutes (Method 1).

Example 82

(S)-4-{3-[1-(4-Amino-6-methyl-[1,3,5]triazin-2-ylamino)ethyl]-5-fluoro-8-methyl-quinolin-2-yl}piperazin-2-one Following the procedure described for Example 81, Intermediate 96 (70 mg, 0.23 mmol), 2-amino-4-chloro-6-methyl-[1,3,5]triazine (50 mg, 0.35 mmol) and DIPEA (0.21 mL, 1.2 mmol) in dry n-butanol (2.5 mL) afforded the title compound (60 mg, 63%) as an off-white solid. $\delta_H$(MeOD-d$_4$) 8.43 (1H, s), 7.44 (1H, t, J=6.98 Hz), 7.03 (1H, t, J=8.92 Hz), 5.59-5.52 (1H, m), 4.51 (1H, d, J=17.2 Hz), 4.36 (1H, d, J=17.2 Hz), 4.18-3.60 (4H, m), 3.63-3.54 (1H, m), 3.46-3.38 (1H, m), 2.66 (3H, s), 2.25 & 2.17 (3H, 2xs), 1.49 (3H, d, J=6.66 Hz). LCMS (ES+) 411 (M+H)$^+$, 2.17 minutes (Method 2).

Example 83

N-[(R)-1-{3-[(S)-1-(4-Amino-6-methyl-[1,3,5]triazin-2-ylamino)ethyl]-7-fluoro-8-methylquinolin-2-yl}pyrrolidin-3-yl]acetamide Similarly, Intermediate 97 (60 mg, 0.15 mmol), 2-amino-4-chloro-6-methyl-[1,3,5]triazine (32 mg, 0.22 mmol) and DIPEA (0.13 mL, 0.74 mmol) in dry n-butanol (2 mL) afforded the title compound (36 mg, 55%) as a peach solid. $\delta_H$(MeOD-d$_4$) 8.02 (1H, s), 7.52 (1H, dd, J 8.84, 6.23 Hz), 7.02 (1H, t, J=9.10 Hz), 5.80-5.68 (1H, m), 4.55-4.40 (1H, m), 4.19-4.06 (2H, m), 3.88-3.64 (2H, m), 2.55 (3H, d, J=2.33 Hz), 2.34-2.15 (4H, m), 2.15-2.05 (1H, m), 1.96 (3H, s), 1.47 (3H, d, J=6.4 Hz). LCMS (ES+) 439 (M+H)$^+$, 2.78 minutes (Method 2).

Example 84

N-[(R)-1-{3-[(S)-1-(4-Amino-[1,3,5]triazin-2-ylamino)ethyl]-7-fluoro-8-methylquinolin-2-yl}pyrrolidin-3-yl]acetamide Similarly, Intermediate 97 (60 mg, 0.15 mmol), 2-amino-4-chloro-[1,3,5]triazine (29 mg, 0.22 mmol) and DIPEA (0.13 mL, 0.74 mmol) in dry n-butanol (2 mL) afforded the title compound (5 mg, 8%) as an off-white solid. $\delta_H$(MeOD-d$_4$) 8.05 (1H, s), 8.03 (1H, s), 7.54 (1H, d, J=7.4 Hz), 7.03 (1H, t, J=9.08 Hz), 5.74-5.68 (1H, m), 4.52-4.42 (1H, m), 4.20-4.09 (2H, m), 3.90-3.65 (2H, m), 2.56 (3H, d, J=2.32 Hz), 2.33-2.23 (1H, m), 2.15-2.05 (1H, m), 1.97 (3H, s), 1.47 (3H, d, J=6.88 Hz). LCMS (ES+) 425 (M+H)$^+$, 2.16 minutes (Method 2).

Example 85

(S)-N-(1-{3-[1-(4-Amino-6-methyl-[1,3,5]triazin-2-ylamino)ethyl]-8-chloroquinolin-2-yl}piperidin-4-yl)acetamide A solution of Intermediate 93 (140 mg, 0.31 mmol) and HCl (1.6 mL, 6.26 mmol, 4M in 1,4-dioxane) in 1,4-dioxane (7.5 mL) was stirred at r.t. overnight. The solvent was removed in vacuo to give a yellow paste (130 mg). A solution of this paste (60 mg, 0.14 mmol), 2-amino-4-chloro-6-methyl-[1,3,5]triazine (31 mg, 0.21 mmol) and DIPEA (0.13 mL, 0.71 mmol) in n-butanol (2 mL) was heated at 130° C. under microwave irradiation for 90 minutes. The solvent was removed in vacuo and purification by preparative HPLC afforded the title compound (40 mg, 62%) as an off-white solid. $\delta_H$ (MeOD-d$_4$) 8.16 (1H, s), 7.70 (2H, d, J=7.5 Hz), 7.32 (1H, t, J=7.8 Hz), 5.60-5.48 (1H, m), 4.32-4.25 & 4.15-4.05 (1H, m), 3.97-3.86 (1H, s), 3.77-3.64 (1H, m), 2.97-2.80 (1H, m), 2.20 (3H, m), 2.17-1.70 (10H, m), 1.78-1.62 (1H, m), 1.58-1.42 (3H, m). LCMS (ES+) 455, 457 (M+H)$^+$, 2.23 minutes (Method 2).

Example 86

(S)-N-(1-{3-[1-(4-Amino-[1,3,5]triazin-2-ylamino) ethyl]-8-chloroquinolin-2-yl}-piperidin-4-yl)acetamide Following the procedure described for Example 85, Intermediate 93 (140 mg, 0.31 mmol) and HCl (1.6 mL, 6.26 mmol, 4M in 1,4-dioxane) in 1,4-dioxane (7.5 mL), followed by 2-amino-4-chloro-[1,3,5]triazine (28 mg, 0.21 mmol) and DIPEA (0.13 mL, 0.71 mmol) in n-butanol (2 mL), afforded the title compound (36 mg, 57%) as a cream solid. $\delta_H$ (MeOD-$d_4$) 8.17 (1H, s), 8.03 (1H, br s), 7.70 (2H, d, J=7.78 Hz), 7.32 (1H, t, J=7.78 Hz), 5.58-5.48 (1H, m), 4.08 (1H, br d, J=13.05 Hz), 3.96-3.88 (1H, m), 3.68 (1H, d, J=13.00 Hz), 3.40-3.29 (1H, m), 2.95-2.85 (1H, m), 2.08 (3H, s), 2.21-1.83 (2H, m), 1.70 (2H, qd, J 11.73, 4.00 Hz), 1.52 (3H, d, J=6.73 Hz). LCMS (ES+) 441, 443 (M+H)$^+$, 2.33 minutes (Method 2).

Example 87

(S)-N$^2$-{1-[8-chloro-2-([1,4]oxazepan-4-yl)quinolin-3-yl]ethyl}-6-methyl-[1,3,5]triazine-2,4-diamine To a solution of Intermediate 11 (150 mg, 0.44 mmol) were added homo-morpholine hydrochloride (61 mg, 0.36 mmol), n-butanol (5 mL) and DIPEA (0.16 mL, 0.88 mmol). The reaction mixture was heated at 120° C. overnight. Further homo-morpholine hydrochloride (220 mg, 1.32 mmol) and DIPEA (0.48 mL, 2.64 mmol) were added and the reaction mixture was heated under microwave irradiation at 120° C. for 1 h, then at 140° C. for 1 h, then further DIPEA (0.5 mL, 2.75 mmol) was added and the reaction mixture heated at 140° C. for a further 2 h. The solvent was removed in vacuo and the crude residue partitioned between water (30 mL) and EtOAc (100 mL). The organic layer was washed with water (3×30 mL), separated, dried (MgSO$_4$) and filtered, and the solvent was removed in vacuo to give a brown oil (200 mg). To a solution of the brown oil (200 mg) in MeOH (2 mL) was added HCl (2 mL, 2M solution in Et$_2$O). The resulting solution was stirred at r.t. for 3 days. The solvents were removed to yield a crude oil (180 mg). To this oil were added n-butanol (5 mL), DIPEA (0.48 mL, 2.64 mmol) and 6-methyl-[1,3,5] triazine-2,4-diamine (55 mg, 0.44 mmol). The reaction mixture was heated at 120° C. overnight. The solvents were removed in vacuo and the crude residue was partitioned between EtOAc (100 mL) and water (30 mL). The organic layer was separated, washed with water (4×20 mL), dried (MgSO$_4$) and filtered, and the solvent was removed in vacuo. Purification by preparative HPLC afforded the title compound (18 mg, 10%) as a cream solid. $\delta_H$ (DMSO-$d_6$) 8.20 (1H, d, J=8.19 Hz), 7.77-7.72 (2H, m), 7.32 (1H, t, J 7.79 Hz), 5.55-5.38 (1H, m), 3.99-3.79 (8H, m), 2.15-2.02 (3H, m), 1.40 (3H, d, J=6.71 Hz), 2H under solvent peak. LCMS (ES+) 414 (M+H)$^+$, 7.92 minutes (Method 8).

Example 88

(S)-Methyl 4-{3-[1-(4-amino-[1,3,5]triazin-2-ylamino)ethyl]-7-fluoro-8-methylquinolin-2-yl}piperazine-1-carboxylate A solution of Intermediate 27 (501 mg, 1.479 mmol), methyl piperazine-1-carboxylate (981 mg, 6.802 mmol) and DIPEA (1.288 mL, 7.394 mmol) in NMP (3 mL) was heated under microwave irradiation at 130° C. for 4.5 h. After cooling, the mixture was dissolved in a 1:1 mixture of EtOAc and Et$_2$O (250 mL) and washed with saturated brine (3×50 mL). The organic layer was separated, dried (MgSO$_4$), filtered and concentrated in vacuo. Purification by column chromatography (SiO$_2$, 10% EtOAc in DCM) gave a pale yellow oil (400 mg, 60%). LCMS (ES+) 447 (M+H)$^+$. To the oil (400 mg, 0.896 mmol) dissolved in DCM (23 mL) was added TFA (4.1 mL). The reaction mixture was stirred at r.t. for 1.5 h. The excess solvent was removed in vacuo. The oil obtained was basified with 0.2M NaOH (40 mL) and extracted with EtOAc (3×80 mL). The combined organic layers were dried (MgSO$_4$), filtered and concentrated in vacuo. Purification by column chromatography (SiO$_2$, 95:4:1 DCM/MeOH/NH$_3$ solution in MeOH) gave a colourless gum (278 mg, 90%). LCMS (ES+) 347 (M+H)$^+$. The colourless gum (55.6 mg, 0.161 mmol), 2-amino-4-chloro-[1,3,5]triazine (31.4 mg, 0.241 mmol), DIPEA (0.084 mL, 0.482 mmol) and n-BuOH (1 mL) were combined and heated under microwave irradiation at 130° C. for 1 h. Purification by preparative HPLC gave the title compound (14.4 mg, 20%) as a white solid. $\delta_H$ (DMSO-$d_6$) 8.25 (1H, d, J=12.60 Hz), 8.02 (1H, d, J=10.06 Hz), 7.95 (1H, d, J=8.01 Hz), 7.74 (1H, dd, J 8.90, 6.24 Hz), 7.33 (1H, t, J 9.13 Hz), 6.78 (2H, d, J=68.59 Hz), 5.41 (1H, s), 3.83-3.59 (3H, m), 3.62-3.56 (4H, m), 3.10-3.04 (3H, m), 2.56 (4H, m), 1.41 (3H, d, J=6.65 Hz). LCMS (ES+) 441 (M+H)$^+$, 8.52 minutes (Method 8).

Example 89

N$^2$-[(S)-1-{8-chloro-2-[(R)-2-(methoxymethyl)pyrrolidin-1-yl]quinolin-3-yl}ethyl]-6-methyl-[1,3,5]triazine-2,4-diamine Intermediate 98 (47 mg, 0.147 mmol), 2-amino-4-chloro-6-methyl-[1,3,5]triazine (32 mg, 0.222 mmol), DIPEA (0.080 mL, 0.447 mmol) and NMP (1 mL) were combined and heated under microwave irradiation at 150° C. for 1 h. After cooling, the mixture was dissolved in a 1:1 mixture of EtOAc and Et$_2$O (200 mL) and washed with saturated brine (3×30 mL). The organic layer was separated, dried (MgSO$_4$), filtered and concentrated in vacuo. Purification by column chromatography (SiO$_2$, 96:3:1 DCM/MeOH/NH$_3$ in MeOH) gave the title compound (8.9 mg, 14%) as a white solid. $\delta_H$ (CDCl$_3$) 7.93 (1H, s), 7.61 (1H, d, J=7.50 Hz), 7.54-7.46 (1H, m), 7.11 (1H, t, J=7.76 Hz), 5.74-4.85 (4H, m), 4.02-3.67 (3H, m), 3.62-3.35 (4H, m), 2.25-1.54 (8H, m), NH and NH$_2$ not visible. LCMS (ES+) 428 (M+H)$^+$, 3.47 minutes (Method 1).

Example 90

N$^2$-[(S)-1-{8-Chloro-2-[(S)-2-(methoxymethyl)pyrrolidin-1-yl]quinolin-3-yl}ethyl]-[1,3,5]triazine-2,4-diamine Intermediate 99 (53 mg, 0.166 mmol), 2-amino-4-chloro-[1,3,5]triazine (32 mg, 0.246 mmol), DIPEA (0.090 mL, 0.50 mmol) and NMP (1 mL) were combined and heated under microwave irradiation at 150° C. for 1 h. After cooling, the mixture was dissolved in a 1:1 mixture of EtOAc and Et$_2$O (200 mL) and washed with saturated brine (3×30 mL). The organic layer was separated, dried (MgSO$_4$), filtered and concentrated in vacuo. Purification by preparative HPLC followed by column chromatography (SiO$_2$, 96:3:1 DCM/MeOH/NH$_3$ in MeOH) gave the title compound (4.6 mg, 7%) as an off-white solid. $\delta_H$ (CDCl$_3$) 8.18 (1H, s), 7.89 (1H, s), 7.66-7.62 (1H, m), 7.51 (1H, dd, J 8.01, 1.36 Hz), 7.14 (1H, t, J=7.69 Hz), 5.65-5.31 (2H, m), 5.02-4.88 (4H, m), 3.86-3.61 (3H, m), 3.55-3.50 (1H, m), 3.38 (3H, s), 2.29-2.25 (1H, m), 2.10-1.85 (2H, m), 1.41 (3H, d, J=6.66 Hz), NH not visible. LCMS (ES+) 414 (M+H)+, 2.55 minutes (Method 2).

Example 91

$N^2$-[(S)-1-{8-Chloro-2-[(R)-2-(methoxymethyl)pyrrolidin-1-yl]quinolin-3-yl}ethyl]-[1,3,5]triazine-2,4-diamine Following the procedure described for Example 89, Intermediate 98 (47 mg, 0.15 mmol), 2-amino-4-chloro-[1,3,5]triazine (29 mg, 0.22 mmol), DIPEA (0.080 mL, 0.447 mmol) and NMP (1 mL) gave the title compound (11.8 mg, 20%) as a white solid. $\delta_H$ (CDCl$_3$) 8.01 (1H, s), 7.93 (1H, s), 7.62 (1H, d, J 7.44 Hz), 7.49 (1H, d, J=7.91 Hz), 7.15-7.08 (1H, m), 5.78 (1H, d, J=7.11 Hz), 5.46-5.31 (1H, m), 5.03 (2H, d, J=44.61 Hz), 3.97-3.83 (2H, m), 3.70 (1H, s), 3.56-3.41 (2H, m), 3.41 (3H, s), 2.17 (1H, t, J=8.53 Hz), 2.08-1.86 (3H, m), 1.70 (3H, d, J=6.75 Hz). LCMS (ES+) 414 (M+H)+, 2.89 minutes (Method 1).

Example 92

$N^2$-[(S)-1-{8-Chloro-2-[(S)-2-(methoxymethyl)pyrrolidin-1-yl]quinolin-3-yl}ethyl]-6-methyl-[1,3,5]triazine-2,4-diamine Following the procedure described for Example 90, Intermediate 99 (53 mg, 0.166 mmol), 2-amino-4-chloro-6-methyl-[1,3,5]triazine (36 mg, 0.246 mmol), DIPEA (0.090 mL, 0.50 mmol) and NMP (1 mL) gave the title compound (29 mg, 45%) as a brown gum. $\delta_H$ (CDCl$_3$) 7.91 (1H, s), 7.65 (1H, dd, J 7.51, 1.35 Hz), 7.53 (1H, d, J=7.90 Hz), 7.20-7.11 (1H, m), 5.69-5.39 (2H, m), 5.20-5.11 (1H, m), 3.90-3.68 (3H, m), 3.60-3.47 (1H, m), 3.40 (3H, s), 2.38-2.17 (4H, m), 2.10-1.84 (4H, m), 1.41 (3H, d, J=6.49 Hz), one NH not visible. LCMS (ES+) 428 (M+H)+, 7.87 minutes (Method 8).

Example 93

4-{3-[(4-Amino-[1,3,5]triazin-2-ylamino)methyl]-8-chloroquinolin-2-yl}piperazin-2-one Intermediate 103 (90 mg, 0.31 mmol) was dissolved in NMP (1.5 mL) and treated with DIPEA (0.27 mL, 0.15 mmol) followed by 2-amino-4-chloro-[1,3,5]triazine (60 mg, 0.47 mmol). The mixture was heated under microwave irradiation to 140° C. for 50 minutes. The crude reaction mixture was purified by preparative HPLC to give the title compound (60 mg, 50%) as an off-white solid. $\delta_H$ (DMSO-d$_6$) 8.17 (1H, s), 8.09-8.00 (2H, m), 7.92 (1H, s), 7.87 (1H, d, J=8.10 Hz), 7.82 (1H, d, J=7.54 Hz), 7.39 (1H, t, J=7.82 Hz), 6.90 (2H, s), 4.67-4.57 (2H, m), 3.60-3.56 (2H, m), 3.52-3.47 (2H, m), 3.45-3.40 (2H, m). LCMS (ES+) 385 (M+H)+, 8.01 minutes (Method 9).

The invention claimed is:

1. A compound of formula (I) or an N-oxide thereof, or a pharmaceutically acceptable salt or solvate thereof:

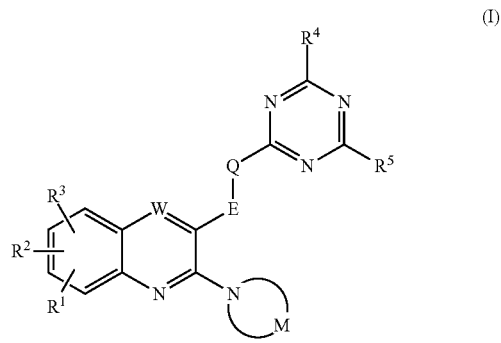

wherein

E represents an optionally substituted straight or branched $C_{1-3}$ alkylene chain;

Q represents oxygen, sulfur, N—$R^6$ or a covalent bond;

the ring comprising M represents an optionally substituted saturated five-, six- or seven-membered monocyclic ring containing one nitrogen atom and 0, 1, 2 or 3 additional heteroatoms independently selected from N, O and S, but containing no more than one O or S atom;

W represents C—$R^7$ or N;

$R^1$, $R^2$ and $R^3$ independently represent hydrogen, halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$alkoxycarbonylamino, $C_{1-6}$alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^4$ and $R^5$ independently represent $C_{1-6}$ alkyl, aryl, aryl ($C_{1-6}$)alkyl, heteroaryl or heteroaryl($C_{1-6}$)alkyl, any of which groups may be optionally substituted by one or more substituents; or hydrogen, halogen, trifluoromethyl, —O$R^a$, —S$R^a$, —SO$R^a$, —SO$_2R^a$, —N$R^bR^c$, —N$R^cCOR^d$, —N$R^cCO_2R^d$, —N$R^cSO_2R^e$, —CO$R^d$, —CO$_2R^d$, —CONR$^bR^c$ or —SO$_2$NR$^bR^c$;

$R^6$ represents hydrogen or $C_{1-6}$ alkyl;

$R^7$ represents hydrogen, halogen, $C_{1-6}$ alkyl or $C_{1-6}$ alkoxy;

$R^a$ represents $C_{1-6}$ alkyl, difluoromethyl or trifluoromethyl;

$R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl ($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$) alkyl, any of which groups may be optionally substituted by one or more substituents;

$R^c$ represents hydrogen, $C_{1-6}$ alkyl or $C_{3-7}$ cycloalkyl;

$R^d$ represents hydrogen or $C_{1-6}$ alkyl; and $R^e$ represents $C_{1-6}$ alkyl.

2. A compound as claimed in claim 1 represented by formula (IIA) or an N-oxide thereof, or a pharmaceutically acceptable salt or solvate thereof:

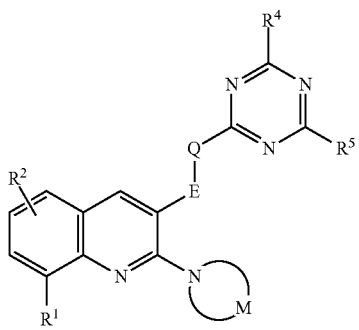

wherein E, Q, M, R¹, R², R⁴ and R⁵ are as defined in claim 1.

3. A compound as claimed in claim 1 wherein the ring comprising M represents a monocyclic ring selected from pyrrolidin-1-yl, imidazolidin-1-yl, piperidin-1-yl, morpholin-4-yl, [1,4]oxazepan-4-yl, thiomorpholin-4-yl, piperazin-1-yl and [1,4]diazepan-1-yl, any of which rings may be optionally substituted by one or more substituents independently selected from halogen, $C_{1-6}$ alkyl, $C_{1-6}$ alkoxy($C_{1-6}$)alkyl, $C_{1-6}$ alkylsulphonyl, hydroxy, hydroxy($C_{1-6}$)alkyl, trifluoroethyl, oxo, $C_{2-6}$ alkylcarbonyl, hydroxy($C_{2-6}$)alkylcarbonyl, ($C_{3-7}$)cycloalkylcarbonyl, carboxy($C_{1-6}$)alkyl, $C_{2-6}$ alkoxycarbonyl, $C_{2-6}$alkoxycarbonyl($C_{1-6}$)alkyl, $C_{2-6}$alkylcarbonylamino, ($C_{2-6}$)alkylcarbonylamino($C_{1-6}$)alkyl, $C_{1-6}$ alkylsulphonylamino, aminocarbonyl, di($C_{1-6}$)alkylaminocarbonyl, di($C_{1-6}$)alkylaminocarbonyl($C_{1-6}$)alkyl and ($C_{3-7}$)heterocycloalkylcarbonyl($C_{1-6}$)alkyl.

4. A compound as claimed in claim 1 wherein R⁵ represents —NR$^b$R$^c$, in which R$^b$ and R$^c$ are as defined in claim 1.

5. A compound as claimed in claim 2 represented by formula (IIB) or an N-oxide thereof, or a pharmaceutically acceptable salt or solvate thereof:

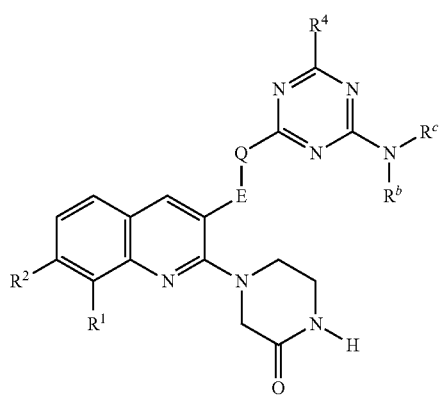

6. A compound as claimed in claim 1 wherein E represents methylene or (methyl)methylene.

7. A compound as claimed in claim 1 wherein Q represents oxygen or N—R⁶, in which R⁶ is as defined in claim 1.

8. A compound as claimed in claim 1 wherein R¹ represents hydrogen, halogen or $C_{1-6}$ alkyl.

9. A compound as claimed in claim 1 wherein R² represents hydrogen or halogen.

10. A compound as claimed in claim 1 wherein R⁴ represents hydrogen or $C_{1-6}$ alkyl.

11. A compound selected from the group consisting of
6-Methyl-N-{(S)-1-[8-methyl-2-(morpholin-4-yl)quinolin-3-yl]ethyl}1-[1,3,5]triazine-2,4-diamine,
6-Methyl-N-{(S)-1-[8-methyl-2-(pyrrolidin-1-yl)quinolin-3-yl]ethyl}1-[1,3,5]triazine-2,4-diamine,
4-{3-[(S)-1-(4-Amino-6-methyl-[1,3,5]triazin-2-ylamino)ethyl]-8-methylquinolin-2-yl}-piperazin-2-one,
N²-[(S)-1-{8-Chloro-2-[(S)-3-methylmorpholin-4-yl]quinolin-3-yl}ethyl]-[1,3,5]triazine-2,4-diamine,
N²-[(S)-1-{8-Chloro-2-[(S)-3-methylmorpholin-4-yl]quinolin-3-yl}ethyl]-6-methyl-[1,3,5]triazine-2,4-diamine,
N-[(S)-1-{3-[(S)-1-(4-Amino-6-methyl-[1,3,5]triazin-2-ylamino)ethyl]-8-methylquinolin-2-yl}pyrrolidin-3-yl]acetamide,
(S)-6-Methyl-N²-{1[-8-methyl-2-(thiomorpholin-4-yl)quinolin-3-yl]ethyl}-[1,3,5]triazine-2,4-diamine,
(S)-6-Methyl-N²-{1-1-[8-chloro-2-(1,1-dioxothiomorpholin-4-yl)quinolin-3-yl]ethyl}-[1,3,5]triazine-2,4-diamine,
(S)-N-(1-{3-[1-(4-Amino-6-methyl-[1,3,5]triazin-2-ylamino)ethyl]-8-chloroquinolin-2-yl}piperidin-4-yl)methanesulfonamide,
(S)-N-(1-{3-[1-(4Amino-[1,3,5]triazin-2-ylamino)ethyl]-8-chloroquinolin-2-yl}-piperidin-4-yl)methanesulfonamide,
(S)-1(4-{3-[1-(4-Amino-[1,3,5]triazin-2-ylamino)ethyl]-8-chloroquinolin-2-yl}piperazin-1-yl)ethanone,
(S)-1-(4-{3-[1-(4-Amino-6-methyl-[1,3,5]triazin-2-ylamino)ethyl]-8-chloroquinolin-2-yl}piperazin-1-yl)ethanone,
(S)-4-{3-[1-(4-Amino-[1,3,5]triazin-2-ylamino)ethyl]-8-methylquinolin-2-yl}piperazin-2-one,
(S)-4-{3-[1-(4-Amino[1,3,5]triazin-2-ylamino)ethyl]-8-chloroquinolin-2-yl}piperazin-2-one,
(S)-4-{3-[1-(4-Amino-6-methyl-[1,3,5]triazin-2-ylamino)ethyl]-8-chloroquinolin-2-yl}piperazin-2-one,
(S)-4-{3-[1-(4-Amino-[1,3,5]triazin-2-ylamino)ethyl]-7-fluoro-8-methylquinolin-2-yl}piperazin-2-one,
(S)-4-{3-[1-(4-Amino-6-methyl-[1,3,5]triazin-2-ylamino)ethyl]-7-fluoro-8-methyl-quinolin-2-yl}piperazin-2-one,
N-{(1S)-1-[8-Chloro-2-(pyrrolidin-1-yl)quinolin-3-yl]ethyl}-[1,3,5]triazine-2,4-diamine,
N-{(1S)-1-[8-Chloro-2-(morpholin-4-yl)quinolin-3-yl]ethyl}-6-methyl-[1,3,5]triazine-2,4-diamine,
(3R)-1-(3-{(1S)-1-[(4-Amino-[1,3,5 ]triazin-2-yl)amino]ethyl}-8-chloroquinolin-2-yl)pyrrolidin-3-ol,
(3R)-1-(3-{(1S)-1-[(4-Amino-6-methyl-[1,3,5]triazin-2-yl)amino]ethyl}-8-chloro-quinolin-2-yl)pyrrolidin-3-ol,
(3S)-1-(3-{(1S)-1-[(4-Amino-[1,3,5]triazin-2-yl)amino]ethyl}-8-chloroquinolin-2-yl)pyrrolidin-3-ol,
(3S)-1-(3-{(1S)-1-[(4-Amino-6-methyl-[1,3,5]triazin-2-yl)amino]ethyl}-8-chloroquinolin-2-yl)pyrrolidin-3-ol,
1-(3-{(1S)-1-1-[(4-Amino-[1,3,5]triazin-2-yl)amino]ethyl}-8-chloroquinolin-2-yl)-[1,4]-diazepan-5-one,
1-(3-{(1S)-1-[(4-Amino-6-methyl-[1,3,5]triazin-2-yl)amino]ethyl}-8-chloroquinolin-2-yl)-[1,4]diazepan-5-one,
4-(3-{(1S)-1-[(4-Amino-[1,3,5]triazin-2-yl)amino]ethyl}-8-chloroquinolin-2-yl)-1-methylpiperazin-2-one,
4-(3-{(1S)-1-[(4-Amino-6-methyl-[1,3,5]triazin-2-yl)amino]ethyl}-8-chloroquinolin-2-yl)-1-methylpiperazin-2-one, 1-(3-{(1S)-1-[(4-Amino-[1,3,5]triazin-2-yl)amino]
 ethyl}-8-chloroquinolin-2-yl)-imidazolidin-2-one,
(S)-(4-{3-[1-(4-Amino-[1,3,5]triazin-2-ylamino)ethyl]-8-
 methylquinolin-2-yl}piperazin-1-yl)(cyclopropyl)
 methanone,
(S)-4-(8-Chloro-3-{1-[4-(methylamino)-[1,3,5]triazin-2-
 ylamino]ethyl}quinolin-2-yl)piperazin-2-one,
1-(3-{(1S)-1-[(4-Amino-6-methyl-[1,3,5]triazin-2-yl)
 amino]ethyl}-8-methylquinolin-2-yl)-[1,4]diazepan-5-
 one,
1-(3-{(1S)-1-[(4-Amino-[1,3,5]triazin-2-yl)amino]
 ethyl}-8-methylquinolin-2-yl)-[1,4]-diazepan-5-one,
6-Methyl-N-{(1S)-1-[8-methyl-2-(piperazin-1-yl)quino-
 lin-3-yl]ethyl}-[1,3,5]triazine-2,4-diamine,
(S)-(4-{3-[1-(4-Amino-6-methyl-[1,3,5]triazin-2-
 ylamino)ethyl]-8-chloroquinolin-2-yl}piperazin-1-yl)
 (cyclopropyl)methanone,
(S)-(4-{3-[1-(4-Amino-[1,3,5]triazin-2-ylamino)ethyl]-8-
 chloroquinolin-2-yl}piperazin-1-yl)(cyclopropyl)
 methanone,
(S)-2-(4-{3-[1-(4-Amino-6-methyl-[1,3,5]triazin-2-
 ylamino)ethyl]-8-methylquinolin-2-yl}piperazin-1-yl)-
 N,N-dimethylacetamide,
(S)-2(4-{3-[1-(4Amino-6-methyl-[1,3,5]triazin-2-
 ylamino)ethyl]-8-methylquinolin-2-yl}piperazin-1-yl)-
 1-(morpholin-4-yl)ethanone,
(S)-N²-(1-{8-Chloro-2-[4-(methylsulfonyl)piperazin-1-
 yl]quinolin-3-yl}ethyl)-6-methyl-[1,3,5]triazine-2,4-
 diamine,
(S)-Ethyl 2-(4-{3-[1-(4-amino-6-methyl-[1,3,5]triazin-2-
 ylamino)ethyl]-8-chloroquinolin-2-yl}piperazin-1-yl)
 acetate,
(S)-2(4-{3-[1-(4Amino-[1,3,5]triazin-2-ylamino)ethyl]-
 8-chloroquinolin-2-yl}piperazin-1-yl)-N,N-dimethy-
 lacetamide,
(S)-N²-(4-Methoxybenzyl)-6-methyl-N⁴-{1-[8-methyl-2-
 (pyrrolidin-1-yl)quinolin-3-yl]-ethyl}-[1,3,5]triazine-
 2,4-diamine,
(S)-4-(3-{1-[4-(4-Methoxybenzylamino)-6-methyl-[1,3,
 5]triazin-2-ylamino]ethyl}-8-methylquinolin-2-yl)pip-
 erazin-2-one,
N-{(1S)-1-[7-Fluoro-2-(pyrrolidin-1-yl)quinolin-3-yl]
 ethyl}-[1,3,5]triazine-2,4-diamine
N-[1-(3-{(1S)-1-[-(4-Amino-[1,3,5]triazin-2-yl)amino]
 ethyl}-7-fluoroquinolin-2-yl)-piperidin-4-yl]-aceta-
 mide,
N-{(1S)-1-[7-Fluoro-2-(pyrrolidin-1-yl)quinolin-3-yl]
 ethyl}-6-methyl-[1,3,5]triazine-2,4-diamine,
N-[-1-(3-{(1S)-1-[(4-Amino-6-methyl-[1,3,5]triazin-2-
 yl)amino]ethyl}-7-fluoroquinolin-2-yl)piperidin-4-yl]
 acetamide,
1-[4-(3-{(1S)-1-[(4-Amino-6-methyl-[1,3,5]triazin-2-yl)
 amino]ethyl}-7-fluoroquinolin-2-yl)piperazin-1-yl]
 ethanone,
1-[4-(3-{(1S)-1-[(4-Amino-[1,3,5]triazin-2-yl)amino]
 ethyl}-7-fluoroquinolin-2-yl-piperazin-1-yl-]ethanone,
4-{[8-Methyl-2-(pyrrolidin-1-yl)quinolin-3-yl]meth-
 oxy}-[1,3,5]triazin-2-amine,
4-{[8-Methyl-2-(morpholin-4-yl)quinolin-3-yl]meth-
 oxy}-[1,3,5]triazin-2-amine,
4-{3-[(4-Amino-[1,3,5]triazin-2-ylamino)methyl]-8-me-
 thylquinolin-2-yl}piperazin-2-one,
4-{[(4-Amino-6-methyl-[-1,3,5]triazin-2-ylamino)me-
 thyl]-8-methylquinolin-2-yl}-piperazin-2-one,
(S)-1-(4-{3-[1-(4-Amino-[1,3,5]triazin-2-ylamino)ethyl]-
 8-methylquinolin-2-yl}-piperazin-1-yl)ethanone,
4-{3-[(4-Amino-[1,3,5]triazin-2-yloxy)methyl]-8-meth-
 ylquinolin-2yl}piperazin-2-one
4-{3-[(4-Amino-6-methyl-[1,3,5]-triazin-2-yloxy)me-
 thyl]-8-methylquinolin-2-yl}-piperazin-2-one,
(S)-4-(8-Chloro-3-{1-[4-(dimethylamino)-[1,3,5]triazin-
 2-ylamino]ethyl}quinolin-2-yl)piperazin-2-one,
(S)-N²-{1-[8-Chloro-2-(3,3-difluoropyrrolidin-1-yl)
 quinolin-3-yl]-lethyl}-[1,3,5]-1triazine-2,4-diamine,
(S)-N²-{1-[8-Chloro-2-(3,3-difluoropyrrolidin-1-yl)
 quinolin-3-yl]ethyl}-6-methyl-[1,3,5]triazine-2,4-di-
 amine,
N²-[(S)-1-{8-Chloro-2-[(R)-3-fluoropyrrolidin-1-yl]
 quinolin-3-yl}ethyl]-[1,3,5]triazine-2,4-diamine,
N²-[(S)-1-{8-Chloro-2-[(R)-3-fluoropyrrolidin-1-yl]
 quinolin-3-yl}ethyl]-6-methyl-[1,3,5]1triazine-2,4-di-
 amine,
N²-[(S)-1-{8-Chloro-2-[(S)-3-fluoropyrrolidin-1-yl]
 quinolin-3-yl}ethyl]-6-methyl-[1,3,5]triazine-2,4-di-
 amine,
(S)-Ethyl 2(4-{3-[-1-(4amino-[1,3,5]triazin-2-ylamino)
 ethyl]-8-chloroquinolin-2-yl}piperazin-1-yl)acetate,
(S)-4-{3-[1-(4-Amino-[1,3,5]triazin-2-ylamino)ethyl]-8-
 chloroquinolin-2-yl}-N,N-dimethylpiperazine-1-car-
 boxamide,
(S)-1-(4-{3-[1-(4Amino-6-methyl-[1,3,5]triazin-2-
 ylamino)ethyl]-8-chloroquinolin-2-yl}-[1,4]diazepan-
 1-yl)ethanone,
(S)-4-(7-Fluoro-8-methyl-3-{1-[4-(methylamino)-[1,3,5]
 triazin-2-ylamino]ethyl}-quinolin-2-yl)piperazin-2-
 one,
(S)-N²-{1-[7-Fluoro-8-methyl-2-(pyrrolidin-1-yl)quino-
 lin-3-yl]ethyl}-6-methyl-[1,3,5]triazine-2,4-diamine,
(S)-2-[4-(8-Chloro-3-{1-[4-(methylamino)-[1,3,5]triazin-
 2-ylamino]ethyl}quinolin-2-yl)piperazin-1-yl]ethanol,
(S)-2-(4-{3-[1-(4-Amino-[1,3,5]triazin-2-ylamino)ethyl]-
 8-chloroquinolin-2-yl}piperazin-1-yl)ethanol,
(S)-2-(4-{3-[1-(4-Amino-6-methyl-[1,3,5]triazin-2-
 ylamino)ethyl]-8-chloroquinolin-2-yl}piperazin-1-yl)
 ethanol,
(S)-1-(4-{3-[1-(4Amino-[1,3,5]triazin-2-ylamino)ethyl]-
 7-fluoro-8-methylquinolin-2-yl}piperazin-1-yl)-2-hy-
 droxyethanone,
(S)-Ethyl 2-[4-(8-chloro-3-{1-[4-(methylamino)-[1,3,5]
 triazin-2-ylamino]ethyl}quinolin-2-yl)piperazin-1-yl]
 acetate,
(S)-2-(4-{3-[1-(4-Amino-6-methyl-[1,3,5]triazin-2-
 ylamino)ethyl]-8-chloroquinolin-2-yl}piperazin-1-yl)
 acetic acid,
(S)-2-[4-(8-Chloro-3-{1-[4-(methylamino)-[1,3,5]triazin-
 2-ylamino]ethyl}quinolin-2-yl)piperazin-1-yl]acetic
 acid,
N-{[(R)-1-{3-[(S)-1-(4-Amino-6-methyl-[1,3,5]triazin-2-
 ylamino)ethyl]-8-chloro-quinolin-2-yl}pyrrolidin-3-
 yl]methyl}acetamide,
(S)-1-{3-[1-(4-Amino-6-methyl-[1,3,5]triazin-2-
 ylamino)ethyl]-7-fluoro-8-methyl-quinolin-2-
 yl}piperidine-4-carboxamide,
(S)-1-{3-[1-(4-Amino-[1,3,5]triazin-2-ylamino)ethyl]-7-
 fluoro-8-methylquinolin-2-yl}piperidine-4-carboxam-
 ide,
(S)-N²-(1-{7-Fluoro-8-methyl-2-[4-(2,2,2-trifluoroethyl)
 piperazin-1-yl]quinolin-3-yl}ethyl)-6-methyl-[1,3,5]
 triazine-2,4-diamine,
N²-[(S)-1-{2-[(3S,5R)-3,5-Dimethylpiperazin-1-yl]-7-
 fluoro-8-methylquinolin-3-yl}ethyl]-6-methyl-[1,3,5]
 triazine-2,4-diamine, (S)-N²-{1-[7-Fluoro-2-(4-isopropylpiperazin-1-yl)-8-methylquinolin-3-yl]ethyl}-6-methyl-[1,3,5]triazine-2,4-diamine, (S)-1-(4-{3-[1-(4-Amino-6-methyl-[1,3,5]triazin-2-ylamino)ethyl]-7-fluoro-8-methylquinolin-2-yl}piperazin-1-yl)-2,2-dimethylpropan-1-one, (S)-4-{3-[1-(4-Amino-[1,3,5]triazin-2-ylamino)ethyl]-8-bromoquinolin-2-yl}piperazin-2-one, (S)-4-{3-[1-(4-Amino-6-methyl-[1,3,5]triazin-2-ylamino)ethyl]-5-fluoro-8-methyl-quinolin-2-yl}piperazin-2-one, N-[(R)-1-{3-[(S)-1-(4-Amino-6-methyl-[1,3,5]triazin-2-ylamino)ethyl]-7-fluoro-8-methylquinolin-2-yl}pyrrolidin-3-yl]acetamide, N-[(R)-1-{3-[(S)-1-(4-Amino-[1,3,5]triazin-2-ylamino)ethyl]-7-fluoro-8-methylquinolin-2-yl}pyrrolidin-3-yl]acetamide, (S)-N -(1-{3-[1-(4-Amino-6-methyl-[1,3,5]triazin-2-ylamino)ethyl]-8-chloroquinolin-2-yl}piperidin-4-yl)acetamide, (S)-N-(1-{3-[1-(4-Amino-[1,3,5]triazin-2-ylamino)ethyl]-8-chloroquinolin-2-yl}-piperidin-4-yl)acetamide, (S)-N²-{1-[8-chloro-2-([1,4]oxazepan-4-yl)quinolin-3-yl]ethyl}-6-methyl-[1,3,5]triazine-2,4-diamine, (S)-Methyl 4-{3-[1-(4-amino-[1,3,5]triazin-2-ylamino)ethyl]-7-fluoro-8-methylquinolin-2-yl}piperazine-1-carboxylate, N²-[(S)-1-{8-chloro-2-[(R)-2-(methoxymethyl)pyrrolidin-1-yl]quinolin-3-yl}ethyl]-6-methyl-[1,3,5]triazine-2,4-diamine, N²-[(S)-1-{8-Chloro-2-[(S)-2-(methoxymethyl)pyrrolidin-1-yl]quinolin-3-yl}ethyl]-[1,3,5]triazine-2,4-diamine, N²-[(S)-1-{8-Chloro-2-[(R)-2-(methoxymethyl)pyrrolidin-1-yl]quinolin-3-yl}ethyl]-[1,3,5]triazine-2,4-diamine, N²-[(S)-1-{8-Chloro-2-[(S)-2-(methoxymethyl)pyrrolidin-1-yl]quinolin-3-yl}ethyl]-6-methyl-[1,3,5]triazine-2,4-diamine, 4-{3-[(4-Amino-[1,3,5]triazin-2-ylamino)methyl]-8-chloroquinolin-2-yl}piperazin-2-one, and N-oxides, and pharmaceutically acceptable salts and solvates of any of the above compounds.

12. A pharmaceutical composition comprising a compound of formula (I) as defined in claim 1 or an N-oxide thereof, or a pharmaceutically acceptable salt or solvate thereof, in association with a pharmaceutically acceptable carrier.

\* \* \* \* \*